(12) United States Patent
Geba et al.

(10) Patent No.: US 11,472,870 B2
(45) Date of Patent: Oct. 18, 2022

(54) PHARMACEUTICAL COMPOSITION FOR SAFE AND EFFECTIVE TREATMENT OF KNEE AND/OR HIP PAIN

(71) Applicant: REGENERON PHARMACEUTICALS, INC., Tarrytown, NY (US)

(72) Inventors: Gregory Geba, Sparta, NJ (US); Paula Dakin, Armonk, NY (US); Stephen DiMartino, Scarsdale, NY (US); Haitao Gao, Sr., Parsippany, NJ (US); Jennifer Maloney, Hastings-on-Hudson, NY (US); John Davis, Scarsdale, NY (US); Catherine Stehman Breen, York, ME (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 16/536,706

(22) Filed: Aug. 9, 2019

(65) Prior Publication Data

US 2020/0048337 A1 Feb. 13, 2020

Related U.S. Application Data

(60) Provisional application No. 62/764,816, filed on Aug. 15, 2018, provisional application No. 62/717,435, filed on Aug. 10, 2018.

(51) Int. Cl.
| | | |
|---|---|---|
| *A61K 39/395* | (2006.01) | |
| *C07K 16/22* | (2006.01) | |
| *A61P 29/00* | (2006.01) | |
| *A61P 25/02* | (2006.01) | |
| *A61P 19/02* | (2006.01) | |

(52) U.S. Cl.
CPC .......... *C07K 16/22* (2013.01); *A61K 39/3955* (2013.01); *A61P 25/02* (2018.01); *A61P 29/00* (2018.01); *A61P 19/02* (2018.01); *C07K 2317/565* (2013.01)

(58) Field of Classification Search
CPC ................ C07K 16/22; C07K 2317/56; A61K 39/3955; A61P 29/00; A61P 25/02; A61P 19/02
See application file for complete search history.

(56) References Cited

U.S. PATENT DOCUMENTS

2011/0014208 A1 1/2011 MacDonald

FOREIGN PATENT DOCUMENTS

| WO | WO 2006/110883 A2 | 10/2006 |
|---|---|---|
| WO | WO 2009/023540 A1 | 2/2009 |
| WO | WO 2011/0049758 A1 | 4/2011 |
| WO | WO 2011/116090 A1 | 9/2011 |
| WO | WO 2013/184871 A1 | 12/2013 |
| WO | WO 2018/102294 A1 | 6/2018 |

OTHER PUBLICATIONS

Chang et al., J. of Pain Research 9 (2016): 373-383.*
Tieso Paul J. et al. "Fasinumab (REGN475), an antibody against nerve growth factor for the treatment of pain: Reuslts from a double-blind, placebo-controlled exploratory study in osteoarthritis of the knee", Pain, Elsevier Science Publishers, Amsterdam, NL, vol. 155, No. 7, Mar. 29, 2014 (Mar. 29, 2014), pp. 1245-1252.
Tieso Paul J. et al., "Fasinumab (REGN475), an antinerve growth factor monoclonal antibody, for the treatment of acute sciatic pain: results of a proof-of-concept study" Journal of Pain Research, Aug. 1, 2014 (Aug. 1, 2014), p. 523.

* cited by examiner

*Primary Examiner* — Robert C Hayes
(74) *Attorney, Agent, or Firm* — Lathrop GPM LLP; James H. Velema, Esq.; James V. De Giulio, Esq.

(57) ABSTRACT

A pharmaceutical composition and a method for treating knee and/or hip pain in a patient non-responsive or intolerant to standard analgesic therapy are disclosed. A pharmaceutical composition and a method for reducing risk for developing an arthropathy in a subject receiving an anti-NGF antibody for treatment of knee and/or hip pain are disclosed. Also provided herein are methods for monitoring safety of a treatment of knee and/or hip pain involving administration of an anti-NGF antibody. In certain aspects, the subject has osteoarthritis of the knee and/or hip and the anti-NGF antibody is fasinumab.

2 Claims, 69 Drawing Sheets

Specification includes a Sequence Listing.

| Study Week | Follow-Up Period | | | | | End of Study | Early Termination |
|---|---|---|---|---|---|---|---|
| | Week 20 | Week 24 | Week 28 | Week 32 | | Week 36 | |
| Study Day (visit window) | 141 (±7) | 169 (±7) | 197 (±7) | 225 (±7) | | 253 (±7) | |
| Visit Number | Visit 9 | Phone call 2 | Phone call 3 | Phone call 4 | | Visit 10 | |
| Treatment: | | | | | | | |
| Acetaminophen accountability (count)[1] | X | | | | | | |
| Concomitant medications | X | X | X | X | | X | X |
| Patient-Completed Assessments/Efficacy: | | | | | | | |
| NRS-average daily walking index joint pain[2] | X | | | | | | |
| WOMAC Pain Subscale – index joint only | | | | | | | |
| WOMAC Full Survey | X | | | | | X | X |
| Patient Global Assessment of OA | X | | | | | X | X |
| SF-36 | X | | | | | X | X |
| MOS Sleep Scale Survey | X | | | | | X | X |
| EQ-5D | X | | | | | X | X |
| Actigraphy[3] | | | | | | | |
| Safety: | | | | | | | |
| Vital signs[4] | X | | | | | X | X |
| Electrocardiogram | X | | | | | | |
| Orthostatic blood pressure | | | | | | | |
| Physical examination with joint exam | | | | | | | |
| Joint pain questionnaire[6] | X | X | X | X | | X[5] | X[5] |
| Survey of Autonomic Symptoms | X | | | | | X | X |
| Neurological evaluation | X-BRIEF | | | | | X-FULL | X-FULL |
| Radiograph knees, hip, and shoulders (bilateral)[7] | | | | | | X | X[10] |
| MRI[8] | | | | | | | X[10] |
| For TJR Follow-up: Hip Harris Score/Knee Society Score[9] | | | | X | | X | X |
| Adverse events | X | X | X | X | | X | X |
| Laboratory Testing: | | | | | | | |
| Hematology | | | | | | X | X |
| Blood chemistry | | | | | | X | X |
| Urinalysis | | | | | | | |
| Pregnancy test (for WOCBP) | Urine | | | | | Serum | Serum |
| PK, Antibody, and Proteomic Sampling: | | | | | | | |
| PK sample | | | | | | | |
| Anti-drug antibody sample | | | | | | X | X |
| Research serum/plasma sample | | | | | | X | X |

FIG. 3

| Follow-up Study Day (Visit Window) | Post-Operative Follow-up Visit 1 — 4 weeks after the date of the joint replacement surgery — F/U Day 29 (±5) | Long-Term Follow-up Visit 2 — 20 weeks after the date of the joint replacement surgery — F/U Day 140 (±7) |
|---|---|---|
| Treatment: | | |
| Concomitant medications | X | X |
| Safety: | | |
| Vital signs | X | X |
| Physical examination with joint exam | X | X |
| Post-operative assessment questionnaire [2] | X | |
| Radiograph knees, hips, and shoulders (bilateral) | | X |
| MRI [3] | | X |

FIG. 4

|  | Placebo (N=83) | Fasinumab | | | | Combined (N=338) | Total (N=421) |
|  |  | 1 mg (N=85) | 3 mg (N=84) | 6 mg (N=85) | 9 mg (N=84) | | |
|---|---|---|---|---|---|---|---|
| Subjects screened |  |  |  |  |  |  | 1214 |
| Subjects randomized | 83 | 85 | 84 | 85 | 84 | 338 | 421 |
| Randomized subjects who received at least 1 dose of study medication | 82 (98.8%) | 85 (100%) | 84 (100%) | 85 (100%) | 83 (98.8%) | 337 (99.7%) | 419 (99.5%) |
| Subjects who completed treatment period per protocol | 67 (80.7%) | 72 (84.7%) | 72 (85.7%) | 74 (87.1%) | 76 (90.5%) | 294 (87.0%) | 361 (85.7%) |
| Subjects who completed week 16 | 71 (85.5%) | 78 (91.8%) | 79 (94.0%) | 78 (91.8%) | 80 (95.2%) | 315 (93.2%) | 386 (91.7%) |
| Subjects who withdrew from the study before week 16 | 12 (14.5%) | 7 (8.2%) | 5 (6.0%) | 7 (8.2%) | 4 (4.8%) | 23 (6.8%) | 35 (8.3%) |
| Subjects who withdrew from the study after week 16 | 8 (9.6%) | 12 (14.1%) | 9 (10.7%) | 8 (9.4%) | 7 (8.3%) | 36 (10.7%) | 44 (10.5%) |
| Subjects who completed the study | 63 (75.9%) | 66 (77.6%) | 70 (83.3%) | 70 (82.4%) | 73 (86.9%) | 279 (82.5%) | 342 (81.2%) |
| Subjects who discontinued study drug | 16 (19.3%) | 13 (15.3%) | 12 (14.3%) | 11 (12.9%) | 8 (9.5%) | 44 (13.0%) | 60 (14.3%) |
| Subjects who withdrew from the study | 20 (24.1%) | 19 (22.4%) | 14 (16.7%) | 15 (17.6%) | 11 (13.1%) | 59 (17.5%) | 79 (18.8%) |
| Reason for stopping study drug before week 16 |  |  |  |  |  |  |  |
| NONCOMPLIANCE WITH PROTOCOL BY THE PATIENT | 1 (1.2%) | 0 | 1 (1.2%) | 1 (1.2%) | 0 | 2 (0.6%) | 3 (0.7%) |
| ADVERSE EVENT | 3 (3.6%) | 3 (3.5%) | 5 (6.0%) | 1 (1.2%) | 3 (3.6%) | 12 (3.6%) | 15 (3.6%) |
| PREGNANCY | 0 | 0 | 0 | 0 | 0 | 0 | 0 |

FIG. 5

|  | Placebo (N=83) | Fasinumab 1 mg (N=85) | Fasinumab 3 mg (N=84) | Fasinumab 6 mg (N=85) | Fasinumab 9 mg (N=84) | Combined (N=338) | Total (N=421) |
|---|---|---|---|---|---|---|---|
| LACK OF EFFICACY | 3 (3.6%) | 0 | 0 | 0 | 0 | 0 | 3 (0.7%) |
| INVESTIGATOR/SPONSOR DECISION | 2 (2.4%) | 2 (2.4%) | 1 (1.2%) | 2 (2.4%) | 1 (1.2%) | 6 (1.8%) | 8 (1.9%) |
| PATIENT WITHDRAWAL OF CONSENT | 7 (8.4%) | 8 (9.4%) | 3 (3.6%) | 5 (5.9%) | 3 (3.6%) | 19 (5.6%) | 26 (6.2%) |
| LOST TO FOLLOW-UP | 2 (2.4%) | 0 | 2 (2.4%) | 2 (2.4%) | 1 (1.2%) | 5 (1.5%) | 7 (1.7%) |
| DEATH | 0 | 0 | 0 | 0 | 0 | 0 | 0 |
| Reason for early withdrawal from the study before week 16 | | | | | | | |
| NONCOMPLIANCE WITH PROTOCOL BY THE PATIENT | 0 | 0 | 0 | 0 | 0 | 0 | 0 |
| ADVERSE EVENT | 0 | 2 (2.4%) | 1 (1.2%) | 2 (2.4%) | 0 | 5 (1.5%) | 5 (1.2%) |
| PREGNANCY | 0 | 0 | 0 | 0 | 0 | 0 | 0 |
| LACK OF EFFICACY | 3 (3.6%) | 2 (2.4%) | 0 | 0 | 1 (1.2%) | 3 (0.9%) | 6 (1.4%) |
| INVESTIGATOR/SPONSOR DECISION | 2 (2.4%) | 0 | 1 (1.2%) | 1 (1.2%) | 0 | 2 (0.6%) | 4 (1.0%) |
| PATIENT WITHDRAWAL OF CONSENT | 6 (7.2%) | 3 (3.5%) | 2 (2.4%) | 2 (2.4%) | 2 (2.4%) | 9 (2.7%) | 15 (3.6%) |
| LOST TO FOLLOW-UP | 1 (1.2%) | 0 | 1 (1.2%) | 2 (2.4%) | 1 (1.2%) | 4 (1.2%) | 5 (1.2%) |
| DEATH | 0 | 0 | 0 | 0 | 0 | 0 | 0 |

FIG. 5 continued

| | Placebo (N=83) | Fasinumab 1 mg (N=85) | 3 mg (N=84) | 6 mg (N=85) | 9 mg (N=84) | Combined (N=338) |
|---|---|---|---|---|---|---|
| Number of protocol deviations | 497 | 568 | 539 | 488 | 421 | 2016 |
| Number of major protocol deviations | 52 | 56 | 64 | 41 | 57 | 218 |
| Number of minor protocol deviations | 445 | 512 | 475 | 447 | 364 | 1798 |
| Subjects with any protocol deviation | 77 (92.8%) | 77 (90.6%) | 82 (97.6%) | 84 (98.8%) | 78 (92.9%) | 321 (95.0%) |
| Subjects with any major protocol deviation | 36 (43.4%) | 36 (42.4%) | 40 (47.6%) | 32 (37.6%) | 36 (42.9%) | 144 (42.6%) |
| Subjects with any minor protocol deviation | 77 (92.8%) | 75 (88.2%) | 81 (96.4%) | 82 (96.5%) | 76 (90.5%) | 314 (92.9%) |
| Type of major protocol deviation | | | | | | |
| Inclusion criteria not met | 36 (43.4%) | 36 (42.4%) | 40 (47.6%) | 32 (37.6%) | 36 (42.9%) | 144 (42.6%) |
| Exclusion criteria met | 4 (4.8%) | 5 (5.9%) | 3 (3.6%) | 2 (2.4%) | 2 (2.4%) | 12 (3.6%) |
| Visit not performed | 3 (3.6%) | 2 (2.4%) | 3 (3.6%) | 2 (2.4%) | 4 (4.8%) | 11 (3.3%) |
| Visit performed out of window | 3 (3.6%) | 2 (2.4%) | 4 (4.8%) | 3 (3.5%) | 3 (3.6%) | 12 (3.6%) |
| Procedure not performed | 0 | 0 | 0 | 0 | 0 | 0 |
| Procedure performed out of window | 7 (8.4%) | 14 (16.5%) | 12 (14.3%) | 10 (11.8%) | 7 (8.3%) | 43 (12.7%) |
| Treatment deviation | 0 | 0 | 0 | 0 | 0 | 0 |
| Prohibited medications | 7 (8.4%) | 3 (3.5%) | 3 (3.6%) | 3 (3.5%) | 3 (3.6%) | 12 (3.6%) |
| Handling of investigational product was not performed in accordance with the protocol | 18 (21.7%) | 23 (27.1%) | 24 (28.6%) | 12 (14.1%) | 21 (25.0%) | 80 (23.7%) |
| Inadequate informed consent administration | 0 | 1 (1.2%) | 1 (1.2%) | 1 (1.2%) | 0 | 3 (0.9%) |
| Inadequate source documents | 0 | 0 | 0 | 1 (1.2%) | 0 | 1 (0.3%) |
| Personnel not qualified and/or designated to perform study-related activities | 0 | 0 | 0 | 0 | 0 | 0 |
| IVR anomalies | 0 | 0 | 0 | 1 (1.2%) | 1 (1.2%) | 2 (0.6%) |
| Other | 0 | 0 | 0 | 0 | 0 | 0 |

IVR = Interactive Voice Response

FIG. 6

| | Placebo (N=83) | Fasinumab | | | | |
|---|---|---|---|---|---|---|
| | | 1 mg (N=85) | 3 mg (N=84) | 6 mg (N=85) | 9 mg (N=84) | Combined (N=338) |
| Subjects with any protocol deviation leading to exclusion from PPS | 22 (26.5%) | 26 (30.6%) | 25 (29.8%) | 15 (17.6%) | 24 (28.6%) | 90 (26.6%) |
| Type of major protocol deviation | 22 (26.5%) | 26 (30.6%) | 25 (29.8%) | 15 (17.6%) | 24 (28.6%) | 90 (26.6%) |
| Inclusion criteria not met | 3 (3.6%) | 5 (5.9%) | 3 (3.6%) | 1 (1.2%) | 2 (2.4%) | 11 (3.3%) |
| Exclusion criteria met | 0 | 1 (1.2%) | 0 | 0 | 0 | 1 (0.3%) |
| Visit not performed | 0 | 0 | 0 | 0 | 0 | 0 |
| Visit performed out of window | 0 | 0 | 0 | 0 | 0 | 0 |
| Procedure not performed | 0 | 0 | 0 | 0 | 0 | 0 |
| Procedure performed out of window | 0 | 0 | 0 | 0 | 0 | 0 |
| Treatment deviation | 1 (1.2%) | 0 | 0 | 0 | 1 (1.2%) | 1 (0.3%) |
| Prohibited medications | 18 (21.7%) | 23 (27.1%) | 24 (28.6%) | 12 (14.1%) | 21 (25.0%) | 80 (23.7%) |
| Handling of investigational product was not performed in accordance with the protocol | 0 | 0 | 0 | 0 | 0 | 0 |
| Inadequate informed consent administration | 0 | 1 (1.2%) | 1 (1.2%) | 1 (1.2%) | 0 | 3 (0.9%) |
| Inadequate source documents | 0 | 0 | 0 | 1 (1.2%) | 0 | 1 (0.3%) |
| Personnel not qualified and/or designated to perform study-related activities | 0 | 0 | 0 | 0 | 0 | 0 |
| IVR anomalies | 0 | 0 | 0 | 0 | 0 | 0 |
| Other | 0 | 0 | 0 | 0 | 0 | 0 |

IVR = Interactive Voice Response; PPS = Per Protocol Set
Source: Post-text Table 14.1.1.4-3

FIG. 7

| Analysis Set | Placebo (N=83) | Fasinumab | | | | | Total (N=421) |
| --- | --- | --- | --- | --- | --- | --- | --- |
| | | 1 mg (N=85) | 3 mg (N=84) | 6 mg (N=85) | 9 mg (N=84) | Combined (N=338) | |
| FAS | 83 (100%) | 85 (100%) | 84 (100%) | 85 (100%) | 84 (100%) | 338 (100%) | 421 (100%) |
| SAF | 82 (98.8%) | 85 (100%) | 84 (100%) | 85 (100%) | 83 (98.8%) | 337 (99.7%) | 419 (99.5%) |
| PPS | 61 (73.5%) | 59 (69.4%) | 59 (70.2%) | 70 (82.4%) | 60 (71.4%) | 248 (73.4%) | 309 (73.4%) |
| FAS = Full Analysis Set; SAF = Safety Analysis Set; PPS = Per Protocol Set | | | | | | | |

FIG. 8

|  | Placebo (N=83) | Fasinumab 1 mg (N=85) | Fasinumab 3 mg (N=84) | Fasinumab 6 mg (N=85) | Fasinumab 9 mg (N=84) | Combined (N=338) | Total (N=421) |
|---|---|---|---|---|---|---|---|
| Age (years) | | | | | | | |
| n | 83 | 85 | 84 | 85 | 84 | 338 | 421 |
| Mean (SD) | 60.1 (7.20) | 60.7 (8.88) | 60.7 (8.87) | 60.1 (7.93) | 61.5 (7.75) | 60.7 (8.35) | 60.6 (8.15) |
| Median | 60.0 | 60.0 | 60.0 | 59.0 | 61.5 | 60.0 | 60.0 |
| Q1:Q3 | 55:66 | 54:66 | 54:67 | 55:65 | 56:67 | 55:67 | 55:66 |
| Min:Max | 45:77 | 40:79 | 40:77 | 40:79 | 41:79 | 40:79 | 40:79 |
| Sex n (%) | | | | | | | |
| MALE | 29 (34.9%) | 26 (30.6%) | 30 (35.7%) | 34 (40.0%) | 30 (35.7%) | 120 (35.5%) | 149 (35.4%) |
| FEMALE | 54 (65.1%) | 59 (69.4%) | 54 (64.3%) | 51 (60.0%) | 54 (64.3%) | 218 (64.5%) | 272 (64.6%) |
| Ethnicity n (%) | | | | | | | |
| HISPANIC OR LATINO | 8 (9.6%) | 7 (8.2%) | 5 (6.0%) | 10 (11.8%) | 4 (4.8%) | 26 (7.7%) | 34 (8.1%) |
| NOT HISPANIC OR LATINO | 75 (90.4%) | 77 (90.6%) | 78 (92.9%) | 74 (87.1%) | 79 (94.0%) | 308 (91.1%) | 383 (91.0%) |
| NOT REPORTED | 0 | 1 (1.2%) | 1 (1.2%) | 1 (1.2%) | 1 (1.2%) | 4 (1.2%) | 4 (1.0%) |
| Race n (%) | | | | | | | |
| WHITE | 65 (78.3%) | 64 (75.3%) | 61 (72.6%) | 61 (71.8%) | 67 (79.8%) | 253 (74.9%) | 318 (75.5%) |
| BLACK OR AFRICAN AMERICAN | 16 (19.3%) | 16 (18.8%) | 22 (26.2%) | 20 (23.5%) | 16 (19.0%) | 74 (21.9%) | 90 (21.4%) |
| ASIAN | 1 (1.2%) | 2 (2.4%) | 1 (1.2%) | 1 (1.2%) | 1 (1.2%) | 5 (1.5%) | 6 (1.4%) |
| AMERICAN INDIAN OR ALASKA NATIVE | 0 | 1 (1.2%) | 0 | 1 (1.2%) | 0 | 2 (0.6%) | 2 (0.5%) |
| NATIVE HAWAIIAN OR OTHER PACIFIC ISLANDER | 1 (1.2%) | 0 | 0 | 0 | 0 | 0 | 1 (0.2%) |
| OTHER | 0 | 2 (2.4%) | 0 | 1 (1.2%) | 0 | 3 (0.9%) | 3 (0.7%) |
| NOT REPORTED | 0 | 0 | 0 | 1 (1.2%) | 0 | 1 (0.3%) | 1 (0.2%) |
| Weight (kg) | | | | | | | |
| n | 83 | 85 | 84 | 84 | 84 | 337 | 420 |
| Mean (SD) | 91.4 (17.22) | 84.9 (17.97) | 90.1 (16.72) | 87.3 (16.42) | 90.0 (16.35) | 88.3 (16.97) | 88.9 (17.04) |
| Median | 91.3 | 83.0 | 92.5 | 87.0 | 88.0 | 87.6 | 88.3 |
| Q1:Q3 | 76:104 | 74:96 | 77:101 | 76:99 | 79:103 | 76:100 | 76:101 |
| Min:Max | 59:137 | 54:129 | 52:133 | 51:120 | 50:136 | 50:136 | 50:137 |

FIG. 9

| | Placebo (N=83) | Fasinumab | | | | Combined (N=338) | Total (N=421) |
|---|---|---|---|---|---|---|---|
| | | 1 mg (N=85) | 3 mg (N=84) | 6 mg (N=85) | 9 mg (N=84) | | |
| Height (cm) | | | | | | | |
| n | 83 | 85 | 84 | 85 | 84 | 338 | 421 |
| Mean (SD) | 169.1 (10.97) | 166.3 (9.88) | 170.5 (10.80) | 168.9 (8.79) | 169.1 (10.62) | 168.7 (9.92) | 168.8 (10.10) |
| Median | 168.0 | 165.1 | 169.5 | 168.0 | 167.8 | 167.6 | 167.6 |
| Q1 : Q3 | 163 : 177 | 159 : 174 | 163 : 178 | 163 : 176 | 163 : 176 | 163 : 175 | 163 : 176 |
| Min : Max | 137 : 196 | 142 : 191 | 151 : 193 | 147 : 191 | 145 : 203 | 142 : 203 | 137 : 203 |
| BMI (kg/m²) | | | | | | | |
| n | 83 | 85 | 84 | 84 | 84 | 337 | 420 |
| Mean (SD) | 31.84 (4.585) | 30.56 (5.030) | 30.93 (4.719) | 30.53 (4.887) | 31.80 (4.988) | 30.95 (4.913) | 31.12 (4.849) |
| Median | 31.83 | 30.39 | 31.40 | 30.57 | 31.34 | 31.18 | 31.29 |
| Q1 : Q3 | 28.4 : 35.8 | 26.8 : 34.9 | 27.4 : 34.7 | 27.8 : 33.9 | 28.3 : 36.0 | 27.3 : 34.9 | 27.6 : 35.0 |
| Min : Max | 22.5 : 40.1 | 20.8 : 39.1 | 21.5 : 39.4 | 16.6 : 39.0 | 17.2 : 39.3 | 16.6 : 39.4 | 16.6 : 40.1 |
| Index Joint n (%) | | | | | | | |
| HIP | 9 (10.8%) | 10 (11.8%) | 10 (11.9%) | 11 (12.9%) | 10 (11.9%) | 41 (12.1%) | 50 (11.9%) |
| KNEE | 74 (89.2%) | 75 (88.2%) | 74 (88.1%) | 74 (87.1%) | 74 (88.1%) | 297 (87.9%) | 371 (88.1%) |
| Kellgren-Lawrence Score n (%) | | | | | | | |
| 1 | 0 | 0 | 0 | 0 | 1 (1.2%) | 1 (0.3%) | 1 (0.2%) |
| 2 | 23 (27.7%) | 31 (36.5%) | 30 (35.7%) | 30 (35.3%) | 28 (33.3%) | 119 (35.2%) | 142 (33.7%) |
| 3 | 26 (31.3%) | 20 (23.5%) | 21 (25.0%) | 20 (23.5%) | 21 (25.0%) | 82 (24.3%) | 108 (25.7%) |
| 4 | 34 (41.0%) | 34 (40.0%) | 33 (39.3%) | 35 (41.2%) | 34 (40.5%) | 136 (40.2%) | 170 (40.4%) |

BMI = Body Mass Index

FIG. 9 continued

| System Organ Class Preferred Term | Placebo (N=83) | Fasinumab | | | | Combined (N=338) | Total (N=421) |
|---|---|---|---|---|---|---|---|
| | | 1 mg (N=85) | 3 mg (N=84) | 6 mg (N=85) | 9 mg (N=84) | | |
| Subjects with at least one medical history finding | 83 (100%) | 85 (100%) | 84 (100%) | 85 (100%) | 84 (100%) | 338 (100%) | 421 (100%) |
| Musculoskeletal and connective tissue disorders | 83 (100%) | 85 (100%) | 84 (100%) | 85 (100%) | 84 (100%) | 338 (100%) | 421 (100%) |
| Osteoarthritis | 83 (100%) | 85 (100%) | 83 (98.8%) | 85 (100%) | 84 (100%) | 337 (99.7%) | 420 (99.8%) |
| Back pain | 14 (16.9%) | 17 (20.0%) | 16 (19.0%) | 11 (12.9%) | 20 (23.8%) | 64 (18.9%) | 78 (18.5%) |
| Arthralgia | 11 (13.3%) | 16 (18.8%) | 10 (11.9%) | 10 (11.8%) | 15 (17.9%) | 51 (15.1%) | 62 (14.7%) |
| Surgical and medical procedures | 58 (69.9%) | 52 (61.2%) | 50 (59.5%) | 51 (60.0%) | 46 (54.8%) | 199 (58.9%) | 257 (61.0%) |
| Hysterectomy | 16 (19.3%) | 16 (18.8%) | 12 (14.3%) | 16 (18.8%) | 12 (14.3%) | 56 (16.6%) | 72 (17.1%) |
| Cholecystectomy | 11 (13.3%) | 9 (10.6%) | 9 (10.7%) | 9 (10.6%) | 9 (10.7%) | 36 (10.7%) | 47 (11.2%) |
| Female sterilisation | 4 (4.8%) | 14 (16.5%) | 5 (6.0%) | 6 (7.1%) | 5 (6.0%) | 30 (8.9%) | 34 (8.1%) |
| Metabolism and nutrition disorders | 39 (47.0%) | 46 (54.1%) | 44 (52.4%) | 44 (51.8%) | 38 (45.2%) | 172 (50.9%) | 211 (50.1%) |
| Hyperlipidaemia | 13 (15.7%) | 14 (16.5%) | 17 (20.2%) | 16 (18.8%) | 14 (16.7%) | 61 (18.0%) | 74 (17.6%) |
| Hypercholesterolaemia | 12 (14.5%) | 20 (23.5%) | 10 (11.9%) | 16 (18.8%) | 10 (11.9%) | 56 (16.6%) | 68 (16.2%) |
| Type 2 diabetes mellitus | 5 (6.0%) | 11 (12.9%) | 11 (13.1%) | 8 (9.4%) | 11 (13.1%) | 41 (12.1%) | 46 (10.9%) |
| Vascular disorders | 48 (57.8%) | 43 (50.6%) | 41 (48.8%) | 42 (49.4%) | 46 (54.8%) | 172 (50.9%) | 220 (52.3%) |
| Hypertension | 46 (55.4%) | 39 (45.9%) | 39 (46.4%) | 33 (38.8%) | 45 (53.6%) | 156 (46.2%) | 202 (48.0%) |
| Immune system disorders | 31 (37.3%) | 38 (44.7%) | 40 (47.6%) | 29 (34.1%) | 34 (40.5%) | 141 (41.7%) | 172 (40.9%) |
| Seasonal allergy | 22 (26.5%) | 31 (36.5%) | 22 (26.2%) | 20 (23.5%) | 24 (28.6%) | 97 (28.7%) | 119 (28.3%) |
| Drug hypersensitivity | 13 (15.7%) | 14 (16.5%) | 18 (21.4%) | 9 (10.6%) | 14 (16.7%) | 55 (16.3%) | 68 (16.2%) |
| Gastrointestinal disorders | 33 (39.8%) | 35 (41.2%) | 33 (39.3%) | 29 (34.1%) | 39 (46.4%) | 136 (40.2%) | 169 (40.1%) |
| Gastroesophageal reflux disease | 18 (21.7%) | 24 (28.2%) | 21 (25.0%) | 15 (17.6%) | 30 (35.7%) | 90 (26.6%) | 108 (25.7%) |
| Psychiatric disorders | 31 (37.3%) | 32 (37.6%) | 30 (35.7%) | 24 (28.2%) | 37 (44.0%) | 123 (36.4%) | 154 (36.6%) |
| Depression | 20 (24.1%) | 13 (15.3%) | 19 (22.6%) | 19 (15.3%) | 23 (27.4%) | 67 (19.8%) | 87 (20.7%) |
| Insomnia | 15 (18.1%) | 17 (20.0%) | 17 (20.2%) | 11 (12.9%) | 16 (19.0%) | 61 (18.0%) | 76 (18.1%) |
| Anxiety | 8 (9.6%) | 7 (8.2%) | 12 (14.3%) | 11 (12.9%) | 11 (13.1%) | 41 (12.1%) | 49 (11.6%) |
| Nervous system disorders | 31 (37.3%) | 29 (34.1%) | 25 (29.8%) | 28 (32.9%) | 29 (34.5%) | 111 (32.8%) | 142 (33.7%) |
| Migraine | 6 (7.2%) | 7 (8.2%) | 11 (13.1%) | 7 (8.2%) | 12 (14.3%) | 37 (10.9%) | 43 (10.2%) |
| Headache | 8 (9.6%) | 6 (7.1%) | 9 (10.7%) | 5 (5.9%) | 9 (10.7%) | 29 (8.6%) | 37 (8.8%) |
| Social circumstances | 20 (24.1%) | 25 (29.4%) | 26 (31.0%) | 23 (27.1%) | 26 (31.0%) | 100 (29.6%) | 120 (28.5%) |
| Postmenopause | 16 (19.3%) | 16 (18.8%) | 19 (22.6%) | 16 (18.8%) | 21 (25.0%) | 72 (21.3%) | 88 (20.9%) |
| Eye disorders | 23 (27.7%) | 25 (29.4%) | 28 (33.3%) | 23 (27.1%) | 20 (23.8%) | 96 (28.4%) | 119 (28.3%) |

FIG. 10

|  | Placebo (N=83) | \multicolumn{5}{c}{Fasinumab} | | | | | Total (N=421) |
|---|---|---|---|---|---|---|---|
| System Organ Class Preferred Term | | 1 mg (N=85) | 3 mg (N=84) | 6 mg (N=85) | 9 mg (N=84) | Combined (N=338) | |
| Myopia | 10 (12.0%) | 4 (4.7%) | 6 (7.1%) | 7 (8.2%) | 5 (6.0%) | 22 (6.5%) | 32 (7.6%) |
| Injury, poisoning and procedural complications | 28 (33.7%) | 25 (29.4%) | 21 (25.0%) | 22 (25.9%) | 23 (27.4%) | 91 (26.9%) | 119 (28.3%) |
| Meniscus injury | 12 (14.5%) | 7 (8.2%) | 7 (8.3%) | 4 (4.7%) | 10 (11.9%) | 28 (8.3%) | 40 (9.5%) |
| Respiratory, thoracic and mediastinal disorders | 17 (20.5%) | 23 (27.1%) | 21 (25.0%) | 17 (20.0%) | 22 (26.2%) | 83 (24.6%) | 100 (23.8%) |
| Asthma | 10 (12.0%) | 11 (12.9%) | 11 (13.1%) | 9 (10.6%) | 5 (6.0%) | 36 (10.7%) | 46 (10.9%) |
| Investigations | 18 (21.7%) | 17 (20.0%) | 18 (21.4%) | 15 (17.6%) | 16 (19.0%) | 66 (19.5%) | 84 (20.0%) |
| Arthroscopy | 10 (12.0%) | 2 (2.4%) | 5 (6.0%) | 7 (8.2%) | 5 (6.0%) | 19 (5.6%) | 29 (6.9%) |
| Endocrine disorders | 19 (22.9%) | 13 (15.3%) | 16 (19.0%) | 14 (16.5%) | 21 (25.0%) | 64 (18.9%) | 83 (19.7%) |
| Hypothyroidism | 15 (18.1%) | 7 (8.2%) | 13 (15.5%) | 14 (16.5%) | 19 (22.6%) | 53 (15.7%) | 68 (16.2%) |
| Renal and urinary disorders | 20 (24.1%) | 18 (21.2%) | 11 (13.1%) | 12 (14.1%) | 18 (21.4%) | 59 (17.5%) | 79 (18.8%) |
| Urinary incontinence | 2 (2.4%) | 4 (4.7%) | 4 (4.8%) | 1 (1.2%) | 5 (6.0%) | 14 (4.1%) | 16 (3.8%) |
| Nephrolithiasis | 10 (12.0%) | 2 (2.4%) | 1 (1.2%) | 4 (4.7%) | 3 (3.6%) | 10 (3.0%) | 20 (4.8%) |

FIG. 10 continued

| | Placebo (N=82) | Fasinumab | | | |
|---|---|---|---|---|---|
| | | 1 mg (N=85) | 3 mg (N=84) | 6 mg (N=85) | 9 mg (N=83) | Combined (N=337) |
| Compliance | | | | | | |
| n | 82 | 85 | 84 | 85 | 83 | 337 |
| Mean (SD) | 92.9 (16.93) | 93.9 (14.96) | 93.3 (16.23) | 93.5 (16.88) | 95.8 (12.23) | 94.1 (15.16) |
| Median | 100.0 | 100.0 | 100.0 | 100.0 | 100.0 | 100.0 |
| Q1 : Q3 | 100 : 100 | 100 : 100 | 100 : 100 | 100 : 100 | 100 : 100 | 100 : 100 |
| Min : Max | 25 : 100 | 33 : 100 | 25 : 100 | 25 : 100 | 25 : 100 | 25 : 100 |

FIG. 11

|  | Placebo (N=83) | Fasinumab | | | |
|---|---|---|---|---|---|
|  |  | 1 mg (N=85) | 3 mg (N=84) | 6 mg (N=85) | 9 mg (N=84) |
| Baseline | | | | | |
| N | 83 | 85 | 84 | 85 | 84 |
| Mean (SD) | 6.43 (1.661) | 6.33 (1.643) | 6.35 (1.599) | 6.10 (1.424) | 6.53 (1.474) |
| Median | 6.40 | 6.20 | 6.20 | 6.20 | 6.60 |
| Q1 : Q3 | 5.4 : 7.8 | 5.0 : 7.6 | 5.2 : 7.6 | 5.0 : 7.2 | 5.4 : 7.8 |
| Min : Max | 1.4 : 10.0 | 3.0 : 9.4 | 3.0 : 10.0 | 2.0 : 9.6 | 3.6 : 10.0 |
| Week 16 | | | | | |
| N | 71 | 75 | 78 | 77 | 79 |
| Mean (SD) | 3.94 (2.578) | 2.82 (2.173) | 2.88 (2.311) | 3.16 (2.383) | 2.67 (2.446) |
| Median | 4.20 | 2.40 | 2.40 | 2.80 | 2.20 |
| Q1 : Q3 | 1.4 : 6.4 | 1.0 : 4.6 | 0.8 : 5.0 | 1.2 : 4.8 | 0.6 : 4.4 |
| Min : Max | 0.0 : 9.0 | 0.0 : 8.2 | 0.0 : 7.6 | 0.0 : 8.0 | 0.0 : 10.0 |
| Change from Baseline | | | | | |
| N | 71 | 75 | 78 | 77 | 79 |
| Mean (SD) | -2.43 (2.378) | -3.49 (2.056) | -3.39 (2.443) | -3.07 (2.340) | -3.81 (2.480) |
| Median | -2.20 | -3.20 | -3.50 | -3.40 | -3.80 |
| Q1 : Q3 | -4.0 : -0.6 | -4.6 : -1.8 | -5.2 : -1.8 | -4.6 : -1.0 | -6.0 : -2.0 |
| Min : Max | -8.6 : 2.2 | -8.4 : 0.2 | -7.8 : 2.6 | -7.6 : 1.6 | -8.8 : 1.2 |
| LS Mean (SE) | -2.25 (0.286) | -3.39 (0.278) | -3.33 (0.277) | -3.03 (0.276) | -3.65 (0.277) |
| 95% CI | (-2.81, -1.69) | (-3.89, -2.80) | (-3.87, -2.78) | (-3.57, -2.49) | (-4.19, -3.10) |
| Difference vs. Placebo | | | | | |
| LS Mean (SE) |  | -1.10 (0.362) | -1.08 (0.361) | -0.78 (0.361) | -1.40 (0.361) |
| 95% CI |  | (-1.81, -0.39) | (-1.79, -0.37) | (-1.50, -0.07) | (-2.11, -0.69) |
| P-value |  | 0.0025 | 0.0029 | 0.0304 | 0.0001 |

FIG. 12

|  | Placebo (N=83) | Fasinumab | | | |
|---|---|---|---|---|---|
|  |  | 1 mg (N=85) | 3 mg (N=84) | 6 mg (N=85) | 9 mg (N=84) |
| Baseline | | | | | |
| N | 83 | 84 | 84 | 84 | 84 |
| Mean (SD) | 3.1 (0.83) | 3.2 (0.78) | 3.1 (0.86) | 3.1 (0.88) | 3.2 (0.87) |
| Median | 3.0 | 3.0 | 3.0 | 3.0 | 3.0 |
| Q1 : Q3 | 3.4 | 3.4 | 3.4 | 3.4 | 3.4 |
| Min : Max | 1:5 | 2:5 | 1:5 | 1:5 | 1:5 |
| Week 16 | | | | | |
| N | 71 | 75 | 77 | 76 | 80 |
| Mean (SD) | 2.4 (0.98) | 2.1 (0.86) | 2.3 (0.97) | 2.2 (0.83) | 2.0 (0.86) |
| Median | 2.0 | 2.0 | 2.0 | 2.0 | 2.0 |
| Q1 : Q3 | 2:3 | 1:3 | 2:3 | 2:3 | 1:2 |
| Min : Max | 1:5 | 1:4 | 1:5 | 1:4 | 1:4 |
| Change from Baseline | | | | | |
| N | 71 | 74 | 77 | 76 | 80 |
| Mean (SD) | -0.7 (0.96) | -1.0 (0.99) | -0.8 (1.15) | -0.9 (1.15) | -1.2 (1.19) |
| Median | -1.0 | -1.0 | -1.0 | -1.0 | -1.0 |
| Q1 : Q3 | -1:0 | -2:0 | -2:0 | -2:0 | -2:-1 |
| Min : Max | -4:1 | -4:1 | -3:2 | -3:2 | -4:1 |
| LS Mean (SE) | -0.6 (0.11) | -1.0 (0.11) | -0.8 (0.11) | -0.9 (0.11) | -1.1 (0.11) |
| 95% CI | (-0.8, -0.4) | (-1.2, -0.8) | (-1.1, -0.6) | (-1.1, -0.7) | (-1.3, -0.9) |
| Difference vs. Placebo | | | | | |
| LS Mean (SE) |  | -0.4 (0.15) | -0.2 (0.14) | -0.2 (0.15) | -0.5 (0.14) |
| 95% CI |  | (-0.6, -0.1) | (-0.5, 0.1) | (-0.5, 0.0) | (-0.8, -0.2) |
| P-value |  | 0.0132 | 0.1466 | 0.0881 | 0.0008 |

FIG. 17

|  | Placebo (N=83) | Fasinumab | | | |
| --- | --- | --- | --- | --- | --- |
|  |  | 1 mg (N=85) | 3 mg (N=84) | 6 mg (N=85) | 9 mg (N=84) |
| Subjects who use Rescue Medication n (%) | 75 (90.4%) | 75 (88.2%) | 66 (78.6%) | 80 (94.1%) | 70 (83.3%) |
| Odds Ratio [1] |  | 0.82 | 0.39 | 1.71 | 0.55 |
| (95% CI) |  | (0.31, 2.16) | (0.15, 0.98) | (0.56, 5.22) | (0.22, 1.37) |
| P-value[2] |  | 0.6760 | 0.0396 | 0.3358 | 0.1862 |

FIG. 20

|  | Placebo (N=82) | Fasinumab 1 mg (N=85) | Fasinumab 3 mg (N=84) | Fasinumab 6 mg (N=85) | Fasinumab 9 mg (N=83) | Combined (N=337) |
|---|---|---|---|---|---|---|
| Number of injections, n(%) | | | | | | |
| 1 | 7 (8.5%) | 5 (5.9%) | 3 (3.6%) | 4 (4.7%) | 2 (2.4%) | 14 (4.2%) |
| 2 | 4 (4.9%) | 3 (3.5%) | 5 (6.0%) | 3 (3.5%) | 1 (1.2%) | 12 (3.6%) |
| 3 | 8 (9.8%) | 8 (9.4%) | 9 (10.7%) | 10 (11.8%) | 10 (12.0%) | 37 (11.0%) |
| 4 | 63 (76.8%) | 69 (81.2%) | 67 (79.8%) | 68 (80.0%) | 70 (84.3%) | 274 (81.3%) |
| Duration of treatment (days)[1] | | | | | | |
| n | 82 | 85 | 84 | 85 | 83 | 337 |
| Mean (SD) | 100.6 (26.31) | 104.0 (22.42) | 104.6 (20.38) | 104.0 (21.03) | 107.6 (16.01) | 105.0 (20.09) |
| Median | 112.0 | 112.0 | 112.0 | 112.0 | 112.0 | 112.0 |
| Q1 : Q3 | 108 : 113 | 110 : 113 | 110 : 113 | 108 : 114 | 109 : 114 | 109 : 113 |
| Min : Max | 28 : 119 | 28 : 119 | 28 : 119 | 28 : 119 | 28 : 119 | 28 : 119 |
| Duration of treatment by category, n(%) | | | | | | |
| >=1 Day | 82 (100%) | 85 (100%) | 84 (100%) | 85 (100%) | 83 (100%) | 337 (100%) |
| >=8 Days | 82 (100%) | 85 (100%) | 84 (100%) | 85 (100%) | 83 (100%) | 337 (100%) |
| >=15 Days | 82 (100%) | 85 (100%) | 84 (100%) | 85 (100%) | 83 (100%) | 337 (100%) |
| >=29 Days | 75 (91.5%) | 80 (94.1%) | 81 (96.4%) | 81 (95.3%) | 81 (97.6%) | 323 (95.8%) |
| >=57 Days | 71 (86.6%) | 78 (91.8%) | 78 (92.9%) | 80 (94.1%) | 81 (97.6%) | 317 (94.1%) |
| >=85 Days | 67 (81.7%) | 74 (87.1%) | 74 (88.1%) | 72 (84.7%) | 76 (91.6%) | 296 (87.8%) |
| >=113 Days | 21 (25.6%) | 25 (29.4%) | 21 (25.0%) | 30 (35.3%) | 27 (32.5%) | 103 (30.6%) |

FIG. 21

| | Placebo (N=82) | Fasinumab | | | | |
|---|---|---|---|---|---|---|
| | | 1 mg (N=85) | 3 mg (N=84) | 6 mg (N=85) | 9 mg (N=83) | Combined (N=337) |
| Duration of observation period (days)[1] | | | | | | |
| n | 82 | 85 | 84 | 85 | 83 | 337 |
| Mean (SD) | 219.4 (75.29) | 228.0 (63.26) | 235.6 (53.09) | 236.5 (55.83) | 245.4 (40.09) | 236.3 (53.91) |
| Median | 253.0 | 253.0 | 253.0 | 253.0 | 253.0 | 253.0 |
| Q1 : Q3 | 246 : 254 | 250 : 255 | 250 : 258 | 247 : 255 | 250 : 257 | 250 : 256 |
| Min : Max | 8 : 360 | 15 : 281 | 15 : 275 | 15 : 341 | 10 : 296 | 10 : 341 |
| Duration of observation period by category, n (%) | | | | | | |
| ≥ 1 Day | 82 (100%) | 85 (100%) | 84 (100%) | 85 (100%) | 83 (100%) | 337 (100%) |
| ≥ 8 Days | 82 (100%) | 85 (100%) | 84 (100%) | 85 (100%) | 83 (100%) | 337 (100%) |
| ≥ 15 Days | 81 (98.8%) | 85 (100%) | 84 (100%) | 85 (100%) | 82 (98.8%) | 336 (99.7%) |
| ≥ 29 Days | 79 (96.3%) | 83 (97.6%) | 82 (97.6%) | 84 (98.8%) | 82 (98.8%) | 331 (98.2%) |
| ≥ 57 Days | 76 (92.7%) | 81 (95.3%) | 82 (97.6%) | 83 (97.6%) | 82 (98.8%) | 328 (97.3%) |
| ≥ 85 Days | 75 (91.5%) | 80 (94.1%) | 81 (96.4%) | 82 (96.5%) | 81 (97.6%) | 324 (96.1%) |
| ≥ 113 Days | 69 (84.1%) | 77 (90.6%) | 79 (94.0%) | 79 (92.9%) | 80 (96.4%) | 315 (93.5%) |
| ≥ 141 Days | 67 (81.7%) | 76 (89.4%) | 77 (91.7%) | 76 (89.4%) | 80 (96.4%) | 309 (91.7%) |
| ≥ 169 Days | 66 (80.5%) | 72 (84.7%) | 73 (86.9%) | 76 (89.4%) | 80 (96.4%) | 301 (89.3%) |
| ≥ 197 Days | 65 (79.3%) | 71 (83.5%) | 73 (86.9%) | 75 (88.2%) | 79 (95.2%) | 298 (88.4%) |
| ≥ 225 Days | 65 (79.3%) | 70 (82.4%) | 73 (86.9%) | 74 (87.1%) | 77 (92.8%) | 294 (87.2%) |
| ≥ 253 Days | 47 (57.3%) | 49 (57.6%) | 53 (63.1%) | 49 (57.6%) | 48 (57.8%) | 199 (59.1%) |
| ≥ 281 Days | 2 (2.4%) | 1 (1.2%) | 0 | 3 (3.5%) | 3 (3.6%) | 7 (2.1%) |
| ≥ 309 Days | 2 (2.4%) | 0 | 0 | 3 (3.9%) | 0 | 3 (0.9%) |
| ≥ 337 Days | 1 (1.2%) | 0 | 0 | 1 (1.2%) | 0 | 1 (0.3%) |
| ≥ 365 Days | 0 | 0 | 0 | 0 | 0 | 0 |

FIG. 22

|  | Placebo (N=82) | Fasinumab | | | | Combined (N=337) |
|---|---|---|---|---|---|---|
|  |  | 1 mg (N=85) | 3 mg (N=84) | 6 mg (N=85) | 9 mg (N=83) |  |
| Total number of TEAEs | 94 | 145 | 120 | 123 | 118 | 506 |
| Total number of TEAEs related to study drug | 17 | 24 | 26 | 21 | 20 | 91 |
| Total number of serious TEAEs | 4 | 2 | 3 | 0 | 0 | 5 |
| Total number of severe TEAEs | 6 | 4 | 5 | 2 | 1 | 12 |
| Subjects with any TEAE | 45 (54.9%) | 54 (63.5%) | 52 (61.9%) | 55 (64.7%) | 48 (57.8%) | 209 (62.0%) |
| Subjects with TEAEs related to study drug | 8 (9.8%) | 11 (12.9%) | 17 (20.2%) | 12 (14.1%) | 16 (19.3%) | 56 (16.6%) |
| Subjects with any serious TEAE | 2 (2.4%) | 2 (2.4%) | 2 (2.4%) | 0 | 0 | 4 (1.2%) |
| Subjects with any severe TEAE | 4 (4.9%) | 4 (4.7%) | 3 (3.6%) | 2 (2.4%) | 1 (1.2%) | 10 (3.0%) |
| Subjects with any TEAE resulting in permanent discontinuation of study drug[1] | 1 (1.2%) | 5 (5.9%) | 5 (6.0%) | 1 (1.2%) | 3 (3.6%) | 14 (4.2%) |
| Subjects with any TEAE leading to withdrawal from study | 1 (1.2%) | 2 (2.4%) | 1 (1.2%) | 1 (1.2%) | 0 | 4 (1.2%) |
| Subjects with any TEAE leading to death | 0 | 0 | 0 | 0 | 0 | 0 |

FIG. 23

|  | Placebo (N=82) | Fasinumab | | | | Combined (N=337) |
|---|---|---|---|---|---|---|
|  |  | 1 mg (N=85) | 3 mg (N=84) | 6 mg (N=85) | 9 mg (N=83) |  |
| Total number of Post-Treatment AEs | 53 | 74 | 97 | 100 | 101 | 372 |
| Total number of serious Post-Treatment AEs | 5 | 5 | 4 | 8 | 10 | 27 |
| Total number of severe Post-Treatment AEs | 3 | 5 | 6 | 10 | 14 | 35 |
| Subjects with any Post-Treatment AE | 31 (37.8%) | 36 (42.4%) | 38 (45.2%) | 42 (49.4%) | 44 (53.0%) | 160 (47.5%) |
| Subjects with any serious Post-Treatment AE | 4 (4.9%) | 5 (5.9%) | 3 (3.6%) | 5 (5.9%) | 7 (8.4%) | 20 (5.9%) |
| Subjects with any severe Post-Treatment AE | 3 (3.7%) | 4 (4.7%) | 4 (4.8%) | 8 (9.4%) | 10 (12.0%) | 26 (7.7%) |
| Subjects with any Post-Treatment AE resulting in permanent discontinuation of study drug | 0 | 0 | 0 | 0 | 1 (1.2%) | 1 (0.3%) |
| Subjects with any Post-Treatment AE leading to withdrawal from study | 1 (1.2%) | 0 | 1 (1.2%) | 0 | 2 (2.4%) | 3 (0.9%) |
| Subjects with any Post-Treatment AE leading to death | 0 | 0 | 0 | 0 | 0 | 0 |

FIG. 24

| System Organ Class Preferred Term | Placebo (N=82) | Fasinumab 1 mg (N=85) | Fasinumab 3 mg (N=84) | Fasinumab 6 mg (N=85) | Fasinumab 9 mg (N=83) | Combined (N=337) |
|---|---|---|---|---|---|---|
| Number of TEAEs | 94 | 145 | 120 | 123 | 118 | 506 |
| Number of subjects with at least one TEAE | 45 (54.9%) | 54 (63.5%) | 52 (61.9%) | 55 (64.7%) | 48 (57.8%) | 209 (62.0%) |
| Arthralgia | 2 (2.4%) | 9 (10.6%) | 5 (6.0%) | 8 (9.4%) | 5 (6.0%) | 27 (8.0%) |
| Back pain | 2 (2.4%) | 4 (4.7%) | 1 (1.2%) | 2 (2.4%) | 3 (3.6%) | 10 (3.0%) |
| Joint swelling | 0 | 1 (1.2%) | 6 (7.1%) | 3 (3.5%) | 0 | 10 (3.0%) |
| Pain in extremity | 3 (3.7%) | 3 (3.5%) | 1 (1.2%) | 2 (2.4%) | 4 (4.8%) | 10 (3.0%) |
| Musculoskeletal pain | 4 (4.9%) | 0 | 1 (1.2%) | 2 (2.4%) | 1 (1.2%) | 4 (1.2%) |
| Osteoarthritis | 0 | 0 | 0 | 0 | 3 (3.6%) | 3 (0.9%) |
| Headache | 5 (6.1%) | 7 (8.2%) | 2 (2.4%) | 4 (4.7%) | 4 (4.8%) | 17 (5.0%) |
| Paraesthesia | 0 | 2 (2.4%) | 4 (4.8%) | 0 | 4 (4.8%) | 10 (3.0%) |
| Dizziness | 2 (2.4%) | 3 (3.5%) | 2 (2.4%) | 3 (3.5%) | 1 (1.2%) | 9 (2.7%) |
| Hypoaesthesia | 1 (1.2%) | 2 (2.4%) | 3 (3.6%) | 2 (2.4%) | 1 (1.2%) | 8 (2.4%) |
| Upper respiratory tract infection | 1 (1.2%) | 5 (5.9%) | 3 (3.6%) | 3 (3.5%) | 7 (8.4%) | 18 (5.3%) |
| Urinary tract infection | 3 (3.7%) | 5 (5.9%) | 1 (1.2%) | 4 (4.7%) | 3 (3.6%) | 13 (3.9%) |
| Sinusitis | 3 (3.7%) | 1 (1.2%) | 2 (2.4%) | 2 (2.4%) | 4 (4.8%) | 9 (2.7%) |
| Nausea | 3 (3.7%) | 6 (7.1%) | 1 (1.2%) | 2 (2.4%) | 1 (1.2%) | 10 (3.0%) |
| Diarrhoea | 3 (3.7%) | 1 (1.2%) | 4 (4.8%) | 4 (4.7%) | 2 (2.4%) | 8 (2.4%) |
| Dry mouth | 1 (1.2%) | 3 (3.5%) | 3 (3.6%) | 1 (1.2%) | 0 | 8 (2.4%) |
| Vomiting | 0 | 1 (1.2%) | 3 (3.6%) | 1 (1.2%) | 2 (2.4%) | 7 (2.1%) |
| Oedema peripheral | 0 | 0 | 2 (2.4%) | 3 (3.5%) | 6 (7.2%) | 11 (3.3%) |
| Fatigue | 1 (1.2%) | 2 (2.4%) | 1 (1.2%) | 3 (3.5%) | 0 | 6 (1.8%) |
| Orthostatic hypotension | 3 (3.7%) | 3 (3.5%) | 3 (3.6%) | 3 (3.5%) | 2 (2.4%) | 11 (3.3%) |
| Hypertension | 4 (4.9%) | 1 (1.2%) | 1 (1.2%) | 2 (2.4%) | 1 (1.2%) | 5 (1.5%) |
| Rash | 0 | 1 (1.2%) | 2 (2.4%) | 1 (1.2%) | 4 (4.8%) | 8 (2.4%) |

FIG. 25

| Preferred Term | Placebo (N=82) | Fasinumab | | | | Combined (N=337) |
|---|---|---|---|---|---|---|
| | | 1 mg (N=85) | 3 mg (N=84) | 6 mg (N=85) | 9 mg (N=83) | |
| Number of Post-Treatment AEs | 53 | 74 | 97 | 100 | 101 | 372 |
| Number of subjects with at least one Post-Treatment AE | 31 (37.8%) | 36 (42.4%) | 38 (45.2%) | 42 (49.4%) | 44 (53.0%) | 160 (47.5%) |
| Arthralgia | 5 (6.1%) | 3 (3.5%) | 11 (13.1%) | 12 (14.1%) | 9 (10.8%) | 35 (10.4%) |
| Rapidly progressive osteoarthritis | 0 | 2 (2.4%) | 2 (2.4%) | 5 (5.9%) | 7 (8.4%) | 16 (4.7%) |
| Osteoarthritis | 0 | 3 (3.5%) | 4 (4.8%) | 3 (3.5%) | 4 (4.8%) | 14 (4.2%) |
| Musculoskeletal pain | 2 (2.4%) | 2 (2.4%) | 5 (6.0%) | 4 (4.7%) | 1 (1.2%) | 12 (3.6%) |
| Upper respiratory tract infection | 0 | 2 (2.4%) | 7 (8.3%) | 3 (3.5%) | 0 | 12 (3.6%) |
| Orthostatic hypotension | 4 (4.9%) | 2 (2.4%) | 4 (4.8%) | 0 | 4 (4.8%) | 10 (3.0%) |
| Joint swelling | 1 (1.2%) | 1 (1.2%) | 2 (2.4%) | 4 (4.7%) | 1 (1.2%) | 8 (2.4%) |
| Pain in extremity | 1 (1.2%) | 1 (1.2%) | 1 (1.2%) | 3 (3.5%) | 2 (2.4%) | 7 (2.1%) |
| Urinary tract infection | 2 (2.4%) | 3 (3.5%) | 2 (2.4%) | 0 | 1 (1.2%) | 6 (1.8%) |
| Bronchitis | 1 (1.2%) | 0 | 1 (1.2%) | 0 | 3 (3.6%) | 4 (1.2%) |

FIG. 26

| System Organ Class Preferred Term | Placebo (N=82) | Fasinumab | | | | Combined (N=337) |
|---|---|---|---|---|---|---|
| | | 1 mg (N=85) | 3 mg (N=84) | 6 mg (N=85) | 9 mg (N=83) | |
| Number of treatment-related TEAEs | 17 | 24 | 26 | 21 | 20 | 91 |
| Number of subjects with at least one treatment-related TEAE | 8 (9.8%) | 11 (12.9%) | 17 (20.2%) | 12 (14.1%) | 16 (19.3%) | 56 (16.6%) |
| Nervous system disorders | 3 (3.7%) | 7 (8.2%) | 5 (6.0%) | 7 (8.2%) | 6 (7.2%) | 25 (7.4%) |
| Paraesthesia | 0 | 2 (2.4%) | 3 (3.6%) | 0 | 3 (3.6%) | 8 (2.4%) |
| Headache | 2 (2.4%) | 4 (4.7%) | 0 | 1 (1.2%) | 1 (1.2%) | 6 (1.8%) |
| Dizziness | 1 (1.2%) | 1 (1.2%) | 1 (1.2%) | 3 (3.5%) | 0 | 5 (1.5%) |
| Hypoaesthesia | 1 (1.2%) | 1 (1.2%) | 2 (2.4%) | 0 | 1 (1.2%) | 4 (1.2%) |
| Gastrointestinal disorders | 2 (2.4%) | 2 (2.4%) | 4 (4.8%) | 3 (3.5%) | 1 (1.2%) | 10 (3.0%) |
| Nausea | 1 (1.2%) | 2 (2.4%) | 1 (1.2%) | 1 (1.2%) | 1 (1.2%) | 5 (1.5%) |
| Musculoskeletal and connective tissue disorders | 2 (2.4%) | 2 (2.4%) | 5 (6.0%) | 3 (3.5%) | 0 | 10 (3.0%) |
| Arthralgia | 1 (1.2%) | 1 (1.2%) | 3 (3.6%) | 1 (1.2%) | 0 | 5 (1.5%) |
| Skin and subcutaneous tissue disorders | 0 | 1 (1.2%) | 1 (1.2%) | 1 (1.2%) | 4 (4.8%) | 7 (2.1%) |
| Rash | 0 | 0 | 0 | 1 (1.2%) | 3 (3.6%) | 4 (1.2%) |
| Vascular disorders | 2 (2.4%) | 2 (2.4%) | 1 (1.2%) | 0 | 1 (1.2%) | 4 (1.2%) |
| Orthostatic hypotension | 1 (1.2%) | 2 (2.4%) | 1 (1.2%) | 0 | 1 (1.2%) | 4 (1.2%) |

FIG. 27

| System Organ Class Preferred Term | Placebo (N=82) | Fasinumab | | | | Combined (N=337) |
|---|---|---|---|---|---|---|
| | | 1 mg (N=85) | 3 mg (N=84) | 6 mg (N=85) | 9 mg (N=83) | |
| Number of treatment-related Post-Treatment AEs | 3 | 5 | 17 | 8 | 13 | 43 |
| Number of subjects with at least one treatment-related Post-Treatment AE | 3 (3.7%) | 5 (5.9%) | 7 (8.3%) | 6 (7.1%) | 9 (10.8%) | 27 (8.0%) |
| Musculoskeletal and connective tissue disorders | 1 (1.2%) | 2 (2.4%) | 7 (8.3%) | 6 (7.1%) | 7 (8.4%) | 22 (6.5%) |
| Rapidly progressive osteoarthritis | 0 | 2 (2.4%) | 2 (2.4%) | 4 (4.7%) | 5 (6.0%) | 13 (3.9%) |
| Arthralgia | 1 (1.2%) | 0 | 4 (4.8%) | 2 (2.4%) | 1 (1.2%) | 7 (2.1%) |
| Musculoskeletal pain | 0 | 0 | 2 (2.4%) | 0 | 0 | 2 (0.6%) |
| Injury, poisoning and procedural complications | 1 (1.2%) | 0 | 2 (2.4%) | 1 (1.2%) | 1 (1.2%) | 4 (1.2%) |
| Stress fracture | 1 (1.2%) | 0 | 2 (2.4%) | 0 | 1 (1.2%) | 3 (0.9%) |

FIG. 28

|  |  | Fasinumab | | | | |
| --- | --- | --- | --- | --- | --- | --- |
| System Organ Class<br>Preferred Term | Placebo<br>(N=82) | 1 mg<br>(N=85) | 3 mg<br>(N=84) | 6 mg<br>(N=85) | 9 mg<br>(N=83) | Combined<br>(N=337) |
| Number of serious TEAEs | 4 | 2 | 3 | 0 | 0 | 5 |
| Number of subjects with at least one serious TEAE | 2 (2.4%) | 2 (2.4%) | 2 (2.4%) | 0 | 0 | 4 (1.2%) |
| Blood and lymphatic system disorders | 0 | 0 | 1 (1.2%) | 0 | 0 | 1 (0.3%) |
| Anaemia | 0 | 0 | 1 (1.2%) | 0 | 0 | 1 (0.3%) |
| Infections and infestations | 0 | 1 (1.2%) | 0 | 0 | 0 | 1 (0.3%) |
| Nasal abscess | 0 | 1 (1.2%) | 0 | 0 | 0 | 1 (0.3%) |
| Respiratory, thoracic and mediastinal disorders | 0 | 1 (1.2%) | 0 | 0 | 0 | 1 (0.3%) |
| Asthma | 0 | 1 (1.2%) | 0 | 0 | 0 | 1 (0.3%) |
| Vascular disorders | 0 | 0 | 1 (1.2%) | 0 | 0 | 1 (0.3%) |
| Aortic aneurysm rupture | 0 | 0 | 1 (1.2%) | 0 | 0 | 1 (0.3%) |
| Hypertensive crisis | 0 | 0 | 1 (1.2%) | 0 | 0 | 1 (0.3%) |
| Metabolism and nutrition disorders | 1 (1.2%) | 0 | 0 | 0 | 0 | 0 |
| Dehydration | 1 (1.2%) | 0 | 0 | 0 | 0 | 0 |
| Musculoskeletal and connective tissue disorders | 1 (1.2%) | 0 | 0 | 0 | 0 | 0 |
| Musculoskeletal pain | 1 (1.2%) | 0 | 0 | 0 | 0 | 0 |
| Nervous system disorders | 1 (1.2%) | 0 | 0 | 0 | 0 | 0 |
| Headache | 1 (1.2%) | 0 | 0 | 0 | 0 | 0 |
| Syncope | 1 (1.2%) | 0 | 0 | 0 | 0 | 0 |

FIG. 29

| System Organ Class Preferred Term | Placebo (N=82) | Fasinumab | | | | Combined (N=337) |
|---|---|---|---|---|---|---|
| | | 1 mg (N=85) | 3 mg (N=84) | 6 mg (N=85) | 9 mg (N=83) | |
| Number of serious Post-Treatment AEs | 5 | 5 | 4 | 8 | 10 | 27 |
| Number of subjects with at least one serious Post-Treatment AE | 4 (4.9%) | 5 (5.9%) | 3 (3.6%) | 5 (5.9%) | 7 (8.4%) | 20 (5.9%) |
| Musculoskeletal and connective tissue disorders | 1 (1.2%) | 1 (1.2%) | 1 (1.2%) | 3 (3.5%) | 2 (2.4%) | 7 (2.1%) |
| Osteoarthritis | 0 | 1 (1.2%) | 1 (1.2%) | 1 (1.2%) | 1 (1.2%) | 4 (1.2%) |
| Osteonecrosis | 0 | 0 | 0 | 1 (1.2%) | 1 (1.2%) | 2 (0.6%) |
| Joint effusion | 0 | 0 | 0 | 0 | 1 (1.2%) | 1 (0.3%) |
| Lumbar spinal stenosis | 0 | 0 | 0 | 1 (1.2%) | 0 | 1 (0.3%) |
| Rapidly progressive osteoarthritis | 0 | 0 | 0 | 1 (1.2%) | 0 | 1 (0.3%) |
| Intervertebral disc protrusion | 1 (1.2%) | 0 | 0 | 0 | 0 | 0 |
| Surgical and medical procedures | 2 (2.4%) | 1 (1.2%) | 1 (1.2%) | 2 (2.4%) | 1 (1.2%) | 5 (1.5%) |
| Knee arthroplasty | 1 (1.2%) | 1 (1.2%) | 1 (1.2%) | 2 (2.4%) | 1 (1.2%) | 5 (1.5%) |
| Joint arthroplasty | 1 (1.2%) | 0 | 0 | 0 | 0 | 0 |
| Gastrointestinal disorders | 0 | 1 (1.2%) | 1 (1.2%) | 0 | 1 (1.2%) | 3 (0.9%) |
| Gastric ulcer | 0 | 0 | 1 (1.2%) | 0 | 0 | 1 (0.3%) |
| Gastrointestinal haemorrhage | 0 | 0 | 1 (1.2%) | 0 | 0 | 1 (0.3%) |
| Pharyngo-oesophageal diverticulum | 0 | 0 | 0 | 0 | 1 (1.2%) | 1 (0.3%) |
| Gastrointestinal disorders | | | | | | |
| Rectal haemorrhage | 0 | 1 (1.2%) | 0 | 0 | 0 | 1 (0.3%) |
| Injury, poisoning and procedural complications | 0 | 0 | 0 | 1 (1.2%) | 2 (2.4%) | 3 (0.9%) |
| Stress fracture | 0 | 0 | 0 | 0 | 2 (2.4%) | 2 (0.6%) |
| Femur fracture | 0 | 0 | 0 | 1 (1.2%) | 0 | 1 (0.3%) |

FIG. 30

| System Organ Class Preferred Term | Placebo (N=82) | Fasinumab | | | | Combined (N=337) |
|---|---|---|---|---|---|---|
| | | 1 mg (N=85) | 3 mg (N=84) | 6 mg (N=85) | 9 mg (N=83) | |
| Cardiac disorders | 0 | 2 (2.4%) | 0 | 0 | 0 | 2 (0.6%) |
| Acute myocardial infarction | 0 | 1 (0.2%) | 0 | 0 | 0 | 1 (0.3%) |
| Atrioventricular block second degree | 0 | 1 (1.2%) | 0 | 0 | 0 | 1 (0.3%) |
| Infections and infestations | 1 (1.2%) | 0 | 0 | 0 | 2 (2.4%) | 2 (0.6%) |
| Bronchitis | 0 | 0 | 0 | 0 | 1 (1.2%) | 1 (0.3%) |
| Urosepsis | 0 | 0 | 0 | 0 | 1 (1.2%) | 1 (0.3%) |
| Gastroenteritis viral | 1 (1.2%) | 0 | 0 | 0 | 0 | 0 |
| Hepatobiliary disorders | 0 | 0 | 0 | 0 | 1 (1.2%) | 1 (0.3%) |
| Cholelithiasis | 0 | 0 | 0 | 0 | 1 (1.2%) | 1 (0.3%) |
| Nervous system disorders | 1 (1.2%) | 0 | 0 | 0 | 0 | 0 |
| Cervical radiculopathy | 1 (1.2%) | 0 | 0 | 0 | 0 | 0 |

FIG. 30 continued

| System Organ Class Preferred Term | Placebo (N=82) | Fasinumab | | | | |
|---|---|---|---|---|---|---|
| | | 1 mg (N=85) | 3 mg (N=84) | 6 mg (N=85) | 9 mg (N=83) | Combined (N=337) |
| Number of TEAEs resulting in permanent study drug discontinuation | 1 | 7 | 7 | 1 | 3 | 18 |
| Number of subjects with at least one TEAE resulting in permanent study drug discontinuation | 1 (1.2%) | 5 (5.9%) | 5 (6.0%) | 1 (1.2%) | 3 (3.6%) | 14 (4.2%) |
| Musculoskeletal and connective tissue disorders | 1 (1.2%) | 3 (3.5%) | 2 (2.4%) | 0 | 1 (1.2%) | 6 (1.8%) |
| Arthralgia | 0 | 3 (3.5%) | 0 | 0 | 0 | 3 (0.9%) |
| Back pain | 0 | 0 | 1 (1.2%) | 0 | 1 (1.2%) | 2 (0.6%) |
| Synovial cyst | 0 | 0 | 1 (1.2%) | 0 | 0 | 2 (0.6%) |
| Muscle spasms | 1 (1.2%) | 0 | 0 | 0 | 0 | 1 (0.3%) |
| Nervous system disorders | 0 | 1 (1.2%) | 1 (1.2%) | 0 | 1 (1.2%) | 3 (0.9%) |
| Hypoaesthesia | 0 | 1 (1.2%) | 1 (1.2%) | 0 | 0 | 2 (0.6%) |
| Paraesthesia | 0 | 1 (1.2%) | 0 | 0 | 1 (1.2%) | 2 (0.6%) |
| Skin and subcutaneous tissue disorders | 0 | 1 (1.2%) | 1 (1.2%) | 0 | 1 (1.2%) | 3 (0.9%) |
| Dry skin | 0 | 0 | 1 (1.2%) | 0 | 0 | 1 (0.3%) |
| Rash | 0 | 0 | 0 | 0 | 1 (1.2%) | 1 (0.3%) |
| Rash papular | 0 | 1 (1.2%) | 0 | 0 | 0 | 1 (0.3%) |

FIG. 31

| System Organ Class Preferred Term | Placebo (N=82) | Fasinumab | | | | |
|---|---|---|---|---|---|---|
| | | 1 mg (N=85) | 3 mg (N=84) | 6 mg (N=85) | 9 mg (N=83) | Combined (N=337) |
| Vascular disorders | 0 | 1 (1.2%) | 2 (2.4%) | 0 | 0 | 3 (0.9%) |
| Orthostatic hypotension | 0 | 1 (1.2%) | 1 (1.2%) | 0 | 0 | 2 (0.6%) |
| Aortic aneurysm rupture | 0 | 0 | 1 (1.2%) | 0 | 0 | 1 (0.3%) |
| Hypertensive crisis | 0 | 0 | 1 (1.2%) | 0 | 0 | 1 (0.3%) |
| Injury, poisoning and procedural complications | 0 | 0 | 0 | 1 (1.2%) | 0 | 1 (0.3%) |
| Meniscus injury | 0 | 0 | 0 | 1 (1.2%) | 0 | 1 (0.3%) |

FIG. 31 continued

| Category Preferred Term | Placebo (N=82) | Fasinumab | | | | |
|---|---|---|---|---|---|---|
| | | 1 mg (N=85) | 3 mg (N=84) | 6 mg (N=85) | 9 mg (N=83) | Combined (N=337) |
| Number of Treatment-Emergent AESI | 0 | 0 | 0 | 0 | 1 | 1 |
| Number of subjects with at least one Treatment-Emergent AESIs | 0 | 0 | 0 | 0 | 1 (1.2%) | 1 (0.3%) |
| ADJUDICATED ARTHROPATHY | 0 | 0 | 0 | 0 | 1 (1.2%) | 1 (0.3%) |
| Stress fracture | 0 | 0 | 0 | 0 | 1 (1.2%) | 1 (0.3%) |

FIG. 32

| Category<br>Preferred Term | Placebo<br>(N=82) | Fasinumab | | | | Combined<br>(N=337) |
|---|---|---|---|---|---|---|
| | | 1 mg<br>(N=85) | 3 mg<br>(N=84) | 6 mg<br>(N=85) | 9 mg<br>(N=83) | |
| Number of AESI during follow-up | 1 | 2 | 4 | 6 | 9 | 21 |
| Number of subjects with at least one AESI during follow-up | 1 (1.2%) | 2 (2.4%) | 4 (4.8%) | 6 (7.1%) | 9 (10.8%) | 21 (6.2%) |
| ADJUDICATED ARTHROPATHY | 1 (1.2%) | 2 (2.4%) | 4 (4.8%) | 6 (7.1%) | 9 (10.8%) | 21 (6.2%) |
| Rapidly progressive osteoarthritis | 0 | 2 (2.4%) | 2 (2.4%) | 5 (5.9%) | 7 (8.4%)† | 16 (4.7%)† |
| Stress fracture | 1 (1.2%) | 0 | 2 (2.4%) | 1 (1.2%) | 2 (2.4%) | 5 (1.5%) |

FIG. 33

| Category Preferred Term | Placebo (N=82) | Fasinumab | | | | |
|---|---|---|---|---|---|---|
| | | 1 mg (N=85) | 3 mg (N=84) | 6 mg (N=85) | 9 mg (N=83) | Combined (N=337) |
| Number of AESIs | 1 | 2 | 4 | 6 | 10 | 22 |
| Number of subjects with at least one AESIs | 1 (1.2%) | 2 (2.4%) | 4 (4.8%) | 6 (7.1%) | 10 (12.0%) | 22 (6.5%) |
| ADJUDICATED ARTHROPATHY | 1 (1.2%) | 2 (2.4%) | 4 (4.8%) | 6 (7.1%) | 10 (12.0%) | 22 (6.5%) |
| Rapidly progressive osteoarthritis | 0 | 2 (2.4%) | 2 (2.4%) | 5 (5.9%) | 7 (8.4%)† | 16 (4.7%)† |
| Stress fracture | 1 (1.2%) | 0 | 2 (2.4%) | 1 (1.2%) | 3 (3.6%) | 6 (1.8%) |

FIG. 34

|  | Placebo (N=82) | Fasinumab | | | | |
|---|---|---|---|---|---|---|
|  |  | 1 mg (N=85) | 3 mg (N=84) | 6 mg (N=85) | 9 mg (N=83) | Combined (N=337) |
| Total number of adjudication events | 11 | 11 | 25 | 30 | 34 | 100 |
| Number of negative adjudication events | 10 (90.9%) | 9 (81.8%) | 21 (84.0%) | 24 (80.0%) | 22 (64.7%) | 76 (76.0%) |
| Number of patients with positive adjudications | 1 | 2 | 4 | 6 | 10 | 22 |
| Positive adjudications | 1 (9.1%) | 2 (18.2%) | 4 (16.0%) | 6 (20.0%) | 12 (35.3%) | 24 (24.0%) |
| RPOA-1 (ongoing) | 0 | 2 | 2 | 4 | 7 | 15 |
| RPOA-2 (ongoing) | 0 | 0 | 0 | 0 | 1 | 1 |
| RPOA-2→TJR | 0 | 0 | 0 | 1 | 0 | 1 |
| SIF (ongoing) | 0 | 0 | 2 | 1 | 1 | 4 |
| SIF→TJR | 0 | 0 | 0 | 0 | 2 | 2 |
| SIF→RPOA1→TJR | 0 | 0 | 0 | 0 | 1 | 1 |
| SIF→(Resolved) | 1 | 0 | 0 | 0 | 0 | 0 |

FIG. 35

| | Placebo (N=82) | Fasinumab | | | | |
|---|---|---|---|---|---|---|
| | | 1 mg (N=85) | 3 mg (N=84) | 6 mg (N=85) | 9 mg (N=83) | Combined (N=337) |
| Number of TJRs | 3 | 3 | 3 | 4 | 3 | 13 |
| Number of subjects with at least one TJR | 2 (2.4%) | 3 (3.5%) | 2 (2.4%) | 4 (4.7%) | 3 (3.6%) | 12 (3.6%) |
| Number of TJRs/1000 patient-years | 60.92 | 56.53 | 55.37 | 72.66 | 53.80 | 59.62 |
| Joint replaced | | | | | | |
| Right knee | 2 | 1 | 1 | 2 | 2 | 6 |
| Left knee | 1 | 2 | 2 | 1 | 0 | 5 |
| Right hip | 0 | 0 | 0 | 0 | 0 | 0 |
| Left hip | 0 | 0 | 0 | 1 | 1 | 2 |

FIG. 36

| Parameter (unit) Visit | Placebo (N=82) | Fasinumab 1 mg (N=85) | Fasinumab 3 mg (N=84) | Fasinumab 6 mg (N=85) | Fasinumab 9 mg (N=83) | Combined (N=337) |
|---|---|---|---|---|---|---|
| Alkaline Phosphatase (U/L) | | | | | | |
| Baseline | | | | | | |
| n | 82 | 85 | 84 | 85 | 83 | 337 |
| Mean (SD) | 80.4 (19.61) | 75.3 (21.18) | 76.7 (20.88) | 78.3 (23.50) | 78.6 (22.39) | 77.2 (21.95) |
| Median | 80.5 | 74.0 | 76.0 | 75.0 | 78.0 | 76.0 |
| Q1 : Q3 | 69 : 91 | 63 : 87 | 61 : 89 | 63 : 90 | 62 : 94 | 62 : 90 |
| Min : Max | 37 : 137 | 9 : 140 | 44 : 141 | 40 : 160 | 38 : 151 | 9 : 160 |
| Week 16 | | | | | | |
| n | 70 | 75 | 76 | 77 | 78 | 306 |
| Mean (SD) | 82.8 (20.10) | 84.5 (20.47) | 88.4 (24.88) | 96.6 (32.72) | 99.2 (27.58) | 92.3 (27.36) |
| Median | 80.0 | 82.0 | 84.0 | 89.0 | 99.0 | 89.0 |
| Q1 : Q3 | 69 : 94 | 69 : 98 | 71 : 104 | 78 : 107 | 76 : 119 | 72 : 107 |
| Min : Max | 42 : 133 | 42 : 147 | 36 : 156 | 56 : 270 | 44 : 163 | 36 : 270 |
| Change from Baseline | | | | | | |
| n | 70 | 75 | 76 | 77 | 78 | 306 |
| Mean (SD) | 2.2 (11.12) | 9.5 (11.47) | 12.8 (13.39) | 18.0 (15.69) | 20.1 (16.19) | 15.2 (14.86) |
| Median | 1.0 | 9.0 | 12.0 | 16.0 | 19.5 | 12.0 |
| Q1 : Q3 | -6 : 9 | 4 : 14 | 5 : 18 | 9 : 23 | 9 : 33 | 6 : 22 |
| Min : Max | -27 : 33 | -24 : 57 | -14 : 62 | -6 : 115 | -22 : 71 | -24 : 115 |

FIG. 37

|  | Functional Fasinumab Concentrations (mg/L) | | | | |
|---|---|---|---|---|---|
| Study Day | Placebo (N=82) | 1 mg Q4W SC (N=85) | 3 mg Q4W SC (N=84) | 6 mg Q4W SC (N=85) | 9 mg Q4W SC (N=83) |
| Day 1 PRE | | | | | |
| N | 81 | 80 | 81 | 82 | 81 |
| Mean (SD) | 0 (0) | 0 (0) | 0.00279 (0.0251) | 0 (0) | 0 (0) |
| Median | 0 | 0 | 0 | 0 | 0 |
| Q1 : Q3 | 0 : 0 | 0 : 0 | 0 : 0 | 0 : 0 | 0 : 0 |
| Min : Max | 0 : 0 | 0 : 0 | 0 : 0.226 | 0 : 0 | 0 : 0 |
| Day 15 | | | | | |
| N | 76 | 77 | 74 | 79 | 80 |
| Mean (SD) | 0 (0) | 0.0808 (0.110) | 0.271 (0.131) | 0.559 (0.236) | 0.851 (0.333) |
| Median | 0 | 0.0789 | 0.267 | 0.518 | 0.857 |
| Q1 : Q3 | 0 : 0 | 0 : 0.119 | 0.207 : 0.349 | 0.429 : 0.690 | 0.598 : 1.02 |
| Min : Max | 0 : 0 | 0 : 0.525 | 0 : 0.643 | 0 : 1.41 | 0 : 1.62 |
| Day 29 | | | | | |
| N | 74 | 77 | 78 | 81 | 79 |
| Mean (SD) | 0 (0) | 0.0345 (0.0761) | 0.178 (0.105) | 0.395 (0.172) | 0.601 (0.251) |
| Median | 0 | 0 | 0.173 | 0.368 | 0.583 |
| Q1 : Q3 | 0 : 0 | 0 : 0 | 0.133 : 0.214 | 0.283 : 0.473 | 0.406 : 0.770 |
| Min : Max | 0 : 0 | 0 : 0.369 | 0 : 0.527 | 0 : 0.903 | 0 : 1.36 |
| Day 57 | | | | | |
| N | 72 | 74 | 78 | 78 | 78 |
| Mean (SD) | 0 (0) | 0.0587 (0.112) | 0.263 (0.138) | 0.604 (0.292) | 0.903 (0.393) |
| Median | 0 | 0 | 0.268 | 0.582 | 0.882 |
| Q1 : Q3 | 0 : 0 | 0 : 0.108 | 0.177 : 0.337 | 0.372 : 0.790 | 0.623 : 1.15 |
| Min : Max | 0 : 0 | 0 : 0.741 | 0 : 0.703 | 0 : 1.54 | 0.179 : 1.93 |
| Day 85 | | | | | |
| N | 70 | 77 | 79 | 75 | 78 |
| Mean (SD) | 0.0112 (0.0846) | 0.0589 (0.0846) | 0.301 (0.171) | 0.658 (0.294) | 0.990 (0.457) |
| Median | 0 | 0 | 0.279 | 0.639 | 0.980 |
| Q1 : Q3 | 0 : 0 | 0 : 0.110 | 0.193 : 0.390 | 0.458 : 0.808 | 0.698 : 1.20 |
| Min : Max | 0 : 0.705 | 0 : 0.348 | 0 : 0.954 | 0.0925 : 1.44 | 0 : 2.63 |
| Day 113 | | | | | |
| N | 65 | 72 | 77 | 75 | 78 |
| Mean (SD) | 0 (0) | 0.0584 (0.0921) | 0.284 (0.170) | 0.668 (0.376) | 0.992 (0.444) |
| Median | 0 | 0 | 0.252 | 0.584 | 0.949 |
| Q1 : Q3 | 0 : 0 | 0 : 0.115 | 0.196 : 0.391 | 0.414 : 0.919 | 0.723 : 1.34 |
| Min : Max | 0 : 0 | 0 : 0.505 | 0 : 0.819 | 0 : 2.11 | 0 : 2.25 |

N = Number of patients; SD = Standard deviation; Q = Quartile; PRE = Pre-dose; Q4W = Once every 4 weeks; SC = Subcutaneous

FIG. 39

| Characteristic | Placebo (n = 82) | Fasinumab 1 mg (n = 85) | Fasinumab 3 mg (n = 84) | Fasinumab 6 mg (n = 85) | Fasinumab 9 mg (n = 83) | Combined (N = 337) | Total (N = 419) |
|---|---|---|---|---|---|---|---|
| Age, mean (SD), years | 60.1 (7.2) | 60.7 (8.9) | 60.7 (8.9) | 60.1 (7.9) | 61.5 (7.8) | 60.6 (8.1) | 60.6 (8.1) |
| Female, n (%) | 54 (65.1) | 59 (69.4) | 54 (64.3) | 51 (60.0) | 54 (64.3) | 218 (64.5) | 272 (64.6) |
| Caucasian, n (%) | 65 (78.3) | 64 (75.3) | 61 (72.6) | 61 (71.8) | 67 (79.8) | 253 (74.9) | 318 (75.5) |
| BMI, mean (SD), kg/m² | 31.8 (4.5) | 30.6 (5.0) | 30.9 (4.7) | 30.5 (4.9) | 31.8 (5.0) | 30.95 (4.9) | 31.12 (4.9) |
| Index joint, n (%) | | | | | | | |
| Hip | 9 (10.8) | 10 (11.8) | 10 (11.9) | 11 (12.9) | 10 (11.9) | 41 (12.1) | 50 (11.9) |
| Knee | 74 (89.2) | 75 (88.2) | 74 (88.1) | 74 (87.1) | 74 (88.1) | 297 (87.9) | 371 (88.1) |
| Kellgren–Lawrence score, n (%) | | | | | | | |
| 1 | 0 | 0 | 0 | 0 | 1 (1.2) | 1 (0.3) | 1 (0.2) |
| 2 | 23 (27.7) | 31 (36.5) | 30 (35.7) | 30 (35.3) | 28 (33.3) | 119 (35.2) | 142 (33.7) |
| 3 | 26 (31.3) | 20 (23.5) | 21 (25.0) | 20 (23.5) | 21 (25.0) | 82 (24.3) | 108 (25.7) |
| 4 | 34 (41.0) | 34 (40.0) | 33 (39.3) | 35 (41.2) | 34 (40.5) | 136 (40.2) | 170 (40.4) |

FIG. 42

|  | Placebo (n = 83) | Fasinumab | | | |
|---|---|---|---|---|---|
|  |  | 1 mg (n = 85) | 3 mg (n = 84) | 6 mg (n = 85) | 9 mg (n = 84) |
| Baseline | | | | | |
| n | 83 | 85 | 84 | 85 | 84 |
| Mean (SD) | 6.4 (1.7) | 6.3 (1.6) | 6.4 (1.6) | 6.1 (1.4) | 6.5 (1.5) |
| Median (range) | 6.4 (1.4, 10.0) | 6.2 (3.0, 9.4) | 6.2 (3.0, 10.0) | 6.2 (2.0, 9.6) | 6.6 (3.6, 10.0) |
| Week 16 | | | | | |
| n | 71 | 75 | 78 | 77 | 79 |
| Mean (SD) | 3.9 (2.6) | 2.8 (2.2) | 2.9 (2.3) | 3.2 (2.4) | 2.7 (2.5) |
| Median (range) | 4.2 (0.0, 9.0) | 2.4 (0.0, 8.2) | 2.4 (0.0, 7.6) | 2.8 (0.0, 8.0) | 2.2 (0.0, 10.0) |
| Change from baseline | | | | | |
| n | 71 | 75 | 78 | 77 | 79 |
| Mean (SD) | -2.4 (2.4) | -3.5 (2.1) | -3.4 (2.4) | -3.1 (2.3) | -3.8 (2.5) |
| Median (range) | -2.20 (-8.6, 3.2) | -3.20 (-8.4, 0.2) | -3.50 (-7.8, 2.6) | -3.40 (-7.6, 1.6) | -3.80 (-8.8, 1.2) |
| LS Mean (SE) | -2.3 (0.29) | -3.4 (0.3) | -3.3 (0.3) | -3.0 (0.3) | -3.7 (0.3) |
| 95% CI | -2.8, -1.7 | -3.9, -2.8 | -3.9, -2.8 | -3.6, -2.5 | -4.2, -3.1 |
| Difference vs placebo | | | | | |
| LS mean (SE) | — | -1.1 (0.4) | -1.1 (0.4) | -0.8 (0.4) | -1.4 (0.4) |
| 95% CI | — | -1.8, -0.4 | -1.8, -0.4 | -1.5, -0.1 | -2.1, -0.7 |
| P value | — | 0.0025 | 0.0029 | 0.0304 | 0.0001 |

FIG. 43

|  | Placebo (n = 82) | Fasinumab | | | |
|---|---|---|---|---|---|
|  |  | 1 mg (n = 85) | 3 mg (n = 84) | 6 mg (n = 85) | 9 mg (n = 83) | Combined (N = 337) |
| Treatment period |  |  |  |  |  |  |
| Number of treatment-related TEAEs | 17 | 24 | 26 | 21 | 20 | 91 |
| Patients with at ≥1 treatment-related TEAE, n (%) | 8 (9.8) | 11 (12.9) | 17 (20.2) | 12 (14.1) | 16 (19.3) | 56 (16.6) |
| Nervous system | 3 (3.7) | 7 (8.2) | 5 (6.0) | 7 (8.2) | 6 (7.2) | 25 (7.4) |
| Paresthesia | 0 | 2 (2.4) | 3 (3.6) | 0 | 3 (3.6) | 8 (2.4) |
| Headache | 2 (2.4) | 4 (4.7) | 0 | 1 (1.2) | 1 (1.2) | 6 (1.8) |
| Dizziness | 1 (1.2) | 1 (1.2) | 1 (1.2) | 3 (3.5) | 0 | 5 (1.5) |
| Hypoesthesia | 1 (1.2) | 1 (1.2) | 2 (2.4) | 0 | 1 (1.2) | 4 (1.2) |
| Gastrointestinal | 2 (2.4) | 2 (2.4) | 4 (4.8) | 3 (3.5) | 1 (1.2) | 10 (3.0) |
| Nausea | 1 (1.2) | 2 (2.4) | 1 (1.2) | 1 (1.2) | 1 (1.2) | 5 (1.5) |

FIG. 44

| | | | | | | |
|---|---|---|---|---|---|---|
| Musculoskeletal and connective tissue | 2 (2.4) | 2 (2.4) | 5 (6.0) | 3 (3.5) | 0 | 10 (3.0) |
| Arthralgia | 1 (1.2) | 1 (1.2) | 3 (3.6) | 1 (1.2) | 0 | 5 (1.5) |
| Skin and subcutaneous tissue | 0 | 1 (1.2) | 1 (1.2) | 1 (1.2) | 4 (4.8) | 7 (2.1) |
| Rash | 0 | 0 | 0 | 1 (1.2) | 3 (3.6) | 4 (1.2) |
| Vascular | 2 (2.4) | 2 (2.4) | 1 (1.2) | 0 | 1 (1.2) | 4 (1.2) |
| Orthostatic hypotension | 1 (1.2) | 2 (2.4) | 1 (1.2) | 0 | 1 (1.2) | 4 (1.2) |
| Follow-up period | | | | | | |
| Number of treatment-related post-treatment AEs | 3 | 5 | 17 | 8 | 13 | 43 |

FIG. 44 continued

| Patients with ≥1 treatment-related post-treatment AE,[a] n (%) | 3 (3.7) | 5 (5.9) | 7 (8.3) | 6 (7.1) | 9 (10.8) | 27 (8.0) |
|---|---|---|---|---|---|---|
| Musculoskeletal/connective tissue | 1 (1.2) | 2 (2.4) | 7 (8.3) | 6 (7.1) | 7 (8.4) | 22 (6.5) |
| Rapidly progressive osteoarthritis | 0 | 2 (2.4) | 2 (2.4) | 4 (4.7) | 5 (6.0) | 13 (3.9) |
| Arthralgia | 1 (1.2) | 0 | 4 (4.8) | 2 (2.4) | 1 (1.2) | 7 (2.1) |
| Musculoskeletal pain | 0 | 0 | 2 (2.4) | 0 | 0 | 2 (0.6) |
| Injury, poisoning, and procedural complications | 1 (1.2) | 0 | 2 (2.4) | 1 (1.2) | 1 (1.2) | 4 (1.2) |
| Stress fracture | 1 (1.2) | 0 | 2 (2.4) | 0 | 1 (1.2) | 3 (0.9) |

FIG. 44 continued

| | Placebo (n = 82) | Fasinumab | | | |
|---|---|---|---|---|---|
| | | 1 mg (n = 85) | 3 mg (n = 84) | 6 mg (n = 85) | 9 mg (n = 83) | Combined (N = 337) |
| Arthropathies[a] | | | | | | |
| Number of arthropathies | 1 | 2 | 4 | 6 | 10 | 22 |
| Patients with ≥1 arthropathy, n (%) | 1 (1.2) | 2 (2.4) | 4 (4.8) | 6 (7.1) | 10 (12.0) | 22 (6.5) |
| Arthropathy, n (%) | 1 (1.2) | 2 (2.4) | 4 (4.8) | 6 (7.1) | 10 (12.0) | 22 (6.5) |
| Rapidly progressive osteoarthritis | 0 | 2 (2.4) | 2 (2.4) | 5 (5.9) | 7 (8.4)[b] | 16 (4.7)[c] |
| Stress fracture | 1 (1.2) | 0 | 2 (2.4) | 1 (1.2) | 3 (3.6) | 6 (1.8) |
| Total joint replacement | | | | | | |
| Number of total joint replacements | 3 | 3 | 3 | 4 | 3 | 13 |
| Patients with ≥1 total joint replacement, n (%) | 2 (2.4) | 3 (3.5) | 2 (2.4) | 4 (4.7) | 3 (3.6) | 12 (3.6) |
| Number of total joint replacements per 1000 patient-years | 60.9 | 56.5 | 55.4 | 72.7 | 53.8 | 59.6 |
| Joint replaced | | | | | | |
| Right knee | 2 | 1 | 1 | 2 | 2 | 6 |
| Left knee | 1 | 2 | 2 | 1 | 0 | 5 |
| Right hip | 0 | 0 | 0 | 0 | 0 | 0 |
| Left hip | 0 | 0 | 0 | 1 | 1 | 2 |

FIG. 45

|  | Placebo (n = 83) | Fasinumab | | | |
|---|---|---|---|---|---|
|  |  | 1 mg (n = 85) | 3 mg (n = 84) | 6 mg (n = 85) | 9 mg (n = 84) |
| Baseline | | | | | |
| n | 83 | 85 | 84 | 85 | 84 |
| Mean (SD) | 6.2 (2.0) | 6.1 (2.0) | 6.1 (1.6) | 5.9 (1.8) | 6.2 (1.7) |
| Median (range) | 6.3 | 6.1 | 6.2 | 6.3 | 6.4 |
|  | (1.3, 9.6) | (1.6, 9.4) | (2.8, 9.9) | (1.3, 9.5) | (2.5, 9.9) |
| Week 16 | | | | | |
| n | 70 | 75 | 78 | 76 | 80 |
| Mean (SD) | 4.0 (2.6) | 2.9 (2.3) | 2.7 (2.3) | 3.01 (2.3) | 2.7 (2.4) |
| Median (range) | 3.9 | 2.5 | 2.4 | 2.4 | 2.1 |
|  | (0.0, 8.6) | (0.0, 9.0) | (0.0, 7.8) | (0.0, 8.0) | (0.0, 9.1) |
| Change from Baseline | | | | | |
| n | 70 | 75 | 78 | 76 | 80 |
| Mean (SD) | -2.1 | -3.2 | -3.3 | -3.0 | -3.5 |
|  | (2.3) | (2.3) | (2.3) | (2.5) | (2.5) |
| Median (range) | -1.6 | -3.2 | -3.4 | -3.1 | -3.1 |
|  | (-8.5, 2.2) | (-7.9, 3.5) | (-8.1, 3.5) | (-7.8, 2.8) | (-8.8, 2.5) |
| LS Mean (SE) | -2.0 | -3.1 | -3.3 | -3.0 | -3.4 |
|  | (0.3) | (0.3) | (0.3) | (0.3) | (0.3) |
| 95% CI | -2.5, -1.4 | -3.6, -2.6 | -3.8, -2.7 | -3.6, -2.5 | -4.0, -2.9 |
| Difference vs placebo | | | | | |
| LS Mean (SE) | — | -1.1 (0.4) | -1.3 (0.4) | -1.1 (0.4) | -1.4 (0.4) |
| 95% CI | — | -1.8, -0.4 | -2.0, -0.6 | -1.8, -0.4 | -2.1, -0.7 |
| P value |  | 0.0019 | 0.0003 | 0.0029 | <0.0001 |

FIG. 48

| | Placebo (n = 83) | Fasinumab | | | |
|---|---|---|---|---|---|
| | | 1 mg (n = 85) | 3 mg (n = 84) | 6 mg (n = 85) | 9 mg (n = 84) |
| Baseline | | | | | |
| n | 83 | 85 | 84 | 85 | 84 |
| Mean (SD) | 0.55(0.21) | 0.51(0.22) | 0.56(0.18) | 0.57(0.18) | 0.55(0.19) |
| Median (range) | 0.60(0.01, 1.0) | 0.56(0.01, 0.80) | 0.62(0.02, 0.88) | 0.64(0.04, 0.91) | 0.58(0.18, 1.0) |
| Week 16 | | | | | |
| n | 71 | 75 | 78 | 77 | 80 |
| Mean (SD) | 0.66 (0.20) | 0.70 (0.20) | 0.70 (0.1976) | 0.72 (0.17) | 0.73 (0.17) |
| Median (range) | 0.70 (0.02, 1.0) | 0.710 (-0.05, 1.00) | 0.74 (-0.22, 1.00) | 0.74 (0.16, 1.00) | 0.74 (0.62, 0.84) |
| Change from baseline | | | | | |
| n | 71 | 75 | 78 | 77 | 80 |
| Mean (SD) | 0.11 (0.22) | 0.19 (0.24) | 0.11 (0.19) | 0.15 (0.21) | 0.17 (0.20) |
| Median (range) | 0.064 (-0.43, 0.76) | 0.139 (-0.43, 0.83) | 0.112 (-0.45, 0.55) | 0.135 (-0.42, 0.93) | 0.13 (-0.25, 0.78) |
| LS Mean (SE) | 0.092 (0.022) | 0.15 (0.02) | 0.122 (0.021) | 0.15 (0.02) | 0.16 (0.02) |
| 95% CI | 0.05, 0.14 | 0.11, 0.20 | 0.08, 0.16 | 0.11, 0.19 | 0.12, 0.20 |
| Difference vs placebo | | | | | |
| LS Mean (SE) | -- | 0.06 (0.03) | 0.03 (0.03) | 0.06 (0.03) | 0.07 (0.03) |
| 95% CI | -- | 0.01, 0.12 | -0.03, 0.09 | 0.00, 0.11 | 0.02, 0.13 |
| P value | -- | 0.03 | 0.30 | 0.04 | 0.01 |

FIG. 49

|  | Placebo (N=83) | Fasinumab | | | |
|---|---|---|---|---|---|
|  |  | 1 mg (N=85) | 3 mg (N=84) | 6 mg (N=85) | 9 mg (N=84) |
| Baseline | | | | | |
| N | 83 | 85 | 84 | 85 | 84 |
| Mean (SD) | 6.15 (1.856) | 6.11 (2.017) | 6.09 (1.626) | 5.94 (1.762) | 6.20 (1.708) |
| Median | 6.30 | 6.10 | 6.15 | 6.30 | 6.35 |
| Q1 : Q3 | 4.8 : 7.6 | 4.9 : 7.7 | 4.9 : 7.2 | 4.9 : 7.2 | 4.8 : 7.4 |
| Min : Max | 1.3 : 9.6 | 1.6 : 9.4 | 2.8 : 9.9 | 1.3 : 9.5 | 2.5 : 9.9 |
| Week 16 | | | | | |
| N | 70 | 75 | 78 | 76 | 80 |
| Mean (SD) | 4.03 (2.561) | 2.92 (2.267) | 2.73 (2.277) | 3.01 (2.307) | 2.65 (2.404) |
| Median | 3.90 | 2.50 | 2.35 | 2.40 | 2.10 |
| Q1 : Q3 | 1.8 : 6.3 | 0.9 : 4.4 | 0.8 : 4.1 | 1.2 : 5.0 | 0.4 : 4.6 |
| Min : Max | 0.0 : 8.6 | 0.0 : 9.0 | 0.0 : 7.8 | 0.0 : 8.0 | 0.0 : 9.1 |
| Change from Baseline | | | | | |
| N | 70 | 75 | 78 | 76 | 80 |
| Mean (SD) | -2.12 (2.258) | -3.21 (2.229) | -3.28 (2.291) | -2.97 (2.447) | -3.51 (2.498) |
| Median | -1.60 | -3.20 | -3.40 | -3.10 | -3.10 |
| Q1 : Q3 | -3.7 : -0.2 | -4.7 : -1.7 | -5.0 : -1.7 | -4.7 : -1.0 | -5.7 : -2.0 |
| Min : Max | -8.5 : 2.2 | -7.9 : 3.5 | -8.1 : 3.5 | -7.8 : 2.8 | -8.8 : 2.5 |
| LS Mean (SE) | -1.98 (0.280) | -3.08 (0.272) | -3.27 (0.272) | -3.03 (0.270) | -3.41 (0.271) |
| 95% CI | (-2.53, -1.43) | (-3.62, -2.55) | (-3.81, -2.74) | (-3.57, -2.50) | (-3.95, -2.88) |
| Difference vs. Placebo | | | | | |
| LS Mean (SE) |  | -1.10 (0.352) | -1.29 (0.351) | -1.06 (0.352) | -1.43 (0.351) |
| 95% CI |  | (-1.79, -0.41) | (-1.98, -0.60) | (-1.75, -0.36) | (-2.12, -0.74) |
| P-value |  | 0.0019 | 0.0003 | 0.0029 | <.0001 |

FIG. 52

PHARMACEUTICAL COMPOSITION FOR SAFE AND EFFECTIVE TREATMENT OF KNEE AND/OR HIP PAIN

FIELD OF THE INVENTION

The present invention relates to the treatment, or prevention of pain in joints such as the knee joint or the hip joint in patients who have a history of inadequate pain relief, or intolerance to standard analgesic therapy. More specifically, the invention relates to the administration of NGF antagonists, in particular a nerve growth factor (NGF) antibody, to reduce knee and/or hip pain in a patient in need thereof.

BACKGROUND

Many patients with acute and chronic pain do not receive adequate pain relief despite the wide variety of analgesic medications that are currently available, either because the medications are not effective in all patients, or because their use is limited by toxicity or intolerability. The limitations of currently available analgesic therapies include adverse central nervous system effects, nausea and vomiting, constipation, gastrointestinal bleeding and ulceration, cardiovascular events, renal toxicity, and potential for abuse. Inadequate pain relief has a profound impact on the quality of life for millions of people worldwide with an associated substantial cost to society, including healthcare cost and loss of productivity.

Neurotrophins are a family of peptide growth factors that play a role in the development, differentiation, survival and death of neuronal and non-neuronal cells (Chao, M. et.al., (2006), ClinSci (Lond); 110:167). In the adult, NGF is not required as a survival factor but acts as a pain mediator that sensitizes neurons (Pezet, S. et.al., (2006), Ann Rev Neurosci 29:507-518). Nerve growth factor activity is mediated through 2 different membrane-bound receptors, the high-affinity tyrosine kinase type 1 (TrkA) and the low-affinity p75 neurotrophin receptors.

Administration of NGF has been shown to provoke pain in both rodents (Lewin, G. R., et.al., (1994), Eur. J. Neurosci 6:1903-1912) and humans (McArthur, J. C., et.al., (2000), Neurology 54:1080-1088), while NGF antagonists have been shown to prevent hyperalgesia and allodynia in animal models of neuropathic and chronic inflammatory pain (Ramer, M. S. et.al., (1999) Eur J Neurosci 11:837-846). Humans with mutations in TrkA (hereditary sensory and autonomic neuropathy IV) or NGF (hereditary sensory and autonomic neuropathy V) have been identified with a loss of deep pain perception (Indo, Y. et.al., (1996), Nature Genetics, 13:485-488), Einarsdottir, E., et.al., (2004), Human Molecular Genetics 13:799-805). In addition, NGF is known to be elevated in the synovial fluid of patients with rheumatoid arthritis and other types of arthritis (Aloe, L. et.al., (1992), Arthritis Rheum 35:351-355; Halliday, D. A., (1998), Neurochem Res. 23:919-922), and to be up-regulated in injured and inflamed tissues in conditions such as cystitis, prostatitis, and chronic headache (Lowe, E. M., et.al., (1997), Br. J. Urol. 79:572-577; Miller, L. J., et.al., (2002), Urology 59:603-608; Sarchielli, P. et.al., (2001), Neurology 57:132-134).

There is an unmet need for agents that alleviate pain in individuals who have a history of inadequate pain relief, or who are intolerant to standard analgesic therapy. Fasinumab is a fully-human high-affinity monoclonal antibody directed against NGF (see U.S. Pat. No. 7,988,967 and PCT Publication No. WO 2009/023540 and WHO Drug Information Vol. 26, No. 2, (2012), which are all hereby incorporated by reference in their entirety). By selectively blocking NGF, fasinumab has the potential to be effective in modulating NGF-associated pain without some of the adverse side effects of other analgesic medications, such as opioids and non-steroidal anti-inflammatory drugs (NSAIDs).

BRIEF SUMMARY OF THE INVENTION

A pharmaceutical composition and a method for treating knee and/or hip pain in a patient non-responsive or intolerant to standard analgesic therapy are disclosed. A pharmaceutical composition and a method for reducing risk for developing an arthropathy in a subject receiving an anti-NGF antibody for treatment of knee and/or hip pain are disclosed. Also provided herein are methods for monitoring safety of a treatment of knee and/or hip pain involving administration of an anti-NGF antibody. In certain aspects, the subject has osteoarthritis of the knee and/or hip and the anti-NGF antibody is fasinumab.

In certain aspects, a pharmaceutical composition for use in treatment of a subject having pain in the knee joint or the hip joint, where the subject is non-responsive to analgesic treatment or suffers from side-effects from analgesic treatment is disclosed. The composition comprises a therapeutically effective amount of an antibody that binds specifically to nerve growth factor (NGF) or an antigen binding fragment thereof. The composition is used in the absence of an analgesic treatment to relieve pain.

In another aspect of the invention the use includes any of the above uses wherein the antibody or antigen-binding fragment thereof that binds specifically to NGF is administered to the patient at a dose of about 1 mg to about 9 mg. The frequency of administration is about every 4 weeks.

In another aspect of the invention the use includes any of the above uses wherein the analgesic treatment includes acetaminophen, opioids, nonsteroidal anti-inflammatory drugs (NSAIDs), or a combination thereof.

A pharmaceutical composition for avoidance of an arthropathy associated with treatment with an anti-nerve growth factor (NGF) antibody that binds specifically to NGF or an antigen binding fragment thereof is disclosed. In certain aspects, the composition is formulated as a dose of less than 9 mg of the anti-NGF antibody or the antigen binding fragment thereof. In certain aspects, the composition is formulated as a dose of less than 6 mg of the anti-NGF antibody or the antigen binding fragment thereof. In certain aspects, the initial dose and the one or more secondary doses of the pharmaceutical composition that reduces risk of development of an arthropathy each comprise about 1 mg, about 2 mg, about 3 mg, about 4 mg, or about 5 mg of the anti-NGF antibody or the antigen binding fragment thereof. In certain aspects, the initial dose and the one or more secondary doses of the pharmaceutical composition that reduces risk of development of an arthropathy each comprise about 1 mg or about 3 mg of the anti-NGF antibody or the antigen binding fragment thereof. In certain aspects, the arthropathy includes joint space narrowing exceeding pre-specified thresholds. In certain aspects, the arthropathy includes changes in bone structure evident on plain film. In certain aspects, the arthropathy includes changes in bone structure evident on plain film, joint space narrowing exceeding pre-specified thresholds, or both, in a knee joint. In certain aspects, the arthropathy includes changes in bone structure evident on plain film, joint space narrowing exceeding pre-specified thresholds, or both, in a hip joint. In certain aspects, the frequency of administration of a dose of the anti-NGF antibody that reduces risk of developing at least one arthropathy is about every 4 weeks.

In certain aspects of the invention, the subject being treated with the compositions and methods disclosed herein is diagnosed with osteoarthritis of the knee and/or the hip.

In another aspect of the invention the use includes any of the above uses wherein a patient which exhibits a history of inadequate pain relief from, or is resistant, inadequately responsive, or intolerant to standard analgesic therapy.

In another aspect of the invention the use includes any of the above uses wherein a patient is unwilling to take standard analgesic therapy or does not have access to standard analgesic therapy.

In another aspect of the invention the use includes any of the above uses wherein a situation wherein standard analgesic therapy is inadvisable for administration to the patient due to safety and health risks to the patient and/or coupled with suboptimal efficacy. In another aspect of the invention the use includes any of the above uses wherein a situation wherein the standard analgesic therapy is inadvisable for administration to the patient due to a condition selected from the group consisting of medical contraindications, hypersensitivity to standard analgesic therapy, or excipients, use of a concomitant medication prohibited with standard analgesic therapy, increased risk of kidney damage, increased risk of liver damage, increased risk of gastrointestinal bleeding, increased risk of an allergic reaction and increased risk of developing drug dependence.

In another aspect of the invention the use includes any of the above uses wherein the standard analgesic therapy is selected from the group consisting of paracetamol/acetaminophen, a non-steroidal anti-inflammatory (NSAID), and an opioid.

In another aspect of the invention the use includes any of the above uses wherein the opioid is selected from the group consisting of hydrocodone, oxycodone, percocet, morphine, meperidine, hydromorphone, fentanyl, and methadone.

In another aspect of the invention the use includes any of the above uses wherein the antibody or antigen-binding fragment thereof that binds specifically to NGF is administered to the patient at a frequency of about every 4 weeks.

In another aspect of the invention the use includes any of the above uses wherein the antibody or antigen-binding fragment is administered subcutaneously (SC), or intravenously (IV).

In another aspect of the invention the use includes any of the above uses wherein the anti-NGF antibody comprises three heavy chain complementarity determining region (HCDR) sequences (HCDR1, HCDR2, HCDR3) comprising SEQ ID NOs: 4, 6 and 8, respectively, and three light chain complementarity determining (LCDR) sequences (LCDR1, LCDR2, LCDR3) comprising SEQ ID NOs: 12, 14 and 16, respectively.

In another aspect of the invention the use includes any of the above uses wherein the antibody comprises an HCVR having the amino acid sequence of SEQ ID NO:2.

In another aspect of the invention the use includes any of the above uses wherein the antibody comprises an LCVR having the amino acid sequence of SEQ ID NO: 10.

In another aspect of the invention the use includes any of the above uses wherein the antibody is fasinumab.

In another aspect of the invention the use includes any of the above uses wherein the initial dose and the one or more secondary doses are administered either subcutaneously or intravenously.

In another aspect of the invention the use includes any of the above uses wherein the one or more secondary doses of the anti-NGF antibody are administered every four weeks, every eight weeks, or every 12 weeks after the initial dose.

In another aspect of the invention the use includes any of the above uses wherein the use results in improvement in one or more pain-associated parameters. In certain aspects, the pain-associated parameter is selected from the group consisting of: (a) a change from baseline at week 16 in Western Ontario and McMaster Universities Osteoarthritis Index (WOMAC) pain score; (b) a change from baseline at week 16 in the physical function subscale scores; and (c) a change from baseline at week 16 in the Patient Global Assessment (PGA).

In another aspect of the invention the use includes any of the above uses wherein the use results in an improvement in daily and weekly (average of daily scores over the preceding week) walking index joint pain score on the Numeric Rating Scale (NRS; scale 0-10; 0=no pain; MCID: ~1 point).

In another aspect of the invention the use includes any of the above uses wherein the use results in an improvement in the rate of response using the Outcome Measures for Rheumatology Committee and Osteoarthritis Research Society International Standing Committee for Clinical Trials Response Criteria Initiative (OMERACT-OARSI) responder index (an 11-item tool that measures knee or hip osteoarthritis pain).

In another aspect of the invention the use includes any of the above uses wherein the use results in an improvement in quality of life assessed using the short form-36 (SF-36) health survey and EuroQol-5 Dimension-5 Level (EQ-5D-5L) scale utility index score.

In another aspect of the invention the use includes any of the above uses wherein the use provides a relief from pain associated with knee or hip joint for a period of up to 36 weeks from the start of the use.

Each of the above aspects of the invention are also disclosed and described herein as corresponding methods of treatment.

In certain aspects, a method for monitoring treatment of a subject having pain in the knee joint or the hip joint is provided. The method includes administering a pharmaceutical composition comprising a dose of about 9 mg of an anti-NGF antibody that specifically binds to NGF or an antigen binding fragment thereof; monitoring a knee joint or a hip joint of the subject to determine whether the subject has developed an arthropathy; wherein if the subject has developed arthropathy, administering a pharmaceutical composition comprising a dose of less than about 9 mg of the antibody or the antigen binding fragment thereof to the subject; or wherein if the subject has not developed arthropathy, administering a pharmaceutical composition comprising a dose of about 9 mg of the antibody or the antigen binding fragment thereof to the subject.

In certain aspects of the method of monitoring, if the subject has developed arthropathy, the subsequent treatment comprises administering a pharmaceutical composition comprising about 1.0 mg to about less than 6 mg of the anti-NGF antibody or an antigen binding fragment thereof, wherein the treatment reduces pain in the knee joint or the hip joint and reduces arthropathy.

In certain aspects of the method of monitoring, the antibody comprises three heavy chain complementarity determining region (HCDR) sequences (HCDR1, HCDR2, HCDR3) comprising SEQ ID NOs: 4, 6 and 8, respectively, and three light chain complementarity determining (LCDR) sequences (LCDR1, LCDR2, LCDR3) comprising SEQ ID NOs: 12, 14 and 16, respectively.

In certain aspects of the method of monitoring, the antibody comprises an HCVR having the amino acid sequence of SEQ ID NO:2.

In certain aspects of the method of monitoring, the antibody comprises an LCVR having the amino acid sequence of SEQ ID NO: 10.

In certain aspects of the method of monitoring, the antibody is fasinumab.

BRIEF DESCRIPTION OF THE FIGURES

Figure 2:
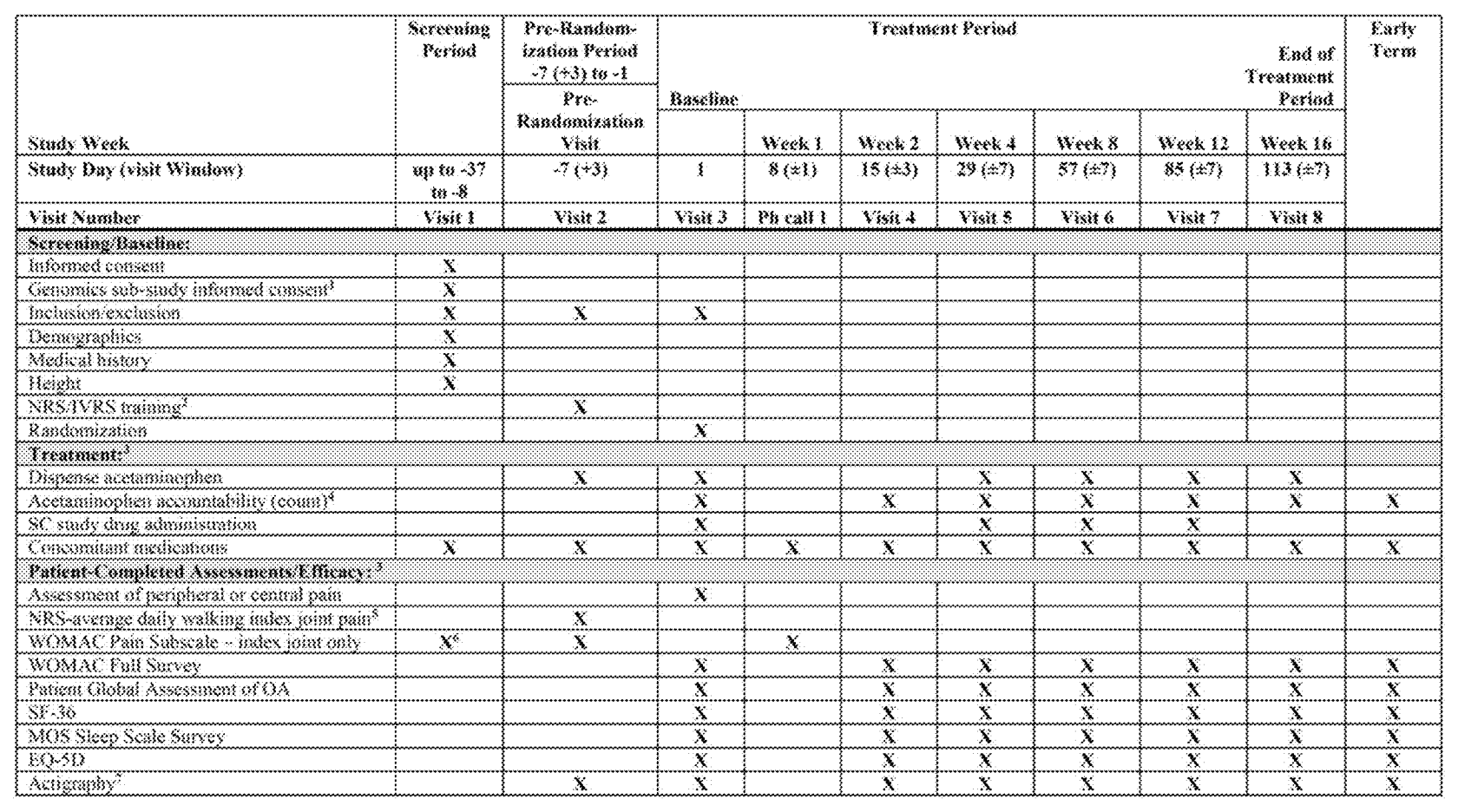
Figure 2:
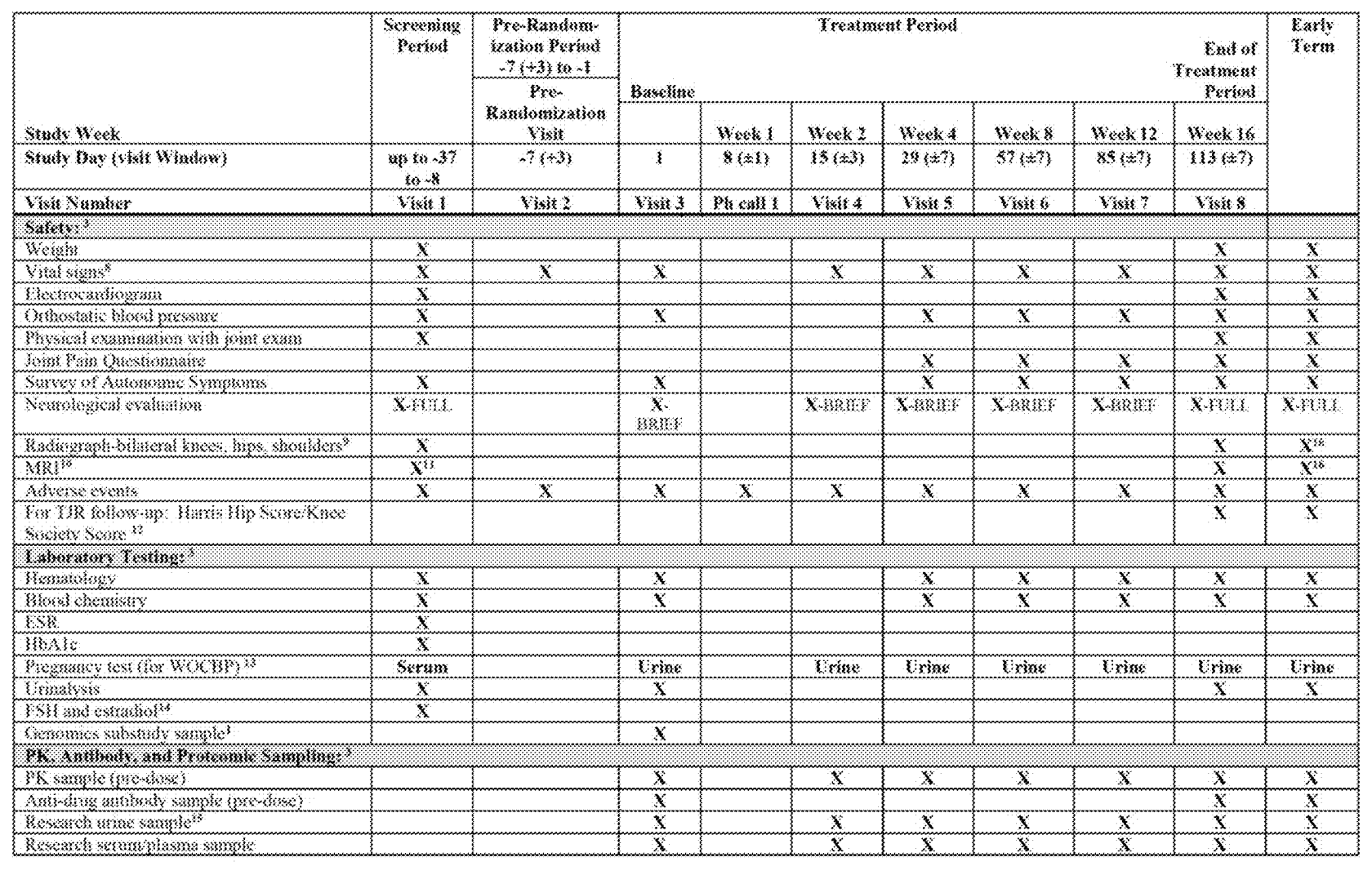

FIG. 2 shows a table of the schedule of events for screening and treatment periods. WOCBP=women of childbearing potential 1. Only for patients who provided written informed consent for the optional genomics sub-study. The sample should have been collected at the baseline visit, but may have been collected at any visit during the study. 2. Patients were trained on using the IVRS after initial patient eligibility had been confirmed during the screening period. Patients used the IVRS to report daily NRS walking index joint pain score and daily use of acetaminophen through the week 20 visit. 3. Study drug administration was the last procedure at each dosing visit, and was done after all laboratory samples had been collected and all study assessments and procedures were performed. Patients were observed in the clinic for 1 hour after study drug was administered. 4. Acetaminophen usage was confirmed by tablet count. 5. Walking index joint pain NRS score was recorded into the electronic case report form (eCRF) by the site at the pre-randomization visit, and by the patient each day (at approximately 6:00 PM) using the IVRS, starting during the pre-randomization period through week 20. 6. At the screening visit, the WOMAC pain sub-scale was evaluated for both knees and both hip joints 7. Patients were provided with an activity monitor (actigraph) at the pre-randomization visit and were trained on its use. Patients wore the monitor for the 7 days prior to each clinic visit starting the day of the pre-randomization visit through week 20. Patients brought the monitor with them to each clinic visit to have the information downloaded by the clinic staff. 8. If the pulse was less than 45 bpm, an ECG with rhythm strip was obtained to confirm the heart rate and rhythm. 9. In addition to scheduled imaging, radiographs should have been considered for worsening joint pain despite treatment with analgesics, which in the opinion of the investigator was inconsistent with the normal progression of OA and lasted at least 2 weeks (or less at the discretion of the investigator). 10. In addition to scheduled MRIs, an MRI should have been considered for worsening joint pain despite treatment with analgesics, which in the opinion of the investigator was inconsistent with the normal progression of OA, lasted at least 2 weeks (or less at the discretion of the investigator), and where the X-rays were inconclusive. 11. After the patient had otherwise met study eligibility criteria assessed during the screening period, an MRI of the index joint, contralateral joint, and any other knee or hip joint that had a baseline K-L score of ≥3 was performed prior to the pre-randomization visit. In cases where the contralateral joint had previously been treated with TJR surgery, an MRI was not required. Confirmation that the image had been accepted and confirmed query-free by the central reader must have been received by the site before the pre-randomization visit. Confirmation that there are no exclusionary findings on the MRI must have been received from the central reader before a patient could be randomized 12. In the event that a patient must undergo TJR surgery during the study, the patient completed the early termination visit and the procedures outlined in the schedule of events for TJR follow-up. The early termination visit should have been completed before TJR surgery if at all possible. 13. In the event of a positive urine pregnancy test result, a serum pregnancy test should have been obtained. If the serum pregnancy test was negative, the patient continued study participation. If the serum pregnancy test was positive, the patient was withdrawn from study drug and was asked to return to the clinic for all remaining study visits per the visit schedule. 14. Test only to be performed if postmenopausal status had to be assessed for female patients ≤59 years of age. 15. The second morning void of urine should have been collected after an overnight fast. This was done either at home prior to the visit or at the study site on the day of the visit. 16. Early Termination: Imaging assessments (X-rays of the knees, hips, and shoulders, and MRIs) were repeated only if it had been >30 days since the joint was last imaged. If it had been ≤30 days since imaging assessments were completed, imaging assessments were completed at the discretion of the investigator.

FIG. 3 shows a table of the schedule of events for a follow-up period. 1. Acetaminophen usage was confirmed by tablet counts.2. Walking index joint pain NRS score was recorded by the patient each day (at approximately 6:00 PM), using the IVRS, through week 20.3. Patients wore the monitor for the 7 days prior to each clinic visit through week 20. Patients brought the monitor to the clinic visit at week 20 to have the information downloaded by the clinic staff. 4. If the pulse was less than 45 bpm, an ECG with rhythm strip was obtained to confirm the heart rate and rhythm. 5. Joint exam only. 6. The questionnaires were completed by the patient at the site during the clinic visits; for telephone visits, the sites documented the information during the telephone calls. 7. In addition to scheduled imaging, radiographs should have been considered for worsening joint pain despite treatment with analgesics, which in the opinion of the investigator was inconsistent with the normal progression of OA and lasted at least 2 weeks (or less at the discretion of the investigator). 8. An MRI of the index joint, contralateral joint, and any other knee or hip that had a baseline K-L score of ≥3 was performed. In cases where the contralateral joint had previously been treated with TJR surgery, an MRI was not required. 9. In the event that a patient underwent TJR surgery during the study, the patient completed the early termination visit and the procedures outlined in the schedule of events for TJR follow-up. The early termination visit should have been completed before TJR surgery if at all possible. 10. Early Termination: Imaging assessments (X-rays of the knees, hips, and shoulders, and MRI) were repeated only if it had been >30 days since the joint was last imaged. If it had been ≤30 days since imaging assessments were completed, imaging assessments were completed at the discretion of the investigator.

FIG. 4 shows a table of the schedule of events to be followed in the event of total joint replacement surgery and follow-up. 1. Any patient who had TJR surgery during the study was asked to return to the site at 4 and 20 weeks after the surgery date for safety evaluations. Relevant information related to the surgery was collected at the week 4 visit, including placement of the prosthesis and healing of the surgical wound. The visit at 20 weeks after surgery included an assessment of OA progression (including repeat radiographs of knees, hips, and shoulders) and the collection of any information about joint-related pain or AEs (including TJRs) that may have taken place since the last clinic visit. 2. Formal post-operative assessment of joint replacements was done by completing the Knee Society Score questionnaire for knee replacements or the Harris Hip Score questionnaire for hip replacements. Full details of these assessments are provided in the study reference manual. 3. MRI was done for the index joint, contralateral joint, and any knee or hip joint that had a baseline K-L score of ≥3. In cases where the contralateral joint had previously been treated with TJR surgery, an MRI was not required.

FIG. 5 shows a summary of patient disposition (full analysis set). SAF=safety analysis set which includes all randomized subjects who received any study drug on day 1. FAS=full analysis set which includes all randomized subjects.

FIG. 6 shows a summary of protocol deviations (full analysis set). IVR=Interactive Voice Response.

FIG. 7 shows a summary of protocol deviations leading to exclusion from per protocol set (full analysis set). IVR=Interactive Voice Response; PPS=Per Protocol Set.

FIG. 8 shows a summary of study populations. FAS=Full Analysis Set; SAF=Safety Analysis Set; PPS=Per Protocol Set.

FIG. 9 shows a summary of baseline demographic characteristics (full analysis set). BMI=Body Mass Index.

FIG. 10 provides a table of medical history and preferred terms reported by ≥10% of patients in any treatment group (full analysis set). Note: The data in this table have been truncated from the source table. MedDRA (Version 18.0) coding dictionary applied. A subject who reported 2 or more medical history findings with the same preferred term is counted only once for that term. A subject who reported 2 or more medical history findings with different preferred terms within the same system organ class is counted only once in that system organ class.

FIG. 11 shows a summary of treatment compliance (safety analysis set).

FIG. 12 shows a summary of change from baseline to week 16 in WOMAC pain score (full analysis set). N=Number of subjects in Full Analysis Set, and n=Number of subjects within a specified category. SD=Standard deviation, Min=Minimum and Max=Maximum. LS Mean=Least squares mean, SE=Standard error of the LS Mean, and CI=Confidence interval. Analyses are based on MMRM model with baseline randomization strata, baseline, treatment, visit and treatment-by-visit interaction.

FIG. 17 shows a summary of change from baseline to week 16 in patient global assessment score (score range: 1 to 5) (full analysis set). N=Number of subjects in Full Analysis Set,¬ and n=Number of subjects within a specified category. SD=Standard deviation,¬ Min=Minimum and Max=Maximum. LS Mean=Least squares mean,¬ SE=Standard error of the LS Mean,¬ and CI=Confidence interval. Analyses are based on MMRM model with baseline randomization strata,¬ baseline,¬ treatment,¬ visit and treatment-by-visit interaction.

FIG. 20 shows the percentage of patients who used rescue medication (full analysis set). [1] Odds ratio is Fasinumab versus Placebo. CI=Confidence interval calculated using normal approximation. [2] P-values were derived by Cochran-Mantel-Haenszel (CMH) test stratified by baseline strata Kellgren-Lawrence category (2-3 vs 4) and Index Joint (knee vs hip).

FIG. 21 shows the duration of exposure to study drug (safety analysis set). [1] Date of last dose–date of first dose+28.

FIG. 22 shows the duration of observation (safety analysis set). [1] Date of last visit (including follow-up visit for TJR)–date of first dose+1.

FIG. 23 shows an overview of treatment-emergent adverse events during the treatment period (safety analysis set). TEAE: Treatment-Emergent Adverse Events. [1] Refers to subjects who permanently discontinued study drug (from AE panel).

FIG. 24 shows an overview of adverse events during the follow-up period (safety analysis set). AE: adverse events.

FIG. 25 shows a summary of treatment-emergent adverse events reported in >3% of patients in any treatment group during treatment period by system organ class and preferred term (safety analysis set). MedDRA (Version 18.0) coding dictionary applied. TEAE: Treatment Emergent Adverse Events. A subject who reported 2 or more TEAEs with the same preferred term is counted only once for that term. A subject who reported 2 or more TEAEs with different preferred terms within the same system organ class is counted only once in that system organ class.

FIG. 26 shows a summary of adverse events reported in >3% of patients in any treatment group during follow-up by preferred term (safety analysis set). AE=Adverse Event MedDRA (Version 18.0) coding dictionary applied. A subject who reported 2 or more AEs with the same preferred term is counted only once for that term. A subject who reported 2 or more AEs with different preferred terms within the same system organ class is counted only once in that system organ class.

FIG. 27 shows a summary of treatment-related treatment-emergent adverse events reported in >2% of patients during treatment period by system organ class and preferred term (safety analysis set). MedDRA (Version 18.0) coding dictionary applied. TEAE: Treatment Emergent Adverse Events. A subject who reported 2 or more TEAEs with the same preferred term is counted only once for that term. A subject who reported 2 or more TEAEs with different preferred terms within the same system organ class is counted only once in that system organ class.

FIG. 28 shows a summary of treatment-related adverse events reported in >2% of patients during follow-up period by system organ class and preferred term (safety analysis set). MedDRA (Version 18.0) coding dictionary applied. AE: Adverse Event. A subject who reported 2 or more AEs with the same preferred term is counted only once for that term. A subject who reported 2 or more AEs with different preferred terms within the same system organ class is counted only once in that system organ class.

FIG. 29 shows a summary of treatment-emergent serious adverse events reported during treatment period by system organ class and preferred term (safety analysis set). MedDRA (Version 18.0) coding dictionary applied. TEAE:

Figure 1:
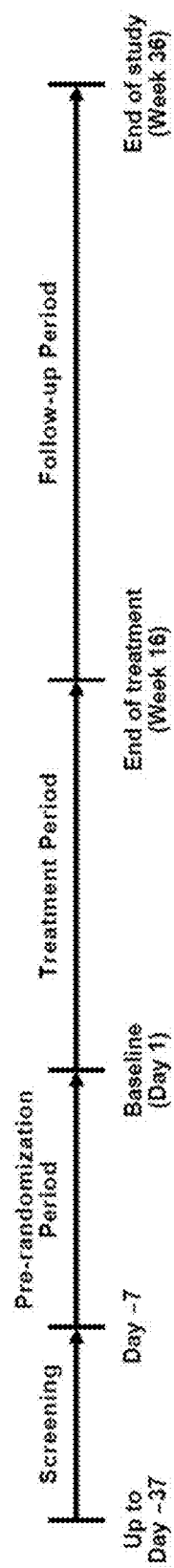
FIG. 1 provides a schematic of the study design.
Figure 13:
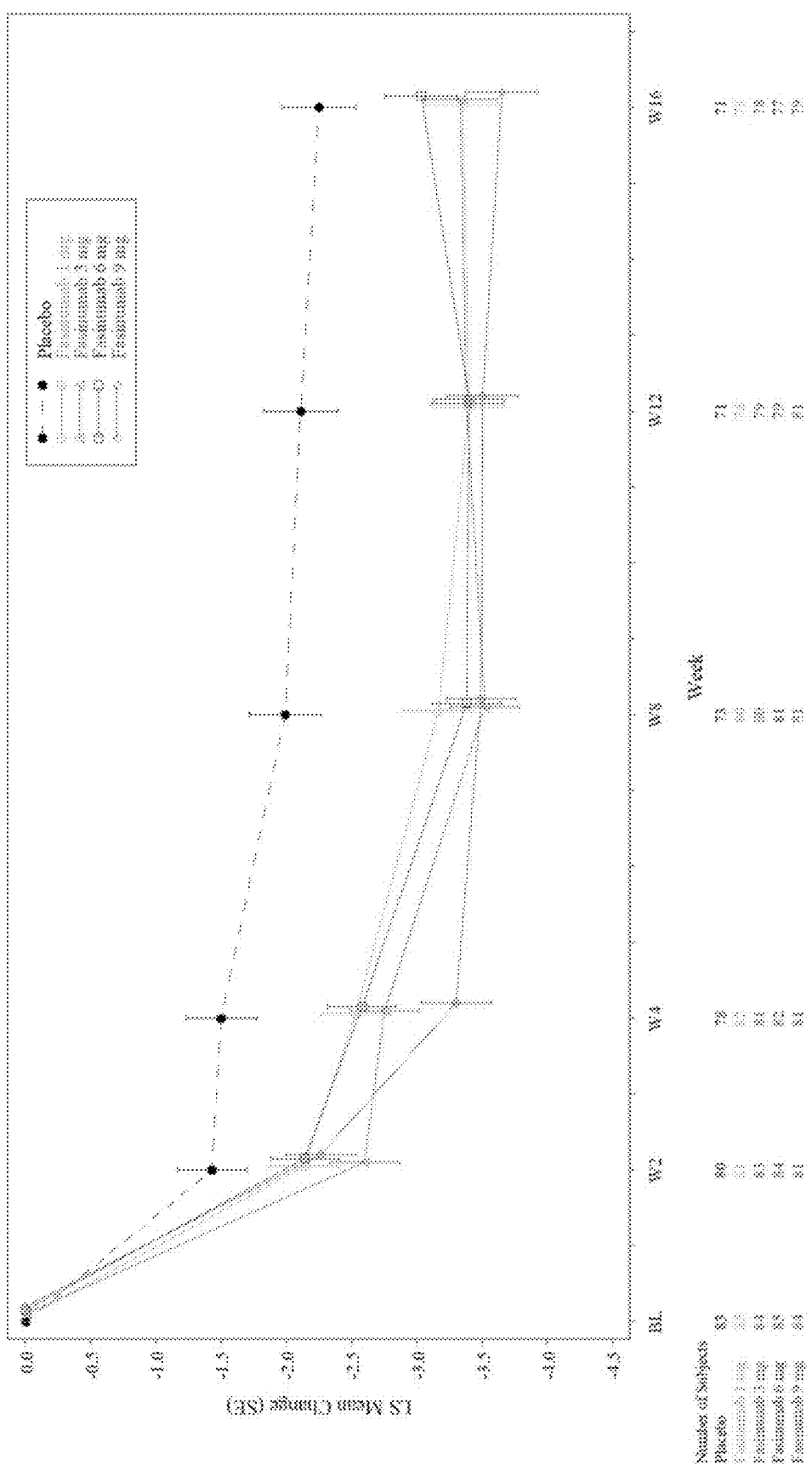
FIG. 13 shows a change from baseline to week 16 in WOMAC pain subscale score by visit: least squares mean (+/−SE) (full analysis set).
Figure 14:
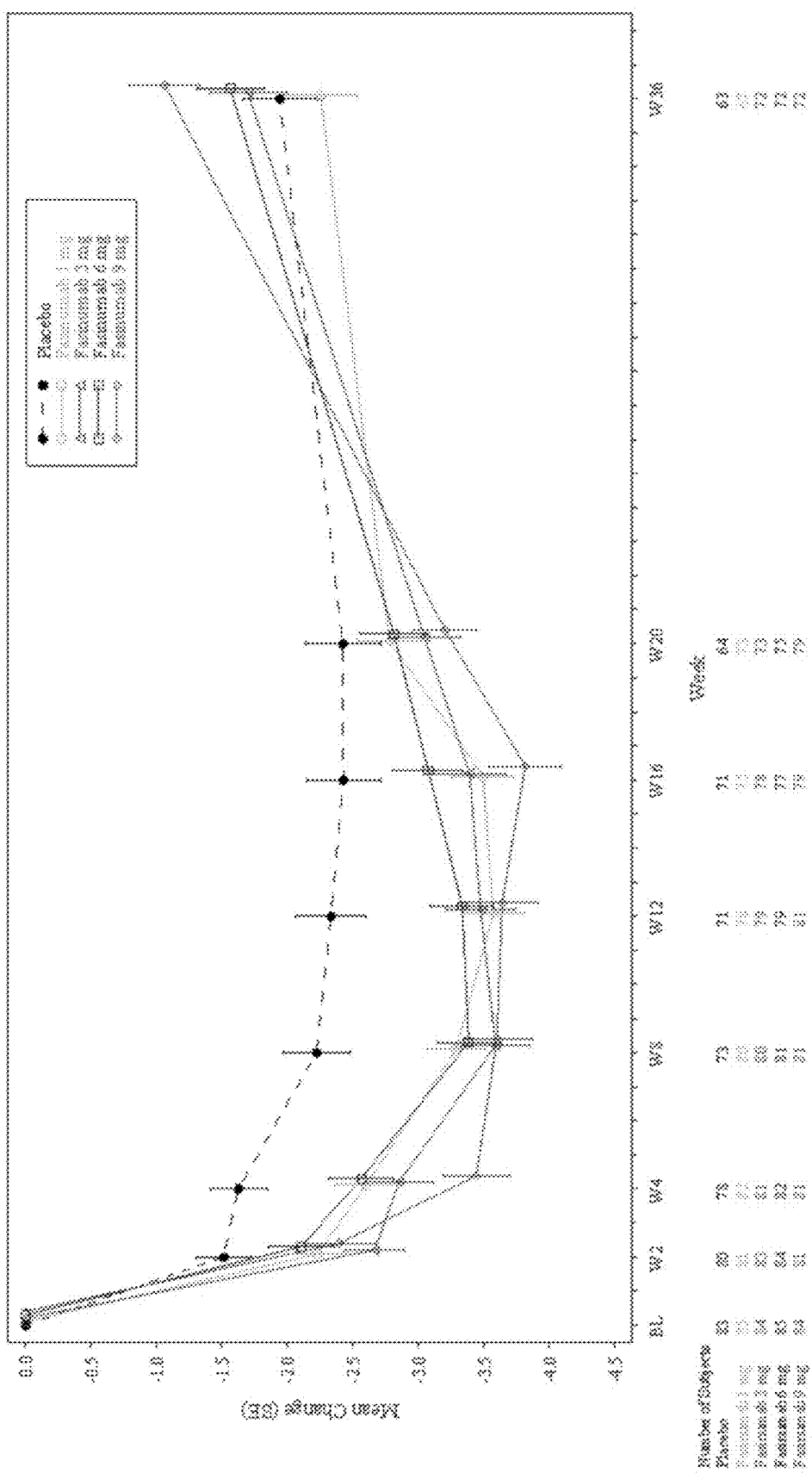
FIG. 14 shows a change from baseline to week 36 in WOMAC pain subscale score by visit: raw mean (+/−SE) (full analysis set).
Figure 15:
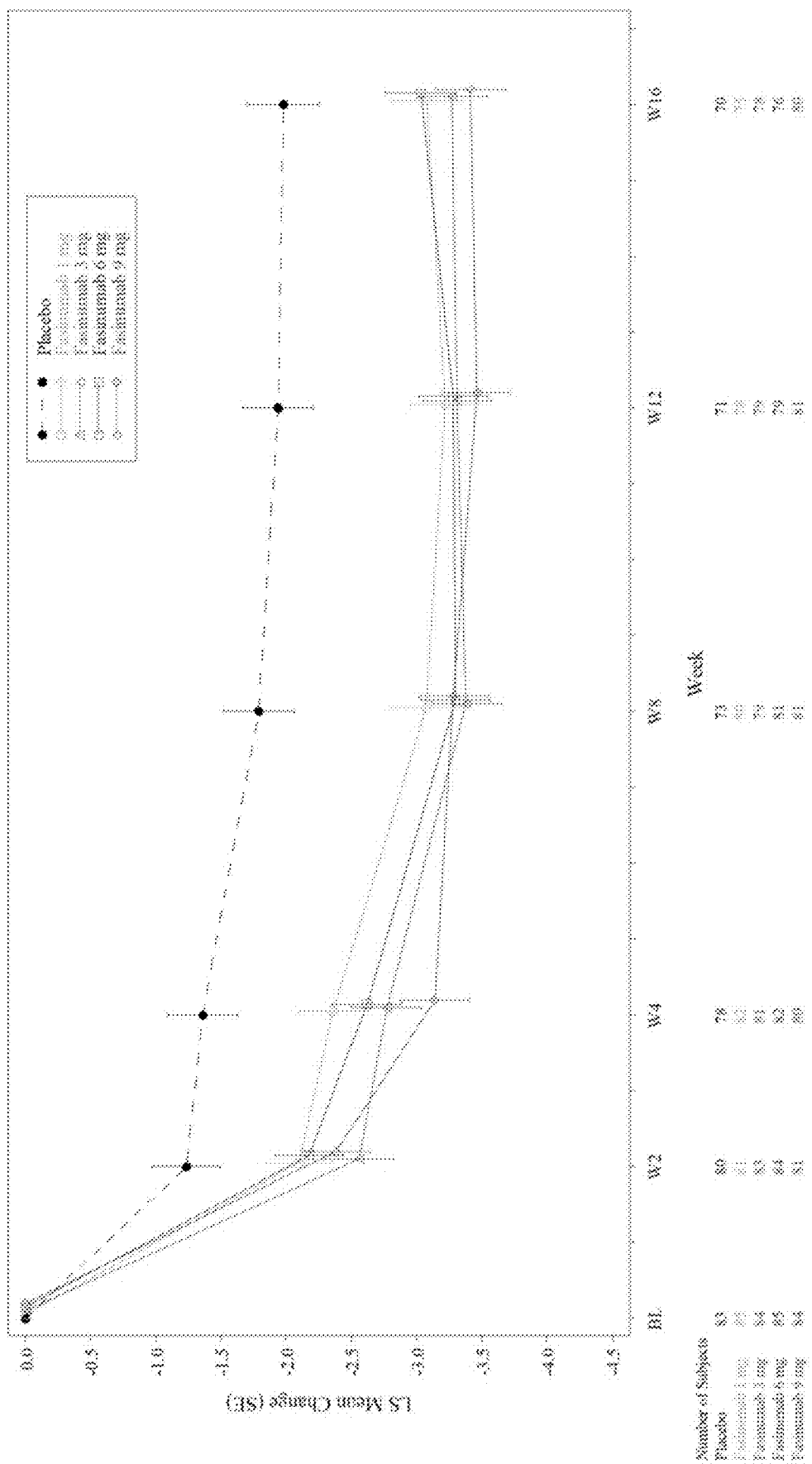
FIG. 15 shows a change from baseline in WOMAC physical function subscale score by visit: least squares mean (+/−SE) (full analysis set).
Figure 16:
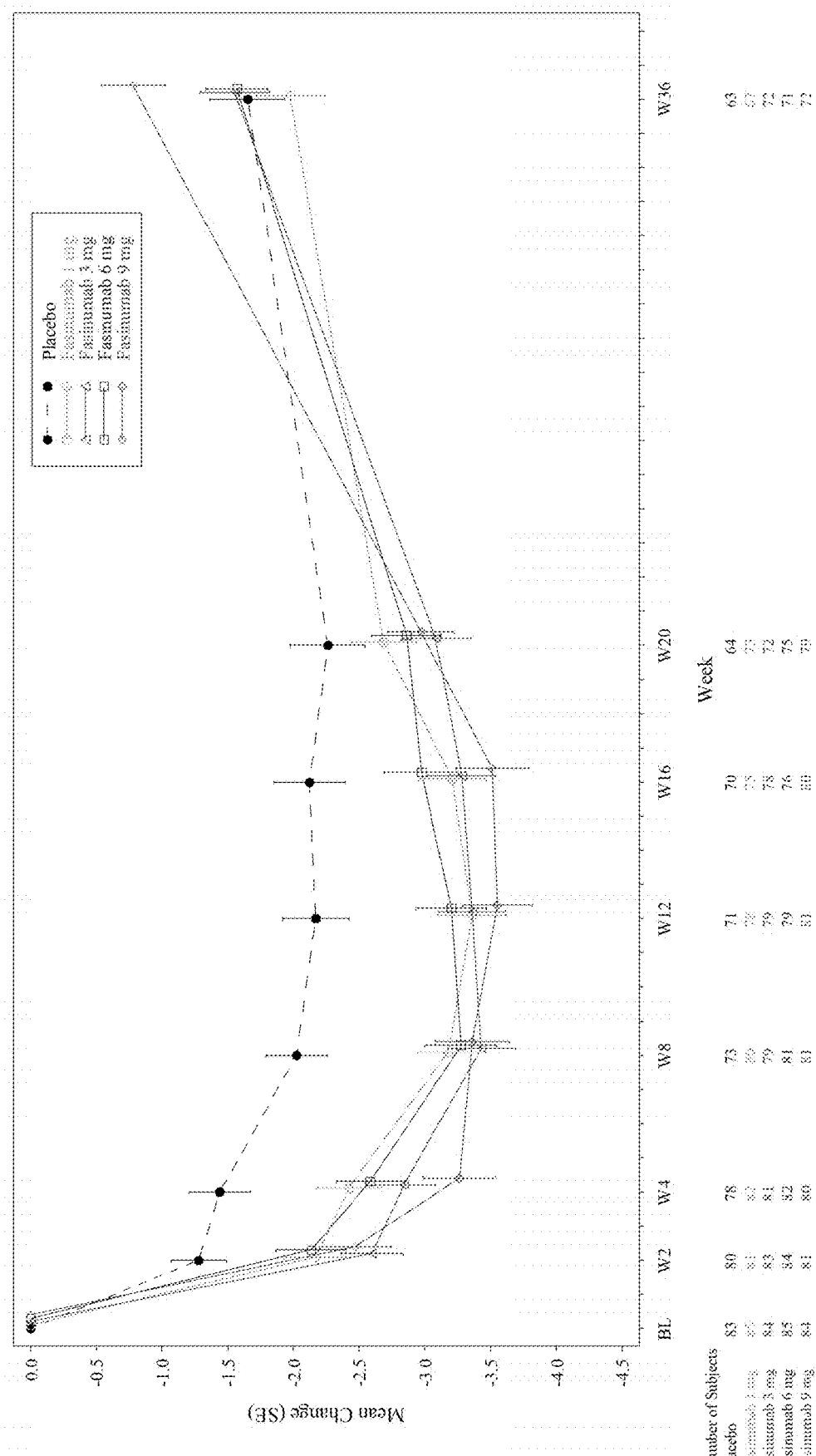
FIG. 16 shows a change from baseline in WOMAC physical function subscale score by visit: mean (+/−SE) (full analysis set).
Figure 18:
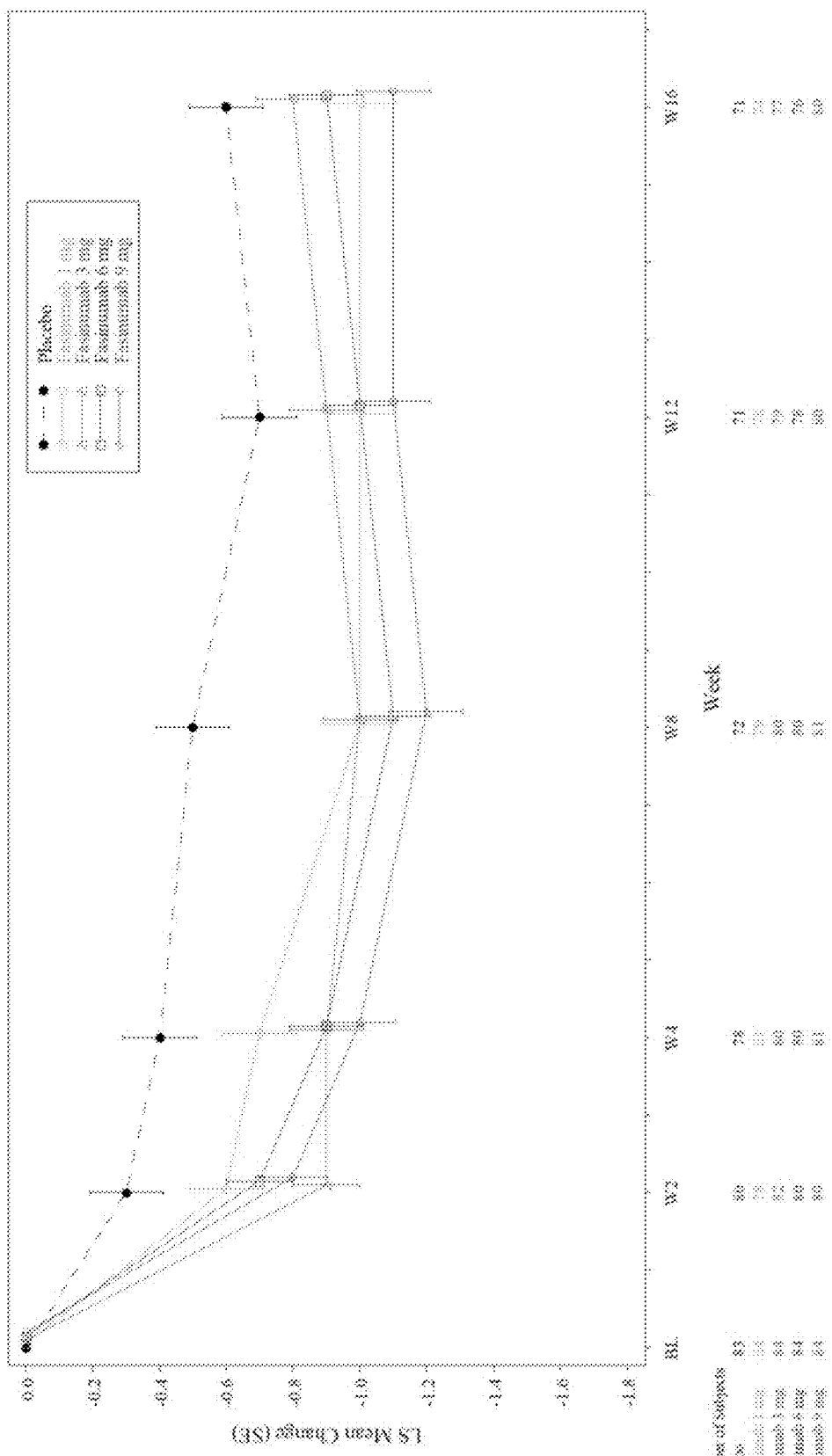
FIG. 18 shows a change from baseline to week 16 in patient global assessment by visit: least squares mean (+/−SE) (full analysis set).
Figure 19:
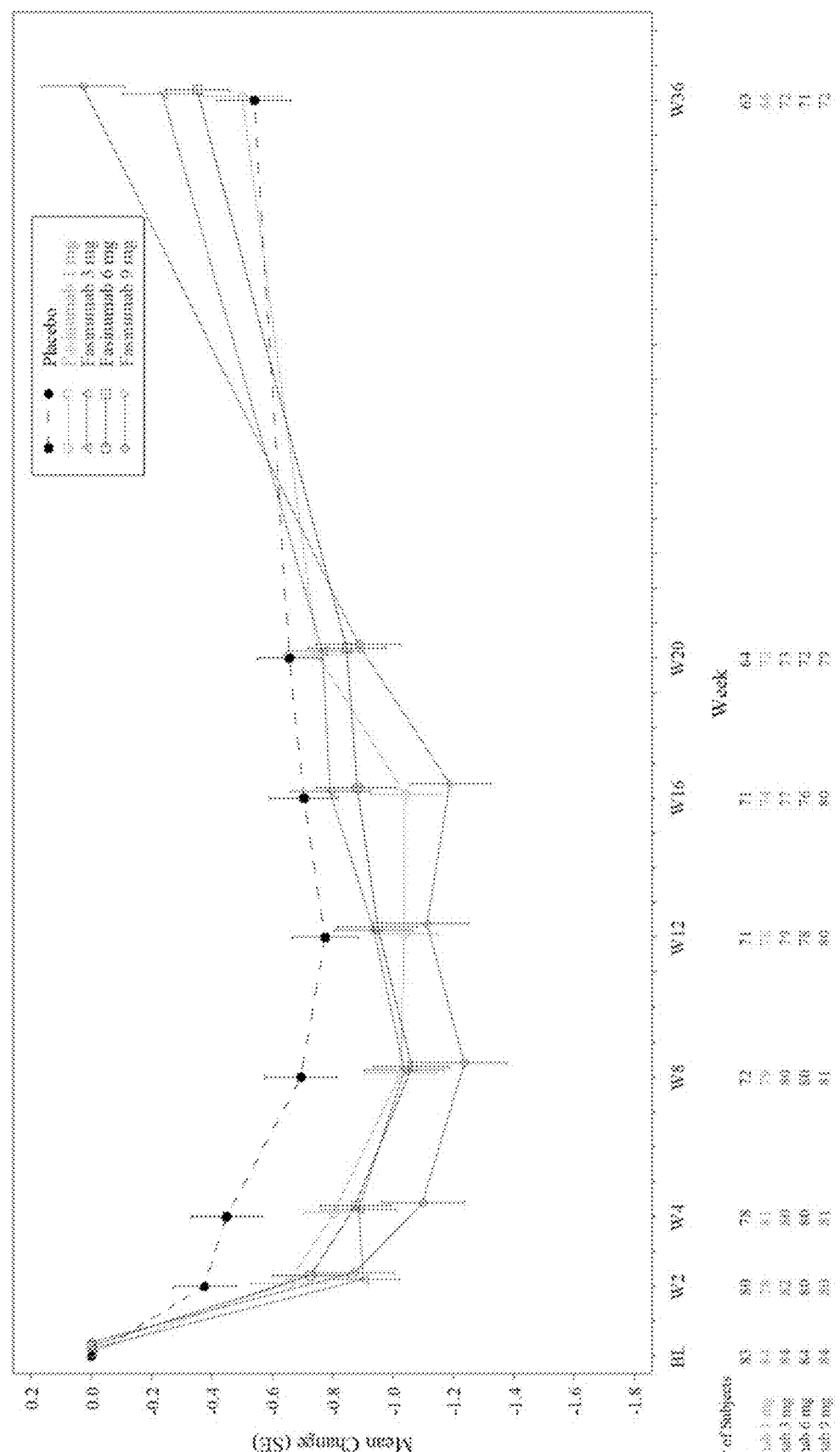
FIG. 19 shows a change from baseline in patient global assessment by visit: mean (+/−SE) (full analysis set).

Treatment Emergent Adverse Events. A subject who reported 2 or more TEAEs with the same preferred term is counted only once for that term. A subject who reported 2 or more TEAEs with different preferred terms within the same system organ class is counted only once in that system organ class.

FIG. 30 shows a summary of adverse events reported during follow-up period by system organ class and preferred term (safety analysis set). MedDRA (Version 18.0) coding dictionary applied. A subject who reported 2 or more TEAEs with the same preferred term is counted only once for that term. A subject who reported 2 or more TEAEs with different preferred terms within the same system organ class is counted only once in that system organ class.

FIG. 31 shows a summary of treatment-emergent adverse events leading to study drug discontinuation by system organ class and preferred term (safety analysis set). MedDRA (Version 18.0) coding dictionary applied. TEAE: Treatment Emergent Adverse Events. A subject who reported 2 or more TEAEs with the same preferred term is counted only once for that term. A subject who reported 2 or more TEAEs with different preferred terms within the same system organ class is counted only once in that system organ class.

FIG. 32 shows a summary of treatment-emergent adverse events of special interest detected during treatment period by preferred term (safety analysis set). AESI=Adverse event of special interest. MedDRA (Version 18.0) coding dictionary applied. TEAE: Treatment Emergent Adverse Events. A subject who reported 2 or more TEAEs with the same preferred term is counted only once for that term. A subject who reported 2 or more TEAEs with different preferred terms within the same system organ class is counted only once in that system organ class.

FIG. 33 shows a summary of adverse events of special interest detected during follow-up period by preferred term (safety analysis set). AESI=Adverse event of special interest. MedDRA (Version 18.0) coding dictionary applied. A subject who reported 2 or more AEs with the same preferred term is counted only once for that term. A subject who reported 2 or more AEs with different preferred terms within the same system organ class is counted only once in that system organ class.†In 2 subjects bilateral rapidly progressive osteoarthritis was reported as one event.

FIG. 34 shows a summary of all adverse events of special interest by preferred term during treatment and follow-up period (safety analysis set). AESI=Adverse event of special interest. MedDRA (Version 18.0) coding dictionary applied. A subject who reported 2 or more AEs with the same preferred term is counted only once for that term. A subject who reported 2 or more AEs with different preferred terms within the same system organ class is counted only once in that system organ class.†In 2 subjects bilateral rapidly progressive osteoarthritis was reported as one event.

FIG. 35 shows a summary of arthropathy adjudication data (safety analysis set). RPOA-1: Rapid Progressive OA Type 1; RPOA-2: Rapid Progressive OA Type 2; SIF: Subchondral Insufficiency Fracture, with PT of Stress Fracture. a Was resolved on the week 36 imaging.

FIG. 36 shows a summary of total joint replacement during treatment period and follow-up (safety analysis set). TJR=Total joint replacement.

FIG. 37 shows a summary of alkaline phosphatase over time (safety analysis set).

Figure 38:
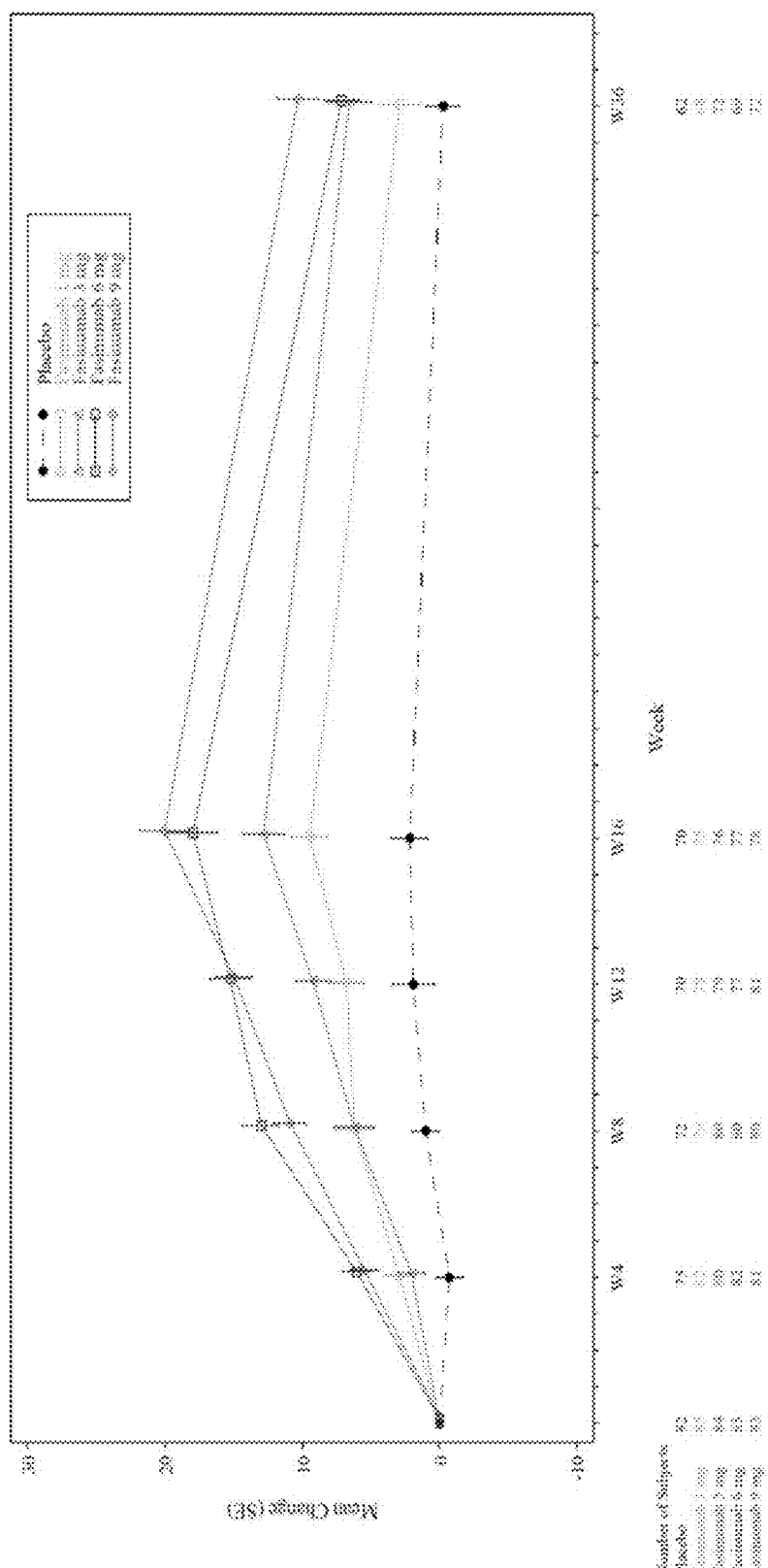

FIG. 38 shows change from baseline in alkaline phosphatase (U/L) by visit: mean (+/−SE) (safety analysis set).

FIG. 39 shows a summary of functional fasinumab concentrations by clinical study day and treatment group following multiple SC injections of fasinumab. N=Number of patients; SD=Standard deviation; Q=Quartile; PRE=Pre-dose; Q4W=Once every 4 weeks; SC=Subcutaneous.

Figure 40:
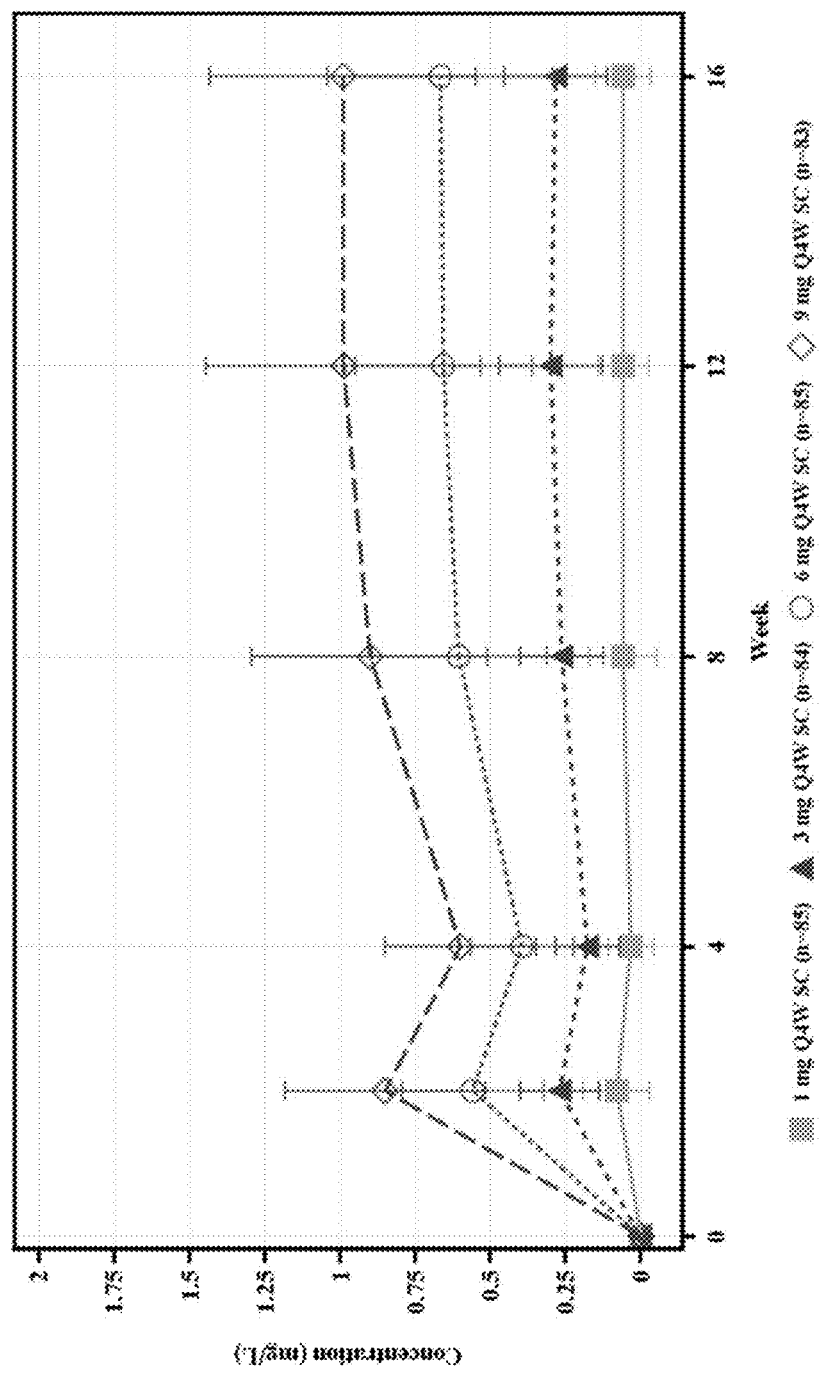

FIG. 40 shows mean (+/−SD) functional fasinumab concentrations vs. week following multiple SC injections of fasinumab. Concentrations below the LLOQ (horizontal dotted line=0.0780 mg/L) are imputed as 0. Placebo patients are excluded.

Figure 41:
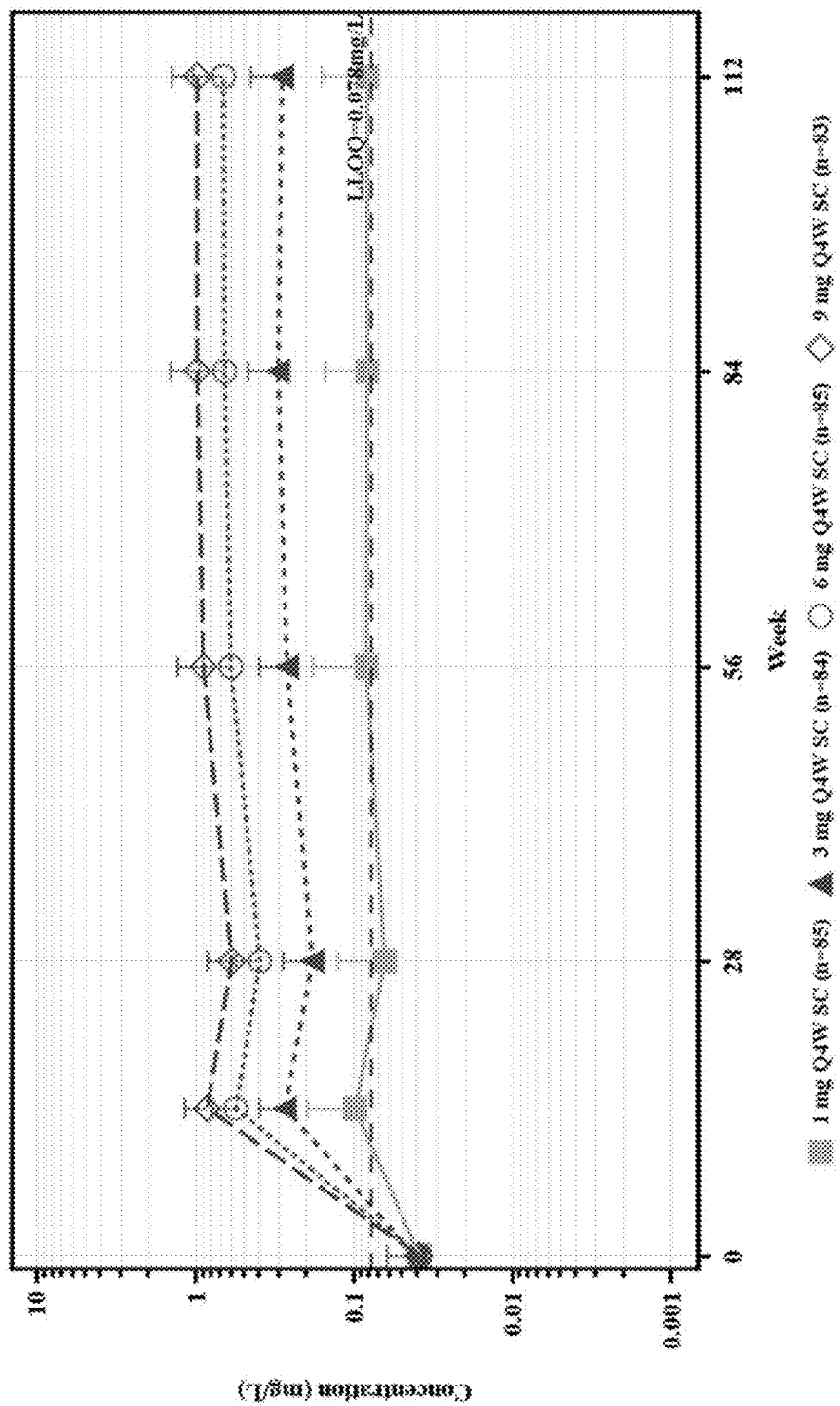

FIG. 41 shows mean (+/−SD) log scaled functional fasinumab concentrations vs. week following multiple SC injections of fasinumab. Concentrations below the LLOQ (horizontal dotted line=0.0780 mg/L) are imputed as LLOQ/2=0.0390 mg/L. Placebo patients are excluded.

FIG. 42 shows patient demographics and baseline characteristics. BMI, body mass index; SD, standard deviation.

FIG. 43 shows change from baseline to week 16 in WOMAC pain subscale score. [a]Analyses are based on a mixed-effect model repeated measures approach. CI, confidence interval; LS, least squares; SD, standard deviation; SE, standard error; WOMAC, Western Ontario and McMaster Universities Osteoarthritis index.

FIG. 44 shows treatment-related adverse events during the treatment and follow-up period reported in >2% of patients by system organ class. MedDRA (version 18.0) coding dictionary was applied for system organ class preferred term. A patient who reported ≥2 TEAEs with the same preferred term was counted only once for that term. A patient who reported ≥2 TEAEs with different preferred terms within the same system organ class was counted only once in that system organ class. AE, adverse event; TEAE, treatment-emergent adverse event.

FIG. 45 shows arthropathies and total joint replacements. During the treatment and follow-up periods combined. In 2 patients, bilateral rapidly progressing OA was reported as 1 event.

Figure 46:
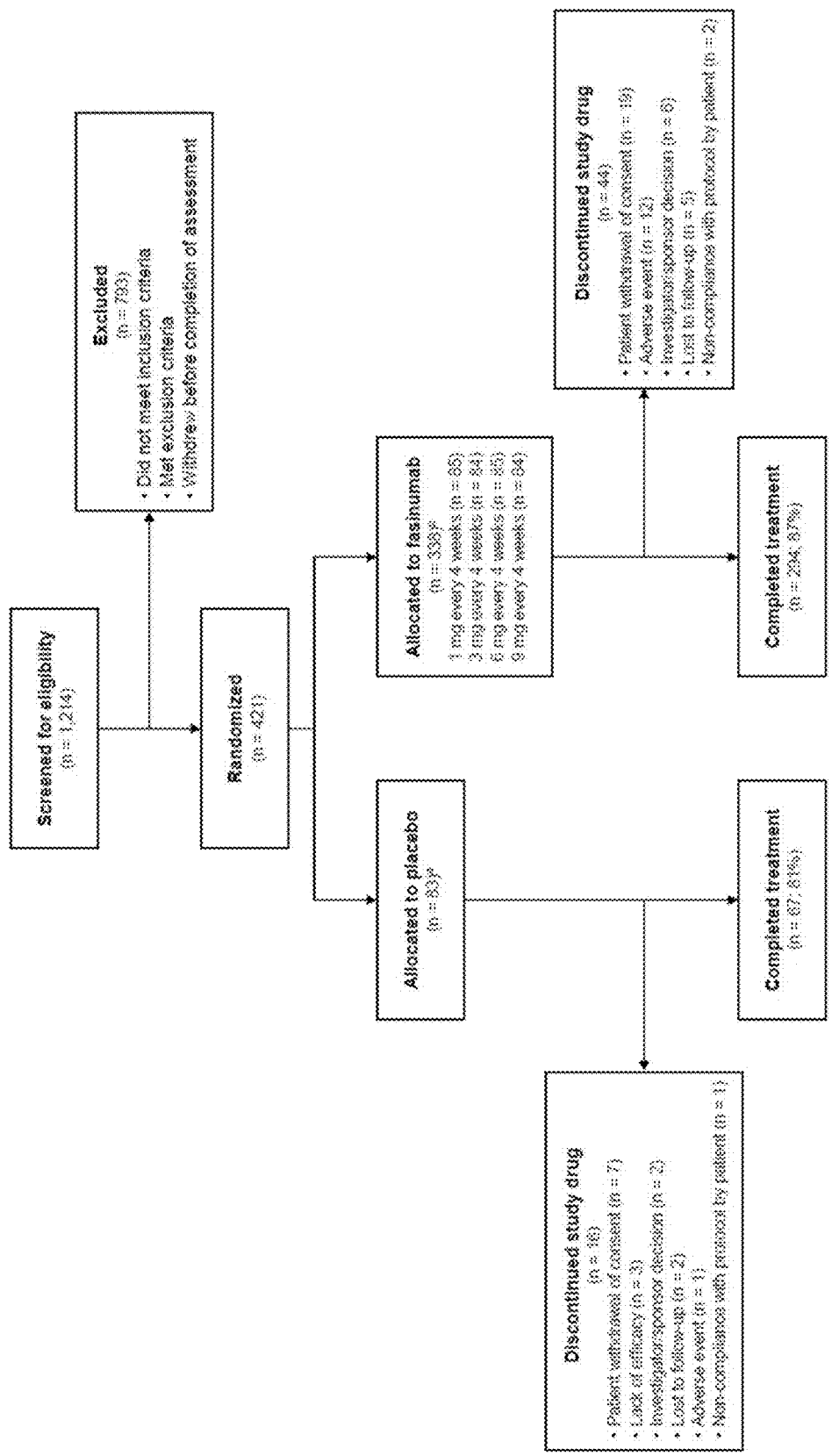

FIG. 46 shows patient disposition. 82 patients received ≥1 doses of placebo. [b]337 patients received ≥1 doses of fasinumab.

Figure 47:
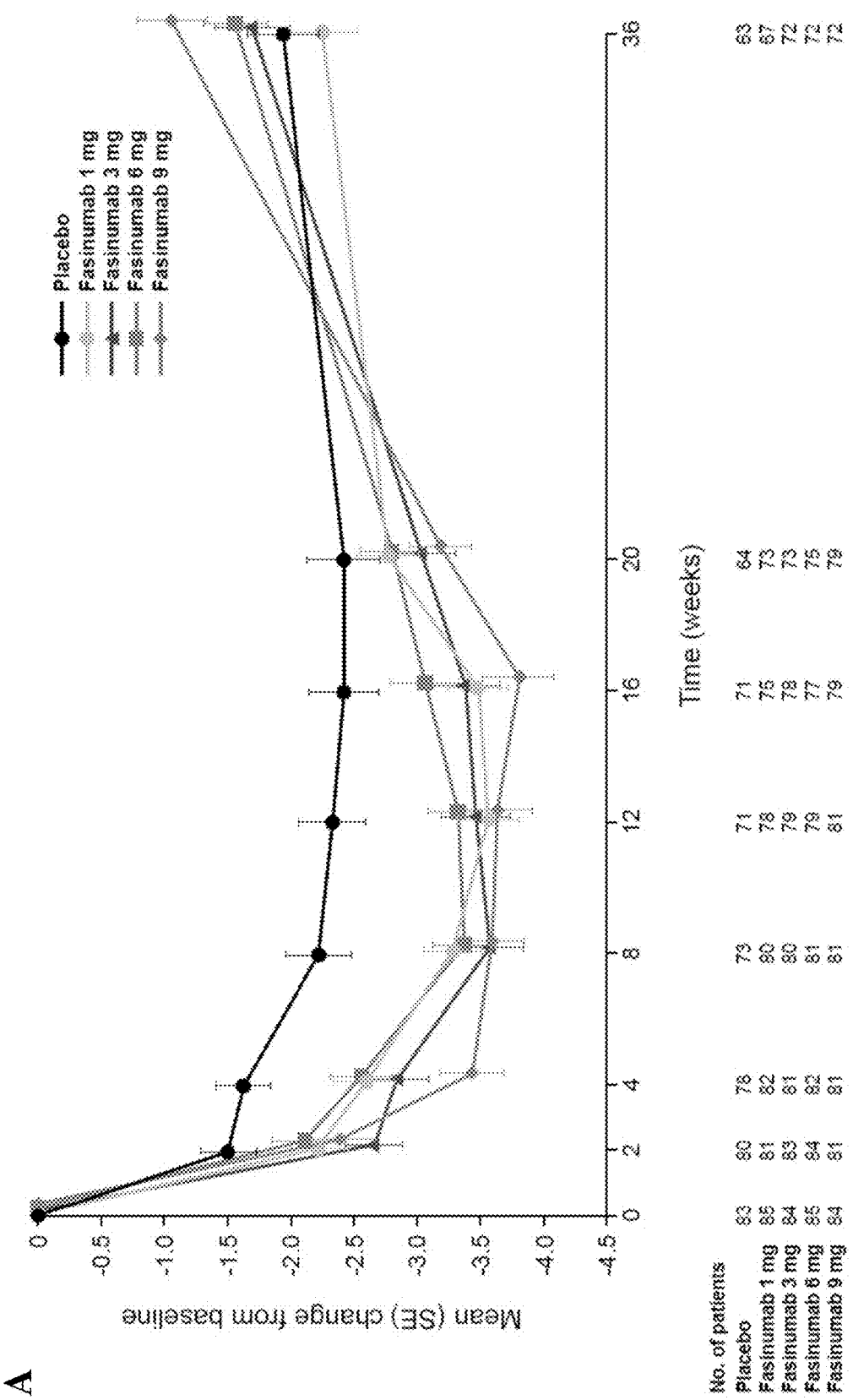
Figure 47:
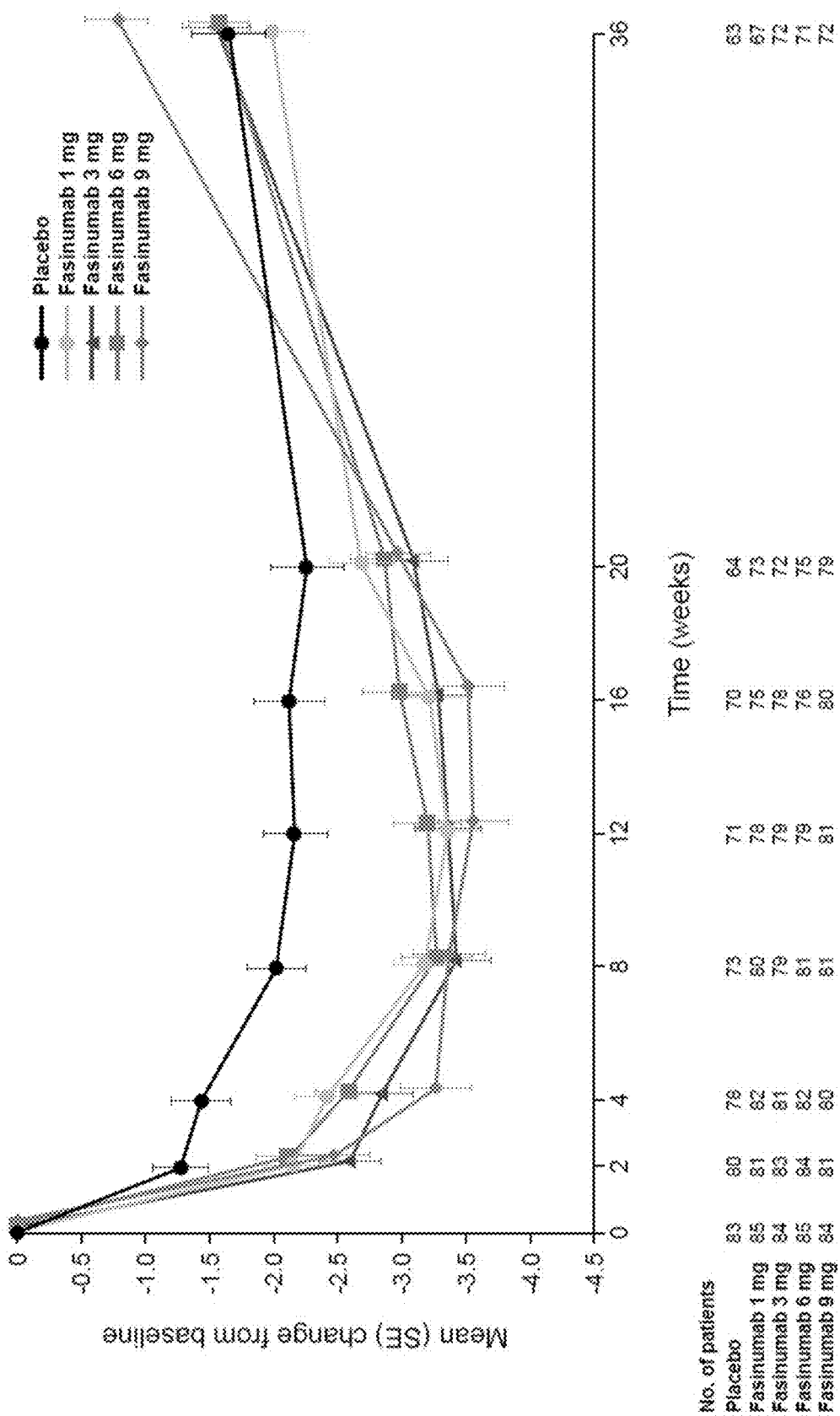
Figure 47:
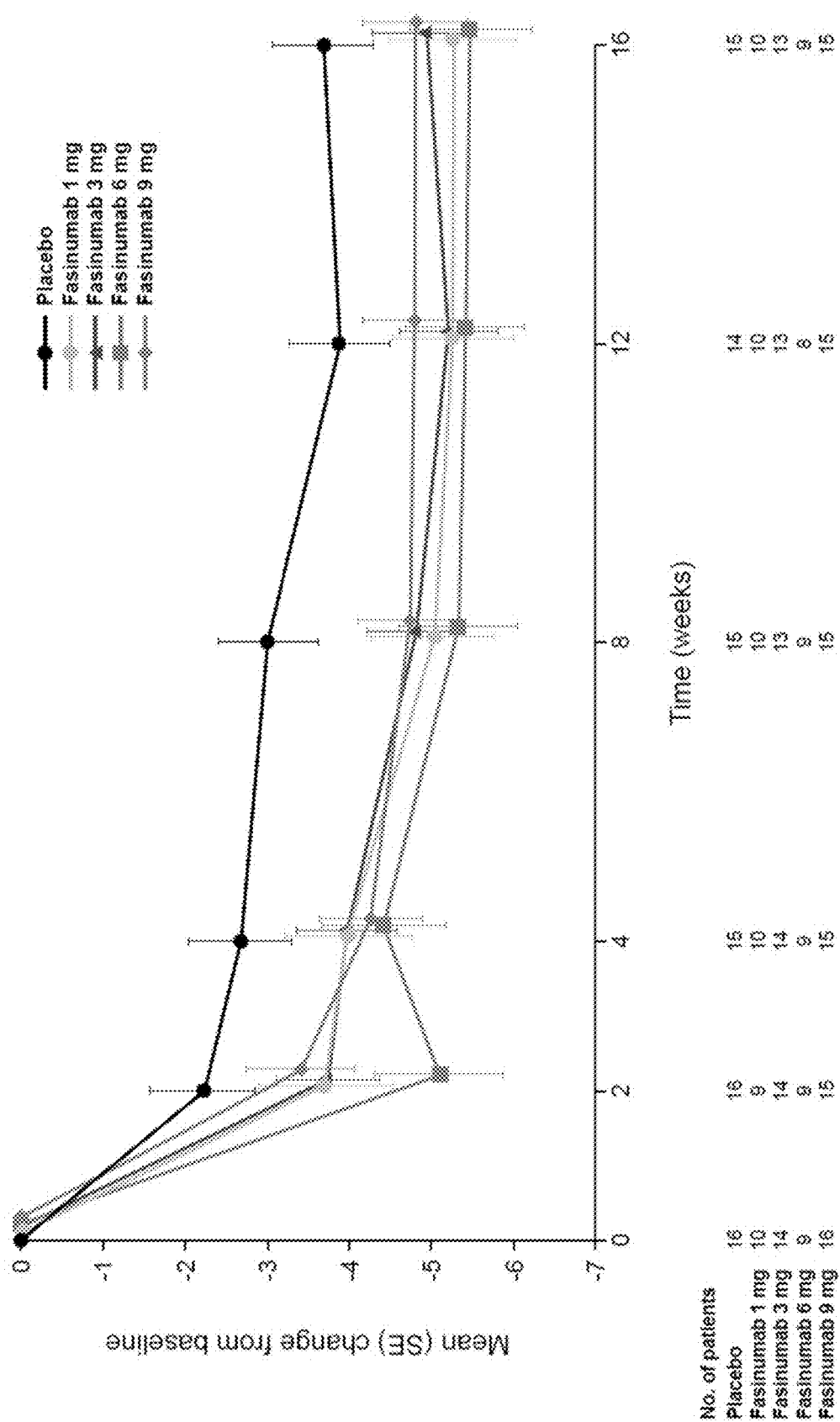
Figure 47:
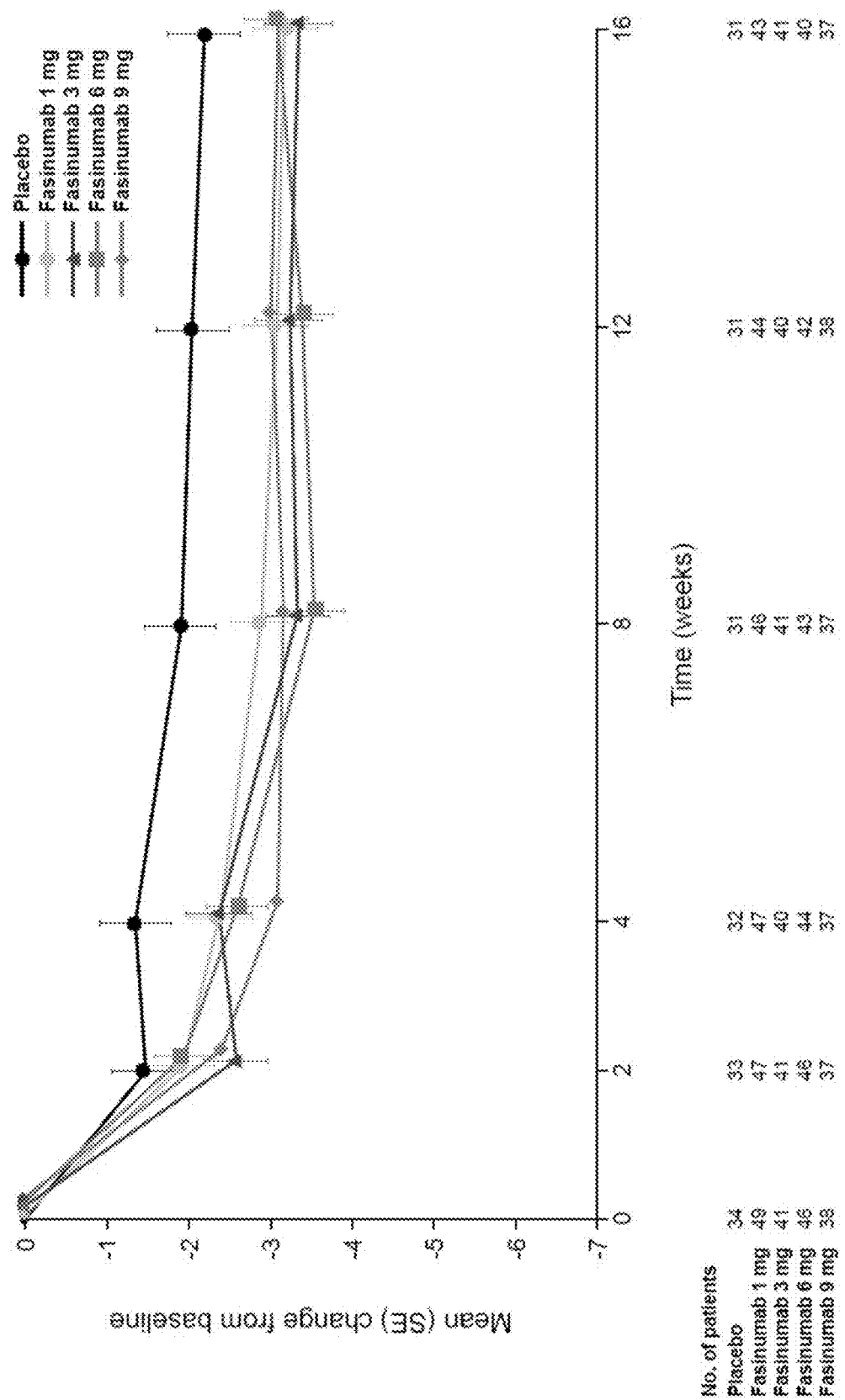

FIG. 47 shows change from baseline in WOMAC pain (A) and physical (B) subscale score by visit, and change from baseline in WOMAC pain subscale score for patients exhibiting (C) and not exhibiting a pain flare (D) on withdrawal of prior analgesic. SE, standard error; WOMAC, Western Ontario and McMaster Universities Osteoarthritis Index.

FIG. 48 shows change from baseline to week 16 in WOMAC physical function subscale score. Analyses are based on a mixed-effects model repeated measures approach. CI, confidence interval; LS, least squares; SD, standard deviation; SE, standard error; WOMAC, Western Ontario and McMaster Universities Osteoarthritis Index.

FIG. 49 shows change from baseline to week 16 in EQ-5D-5L utility index scores. [a]Analyses are based on a mixed-effects model repeated measures approach. EQ-5D-5L utility index scores were calculated using a United Kingdom time-trade-off value set. CI, confidence interval; EQ-5D-5L, EuroQoL-5 Dimension-5 Level scale; LS, least squares; SD, standard deviation; SE, standard error.

Figure 50:
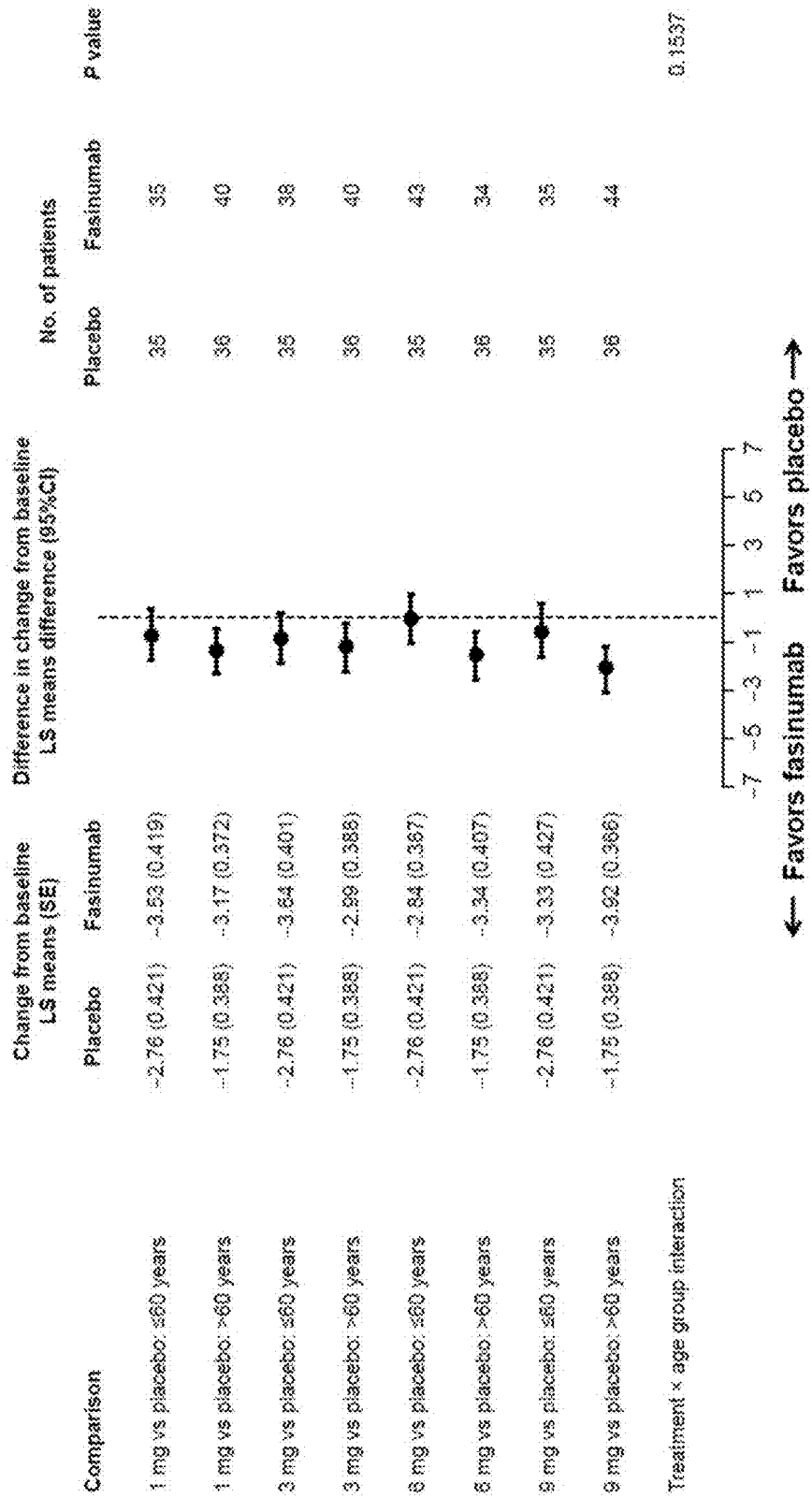
Figure 50:
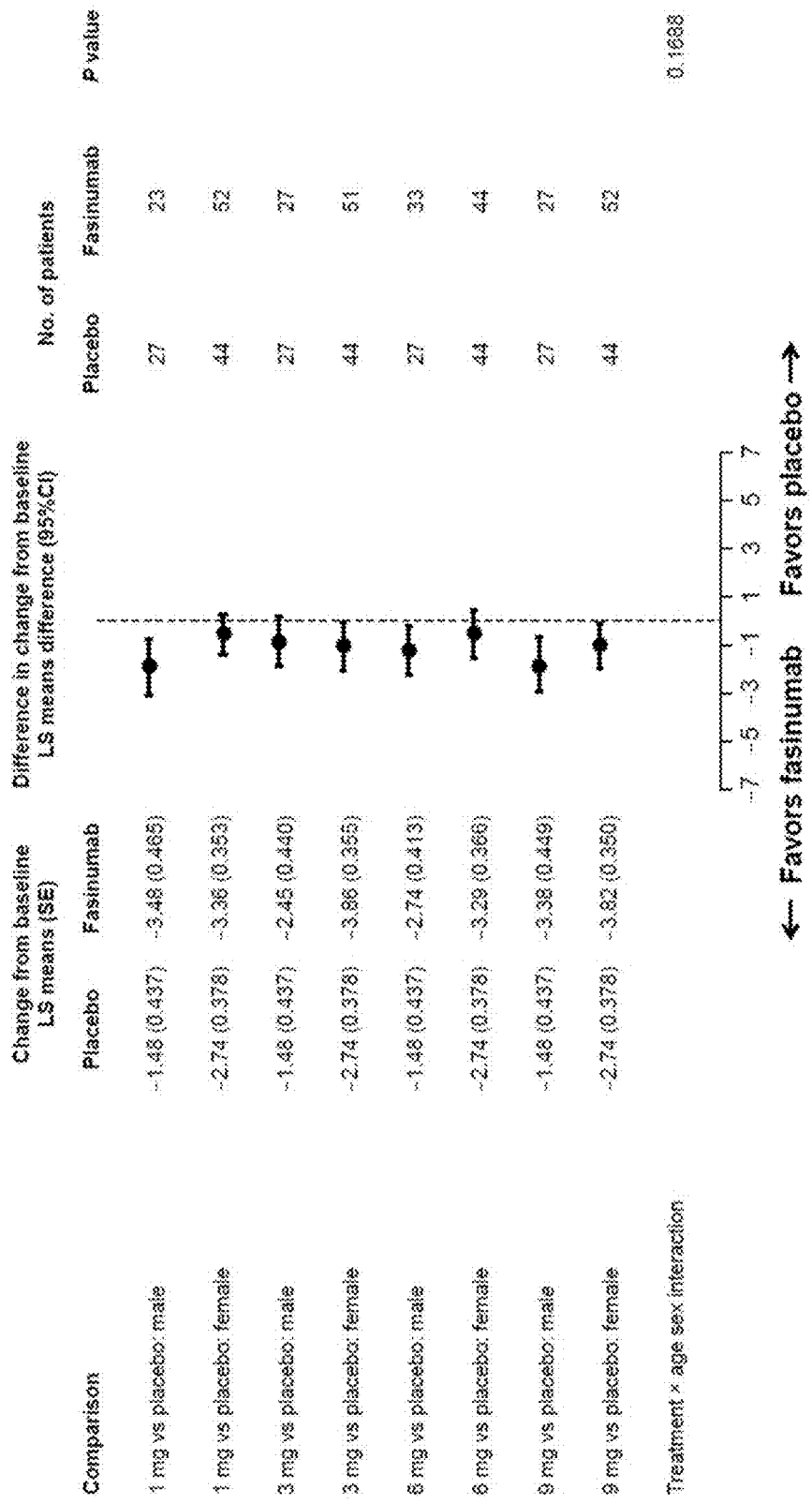
Figure 50:
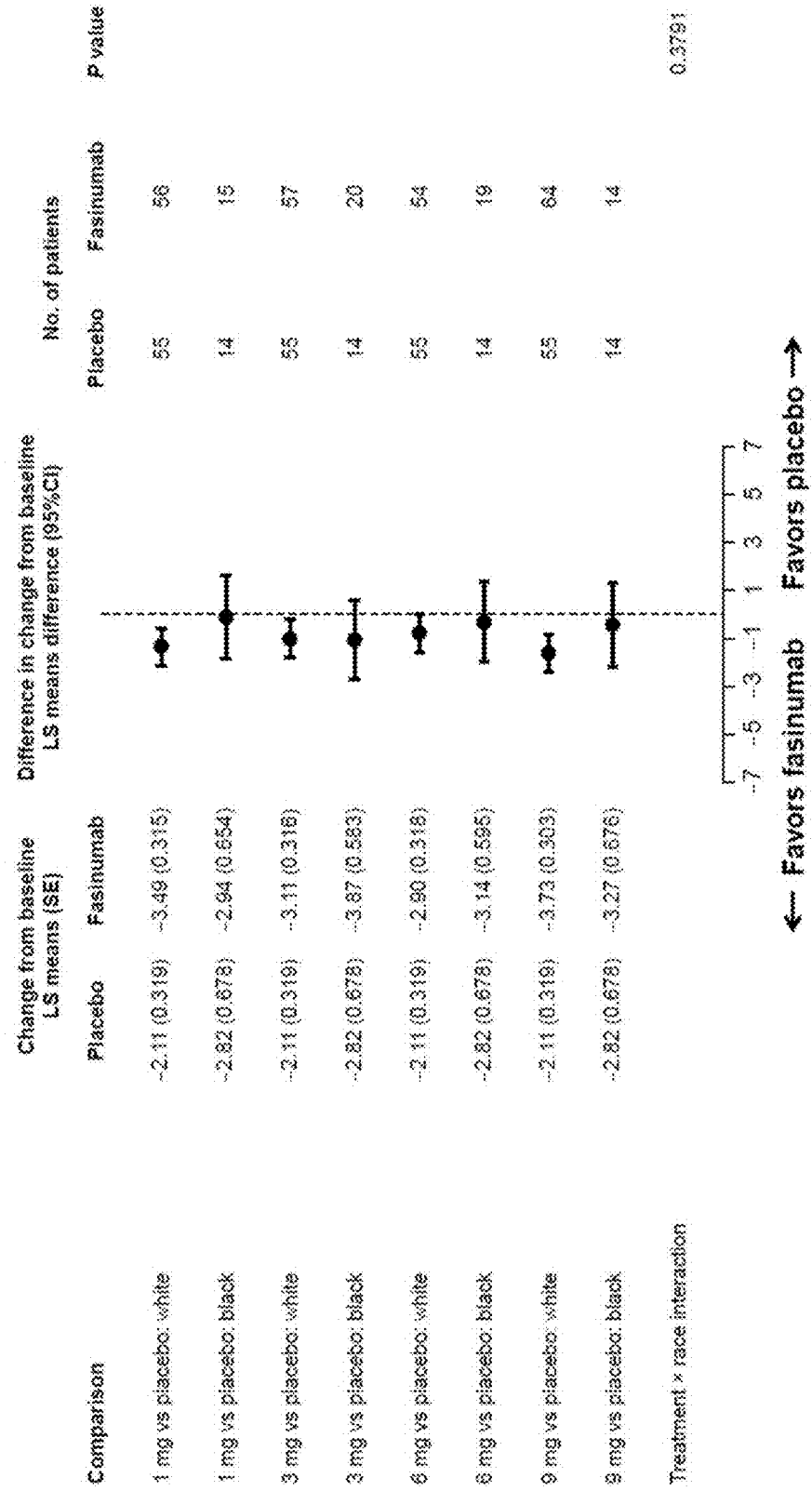
Figure 50:
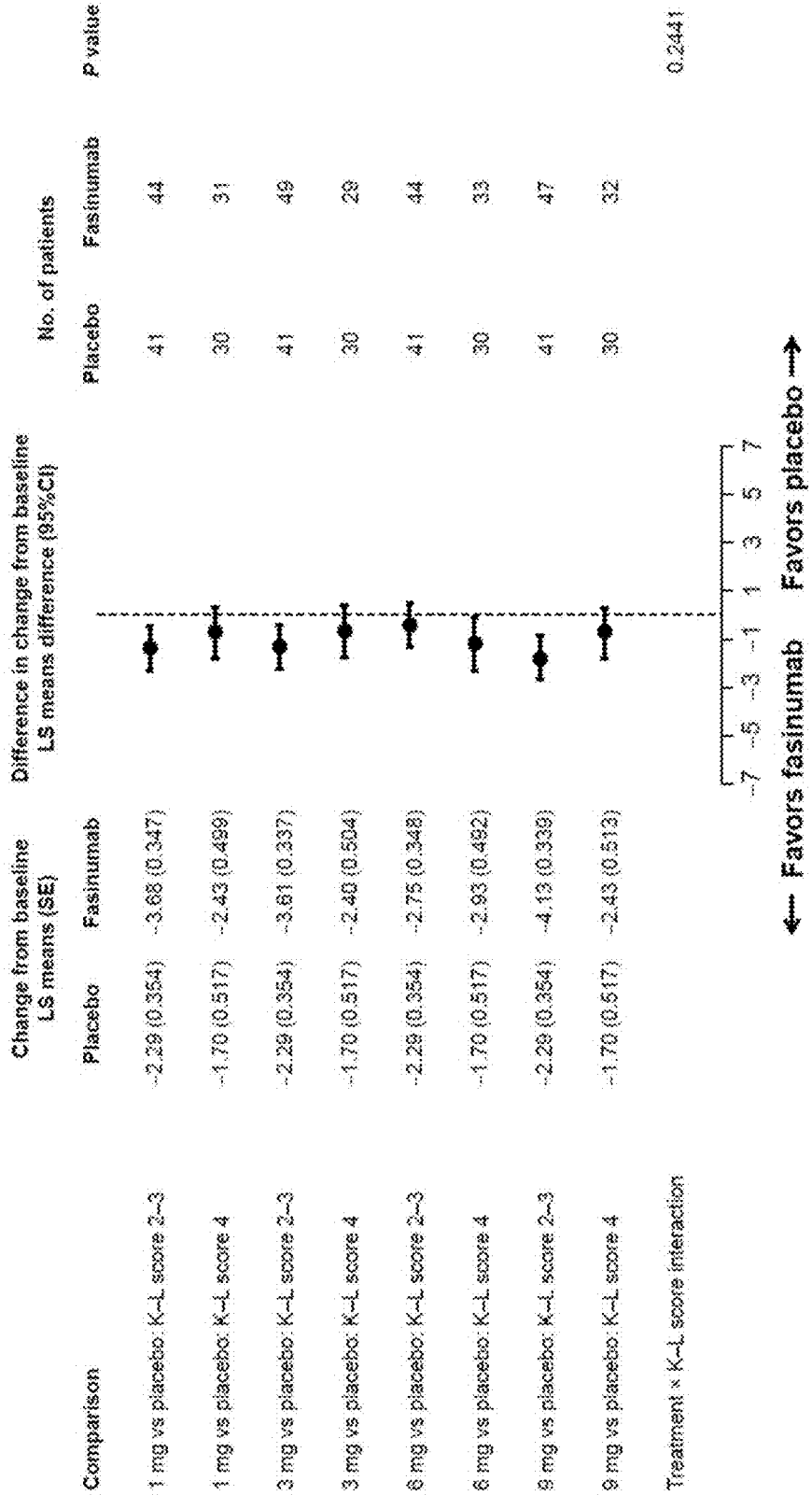
Figure 50:
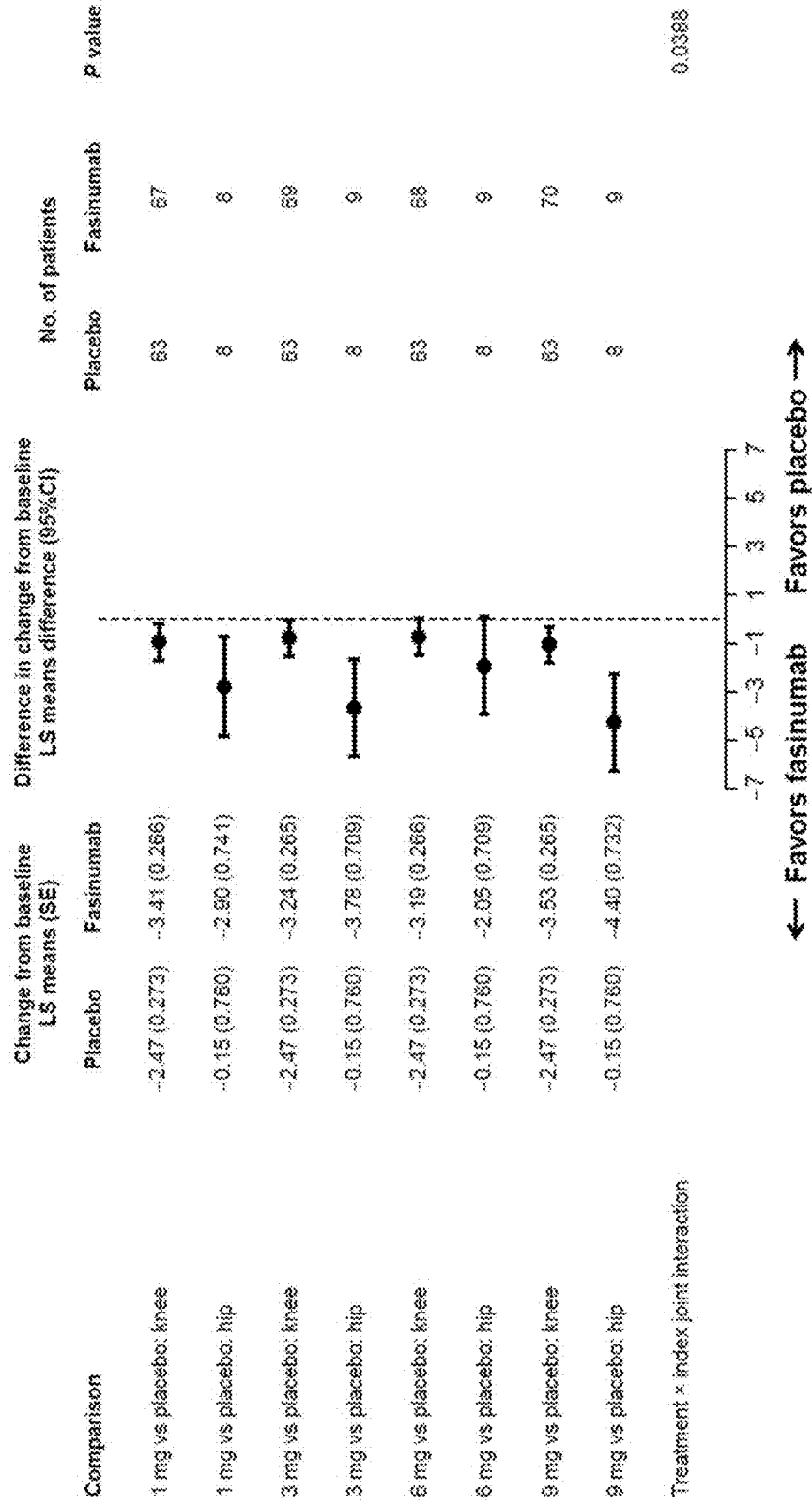
Figure 50:
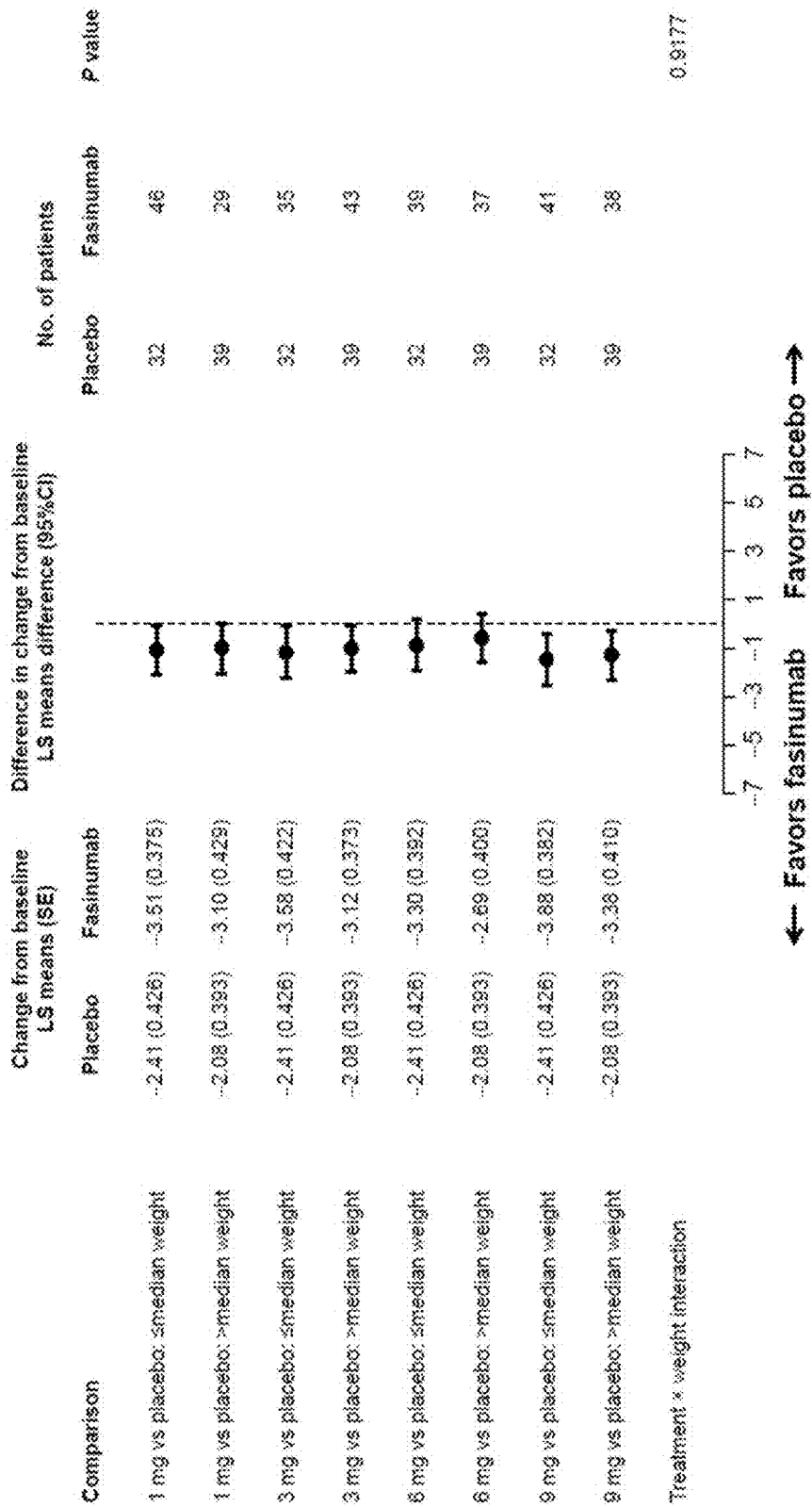
Figure 50:
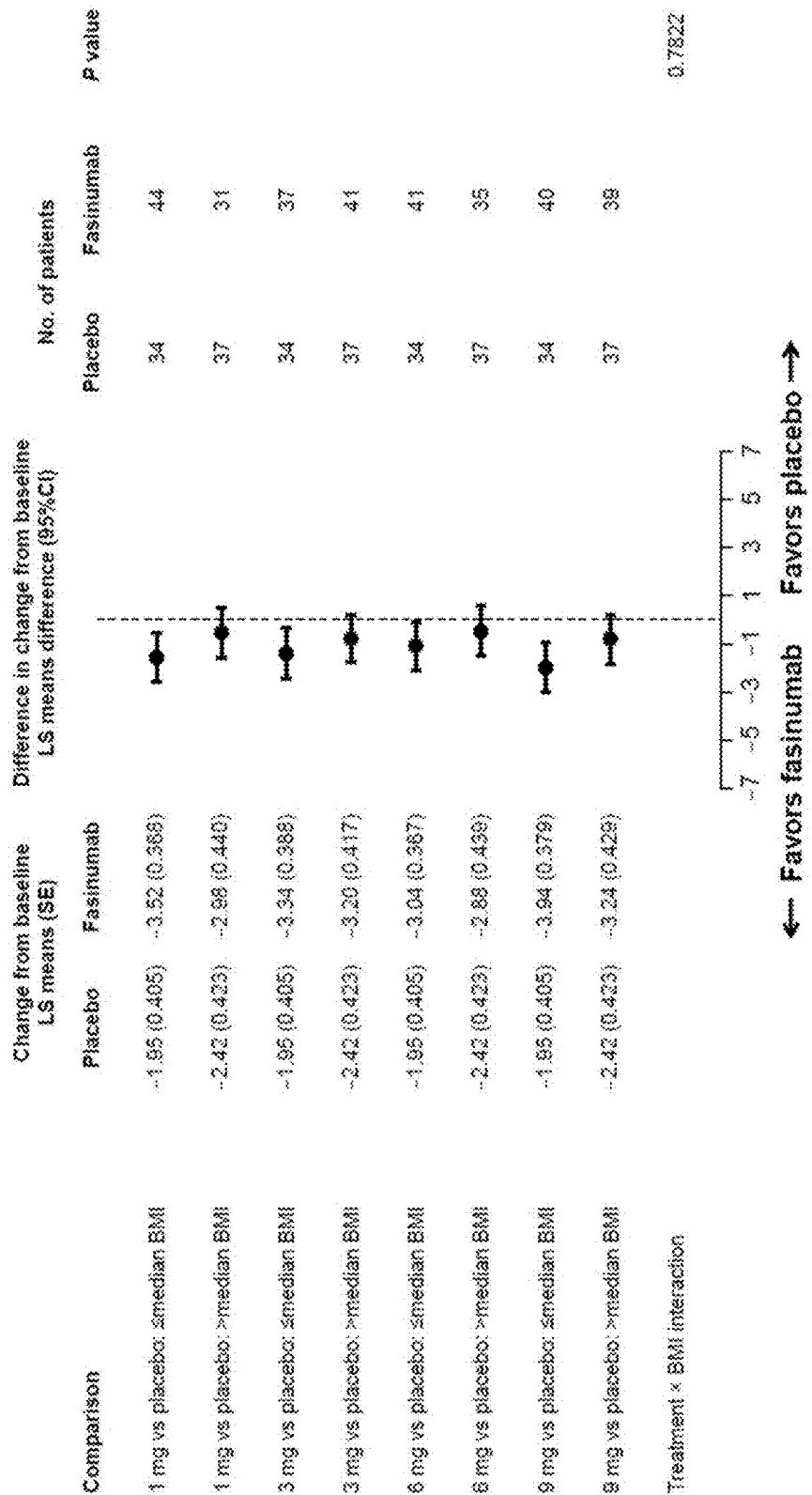

FIG. 50 shows change from baseline to week 16 in WOMAC pain subscale score by age (A), sex (B), race (C), K-L score (D), index joint (E), weight (F), and BMI (G). BMI, body mass index; LS, least squares; SE, standard error; WOMAC, Western Ontario and McMaster Universities Osteoarthritis Index.

Figure 51:
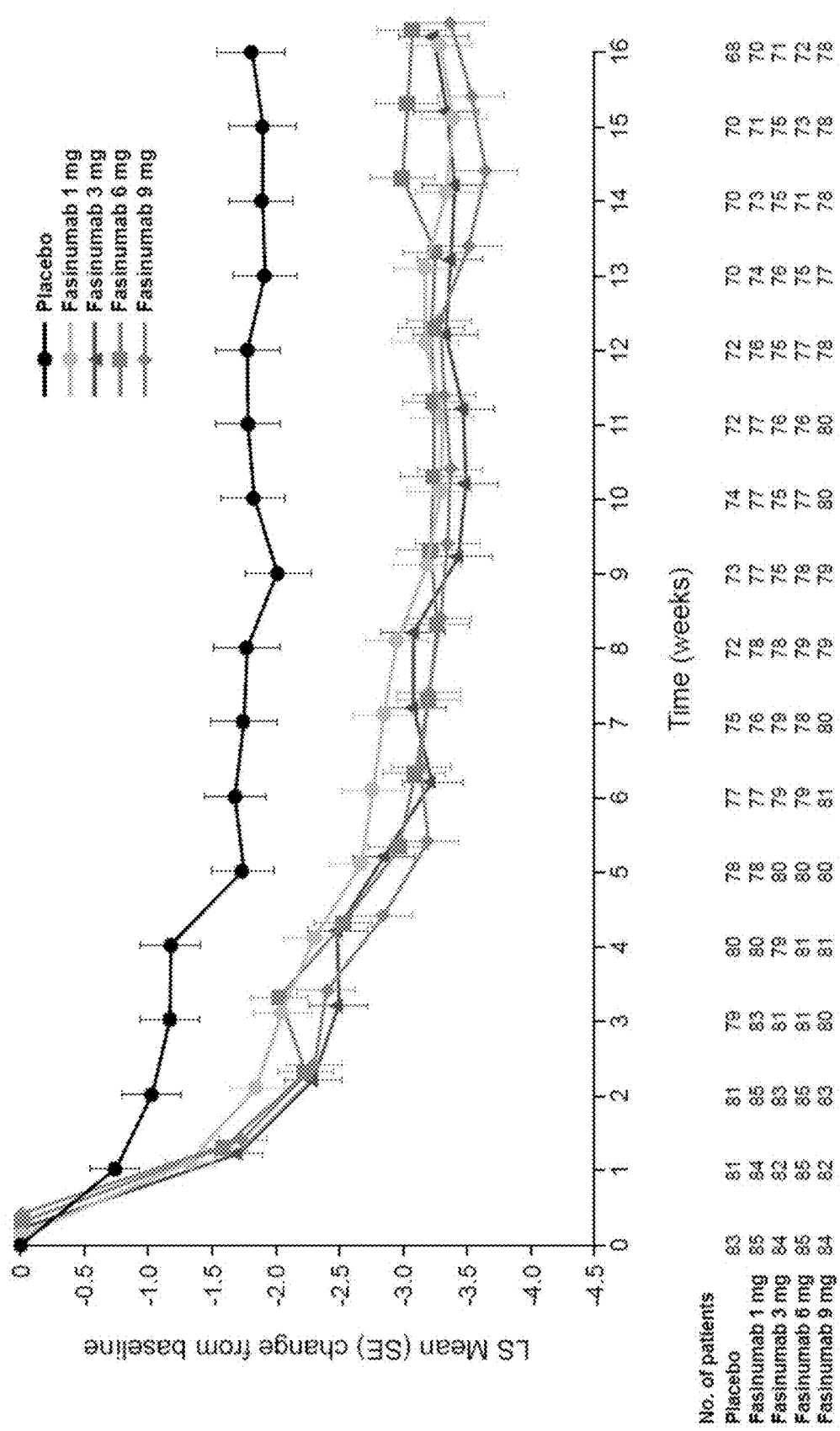

FIG. 51 shows change from baseline in walking pain on the Numeric Rating Scale during the treatment period. LS means were based on a mixed-effects model repeated measures approach with baseline randomization strata, including baseline, treatment, visit, and treatment-by-visit interaction. LS, least squares; SE, standard error.

FIG. 52 provides a summary of change from baseline to week 16 in WOMAC physical function subscale score (full analysis set). N=Number of subjects in Full Analysis Set, and n=Number of subjects within a specified category. SD=Standard deviation, Min=Minimum and Max=Maximum. LS Mean=Least squares mean, SE=Standard error of the LS Mean, and CI=Confidence interval. Analyses are based on MMRM model with baseline randomization strata, baseline, treatment, visit and treatment-by-visit interaction.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.). As used herein, the terms "treat", "treating", or the like, mean to alleviate symptoms, eliminate the causation of symptoms either on a temporary or permanent basis, or to prevent or slow the appearance of symptoms of the named disorder or condition.

Although any methods and materials similar or equivalent to those described herein can be used in the practice of the present invention, the preferred methods and materials are now described. All patents, applications and non-patent publications mentioned herein are incorporated herein by reference in their entireties.

Methods of Treating Knee and/or Hip Pain in Selected Patient Populations

The present invention includes methods and compositions for treating patients with moderate to severe knee and/or hip pain who have a history of intolerance to, or inadequate pain relief from standard therapies, including paracetamol/acetaminophen, oral NSAIDS, and opioid therapy. This subset of patients represents a patient population with an unmet medical need who may benefit from treatment with an NGF antagonist such as fasinumab, which may prove to be efficacious and may provide a better safety profile than other standard therapies.

As described herein, the phrase "moderate to severe knee and/or hip pain" refers to moderate-to-severe pain in the index joint, defined as a Western Ontario and McMaster Universities Osteoarthritis Index (WOMAC) pain subscale score of ≥4. In certain cases, moderate to severe knee and/or hip pain may be caused by osteoarthritis. Thus, a subject with moderate to severe knee and/or hip pain may have been diagnosed with osteoarthritis of the knee and/or hip) based on the American College of Rheumatology criteria for OA with radiologic confirmation (Kellgren-Lawrence [K-L] grading of ≥2 on a scale of 0-4).

Kellgren-Lawrence [K-L] grading system uses plain radiographs and provides grades as follows: Grade 0, No radiographic features of osteoarthritis; Grade 1, Possible joint space narrowing (normal joint space is at least 2 mm at the superior acetabulum) and osteophyte formation; Grade 2, Definite osteophyte formation with possible joint space narrowing; Grade 3, Multiple osteophytes, definite joint space narrowing, sclerosis and possible bony deformity; Grade 4, Large osteophytes, marked joint space narrowing, severe sclerosis and definite bony deformity.

According to certain embodiments of the invention, the patient may be selected for the treatment as disclosed herein based on presenting with a clinical diagnosis of osteoarthritis (OA) of the knee and/or hip.

According to certain embodiments, the subject has a history of regular analgesic medications such as NSAIDS, COX-2 inhibitors, opioids, acetaminophen, or a combination thereof.

According to certain embodiments, the patient has a history of inadequate pain relief or intolerance to analgesics used for treatment of pain as defined by: intolerance or inadequate pain relief from acetaminophen, and intolerance or inadequate pain relief from at least one oral NSAID, and intolerance to, or inadequate pain relief from at least one opioid, unwillingness to take opioid therapy or lack access to opioid therapy.

The present invention includes methods, which comprise administering to a subject in need thereof a therapeutic composition comprising an NGF antagonist. As used herein, the expression "a subject in need thereof" means a human that exhibits knee and/or hip pain. In certain embodiments, "a subject in need thereof" refers to a patient diagnosed with OA of the hip, OA of the knee, or both. In certain embodiments, "a subject in need thereof" refers to a patient suffering from knee and/or hip pain, who has a history of inadequate pain relief from standard analgesic therapy (e.g., no significant pain reduction after administration of the standard analgesic therapy for an average of 4 days/week during a 4 week period), or intolerance to standard analgesic therapy. In certain embodiments, the methods of the present invention may be used to treat patients that have OA of the knee and/or hip with Kellgren-Lawrence [K-L] grading of ≥2 on a scale of 0-4 and/or moderate-to-severe pain in the index joint, defined as a WOMAC pain subscale score of ≥4.

In the context of the present invention, "a subject in need thereof" may also include, e.g., subjects who, prior to treatment, exhibit (or have exhibited) one or more pain-associated parameters, which are improved following treatment with an anti-NGF antibody of the present invention.

In certain aspects, the treatment includes administering a pharmaceutical composition as disclosed herein at a dose that includes about 1 mg to about 9 mg of the anti-NGF antibody or an antigen binding fragment thereof. As demonstrated in the Examples section of this application, doses of 1 mg, 3 mg, 6 mg and 9 mg, provided an improvement in knee pain of a subject having moderate to severe knee pain and an improvement in hip pain of a subject having moderate to severe hip pain, which subject had been unresponsive or intolerant to standard analgesic therapy.

In certain aspects, the improvement demonstrated by the treatment disclosed herein includes an improvement from baseline to week 16 in the WOMAC pain subscale score (a composite index of 5 questions related to joint pain while walking, using stairs, at rest in bed, sitting or lying, and standing) (Bellamy N. WOMAC Osteoarthritis Index: A User's Guide. London, Ontario, Canada: Victoria Hospital; 1995).

In certain aspects, the improvement demonstrated by the treatment disclosed herein includes an improvement from baseline to week 16 in the WOMAC physical function subscale score (scale, 0-68; arithmetically converted to a scale of 0-10).

In certain aspects, the improvement demonstrated by the treatment disclosed herein includes an improvement from baseline to week 16 in Patient Global Assessment (PGA) score (a single question on a scale of 1-5, with worst assessment being the highest score (Strand V, Kellman A. Curr Rheumatol Rep 2004: 6:20-30).

In certain aspects, the improvement demonstrated by the treatment disclosed herein includes an improvement in daily and weekly (average of daily scores over the preceding week) walking index joint pain score on the Numeric Rating Scale (NRS; scale 0-10; 0=no pain; MCID: ~1 point) (Salaffi F, et al. Eur J Pain 2004; 8:283-91).

In certain aspects, the improvement demonstrated by the treatment disclosed herein includes an improvement in the rate of response using the Outcome Measures for Rheumatology Committee and Osteoarthritis Research Society International Standing Committee for Clinical Trials Response Criteria Initiative (OMERACT-OARSI) responder index (an 11-item tool that measures knee or hip OA pain) (Pham T, et al., J Rheumatol 2003; 30:1648-54).

In certain aspects, the improvement demonstrated by the treatment disclosed herein includes an improvement in quality of life assessed using the short form-36 (SF-36) health survey (Ware J E Jr, Sherbourne C D. Med Care 1992; 30:473-83) and EuroQol-5 Dimension-5 Level (EQ-5D-5L) scale utility index score (van Reenen M, Janssen B. EQ-5D-5L User Guide. Version 2.1. Rotterdam, The Netherlands: European Quality of Life Research Foundation; April 2015).

In one aspect, following administration of a pharmaceutical composition disclosed herein, the patient exhibits an improvement in one or more of: (a) Western Ontario and McMaster Universities Osteoarthritis Index (WOMAC) pain score; (b) WOMAC physical function subscale scores; and (c) Patient Global Assessment (PGA) score.

In one embodiment, the patient, following administration of a pharmaceutical composition comprising fasinumab, exhibits an improvement in one or more pain-associated parameters selected from the group consisting of: (a) a change from baseline at week 16 in the average daily pain intensity assessed by Numerical Rating Scale (NRS) score; (b) a change from baseline at week 16 in the Roland Morris Disability Questionnaire (RMDQ) total score; (c) a change from baseline at week 16 in the Patient Global Assessment (PGA) of pain score; (d) a change from baseline at week 2, 4, 8 and 12 in the average daily pain intensity assessed by NRS score; e) a change from baseline at week 16 in the percentage of patients who are responders as defined by a 30% reduction and a 50% reduction for (i) average daily pain intensity NRS score; (ii) RMDQ total score; and (iii) PGA of pain score; f) a change from baseline at week 16 in the Medical Outcomes Study (MOP) sleep subscale score; g) a change from baseline at week 16 in the short form health survey (SF-36) subscale scores; h) a change from baseline at week 16 in the EQ-5D-5L; and i) change from baseline at week 16 in the percentage of patients who use rescue medication for pain.

The severity of the pain is assessed using standard methods known to those skilled in the art. For example, using methods including those described herein, such as the Pain Intensity Numerical Rating Scale (NRS) score; the Roland Morris Disability Questionnaire (RMDQ) total score; or the Patient Global Assessment (PGA) of pain score (See Mannion, A F, et al. Nature Clinical Practice Rheumatology (2007) 3: 610-618.

Various instruments have been developed to evaluate pain intensity (how much a person hurts) and pain affect (how much a person suffers). Three methods have traditionally been used to measure pain intensity: visual analogue scales (VASs), verbal rating scales (VRSs), and numerical rating scales (NRSs). See Von Korff M et al. (2000), Spine 25: 3140-3151; Zanoli G et al. (2000), Spine 25: 3178-3185; Haefeli M and Elfering A (2006), Eur Spine J 15 (Suppl 1): S17-S24; McGuire D B (1999), Instruments for Health-Care Research 528-561 (Eds Frank-Stromborg M and Olsen S) Boston: Jones and Bartlett; Ogon M et al. (1996), Pain 64: 425-428; Hägg O et al. (2003), Eur Spine J 12: 12-20; Jensen M P et al. (1986), Pain 27: 117-126).

The visual analogue scale (VAS) consists of a line, usually 100 mm long, whose ends are labeled as the extremes ('no pain' and 'pain as bad as it could be'); the rest of the line is blank. The patient is asked to put a mark on the line indicating their pain intensity (at the present time, over the past week, or over the past 2 weeks, etc.). The distance between that mark and the origin is measured to obtain the patient's score. Sometimes descriptive terms, such as 'mild', 'moderate' and 'severe', or numbers are provided along the scale for guidance, with "moderate" falling within the mid-range of the scale and the scale is then referred to as a graphic rating scale.

Verbal rating scales (VRSs) consist of a list of adjectives that describe different levels of pain intensity. A VRS for pain includes adjectives that reflect the extremes (e.g. 'no pain' to 'pain as bad as it could be'), and sufficient adjectives to capture the gradations in between. VRSs are most frequently five-point or six-point scales. The patient is asked to select in a questionnaire or state verbally the adjective that best describes his or her level of pain intensity. In behavioral rating scales, different pain levels are described by sentences including behavioral parameters.

The numeric rating scale (NRS) involves asking patients to rate their pain intensity by selecting a number on a scale from 0-10 (11-point scale), 0-20 (21-point scale), or 0-100 (101-point scale) by filling in a questionnaire or stating verbally a numerical level. For example, a zero (0) would mean "no pain" and a one hundred (100) would mean "pain as bad as it could be". The patient is asked to write only one number. For example, using the 0-10 NRS, a patient exhibiting "moderate LBP" may enter a number between 4-6 for "moderate pain" and between 7-10 for "severe pain". See the exemplary table below.

| Rating | Pain Level |
|---|---|
| 0 | No Pain |
| 1-3 | Mild Pain (nagging, annoying, interfering little with activity of daily living (ADLs) |
| 4-6 | Moderate Pain (interferes significantly with ADLs) |
| 7-10 | Severe Pain (disabling; unable to perform ADLs) |

A patient may also be said to have moderate-to-severe knee and/or hip pain when the patient is resistant or refractory to treatment by standard analgesics, such as acetaminophen or an NSAID, or any other commonly used therapeutic agent known in the art for treating knee and/or hip pain.

As noted above, the present invention includes methods to treat knee and/or hip pain in patients who exhibit a history of inadequate pain relief, or intolerance to standard analgesic therapy, or who are resistant, non-responsive or inadequately responsive to treatment with a standard analgesic. The term "inadequate pain relief" refers to an unacceptable level of pain relief experienced by subjects after treatment with a standard analgesic, who may find that they cannot go about conducting normal daily activities due to the pain level index.

The term "intolerance to standard analgesic therapy" refers to subjects or patients who, for example, are allergic to a standard analgesic, or who exhibit an adverse event after treatment with the standard analgesic. The term "resistant, non-responsive or inadequately responsive to a standard analgesic", as used herein, refers to subjects or patients with knee and/or hip pain who have been treated with for example, an NSAID, and wherein the NSAID does not have a therapeutic effect. In some embodiments, the term refers to reduced patient compliance and/or toxicity and side effects and/or ineffectiveness of the administered analgesic to reduce, ameliorate or decrease the symptoms of knee and/or hip pain. In some embodiments, the term refers to patients suffering from moderate-to-severe knee and/or hip pain who are refractory to treatment by a standard analgesic. In some embodiments, the patients who are "resistant, non-responsive or inadequately responsive to a standard analgesic" may show no improvement in one or more pain-associated parameters. Examples of pain-associated parameters are described elsewhere herein. For example, treatment with a standard analgesic may result in no change in the knee and/or hip pain NRS score, or in the Roland Morris Disability Questionnaire (RMDQ) total score. In some embodiments, the present invention includes methods to treat moderate-to-severe knee and/or hip pain in patients who have been treated earlier with an analgesic, e.g. for ≥1 month and do not show a change (e.g. a decrease) in one or more pain-associated parameters.

Although any methods and materials similar or equivalent to those described herein can be used in the practice of the present invention, the preferred methods and materials are now described. All publications mentioned herein are incorporated herein by reference to describe in their entirety.

Methods for Reducing Risk of Developing Arthropathy Associated with Use of Anti-NGF Antibody In certain aspects, the methods and compositions of the present disclosure are used for averting arthropathy developed in a subset of patients receiving a higher dose of an anti-NGF antibody or a fragment thereof for treatment of hip and/or knee pain.

As evident from the data provided in the Examples section of the application, about 7% of the patients receiving anti-NGF antibody at a dose of 6 mg or 9 mg developed arthropathy. Thus, in certain aspects, the methods and compositions for treating hip and/or knee pain may include use of an anti-NGF antibody at a dose of less than 9 mg or a dose of less than 6 mg.

In certain aspects, the methods and compositions for treating hip and/or knee pain may avoid arthropathy by using an anti-NGF antibody at a dose of less than 5 mg, e.g. 1 mg-4 mg, e.g., 1 mg or 3 mg.

In certain aspects, the arthropathy that is avoided by the disclosed compositions and treatment methods is adjudicated arthropathy. In certain aspects, the arthropathy comprises rapidly progressive OA. The OA may be type 1 in which joint space narrowing exceeding pre-specified thresholds occurs. In certain aspects, OA may be type 2 where changes in bone structure on plain film is observable. Plain film refers to plain X-ray radiography and does not require computed tomography (CT), ultrasound imaging or magnetic resonance imaging (MRI). In certain aspects, the arthropathy that is avoided by the disclosed compositions and treatment methods is joint space narrowing exceeding pre-specified thresholds, changes in bone structure on plain film, or both.

The dose of anti-NGF antibody suitable for avoidance of arthropathy may be administered intravenously or subcutaneously at a frequency of every 4 weeks for a period of up to 16 weeks.

In certain aspects, the methods and compositions disclosed herein may reduce the incidence of arthropathy in subjects receiving the treatment by at least 50% (e.g., at least 55%, at least 60%, at least 70%) as compared to the incidence of the arthropathy in a subject receiving a higher dose of the anti-NGF antibody, e.g., a subject receiving a dose of at least 6 mg or at least 9 mg of the anti-NGF antibody.

In certain aspects, the methods and compositions disclosed herein may reduce the occurrence of rapidly progressive osteoarthritis in subjects receiving the treatment by at least 50% (e.g., at least 55%, at least 60%, at least 70%) as compared to a subject receiving a higher dose of the anti-NGF antibody, e.g., a subject receiving a dose of at least 6 mg or at least 9 mg of the anti-NGF antibody.

The subjects who may benefit from the disclosed method and composition for reducing risk of developing arthropathy may be the same as those disclosed in the preceding section. For example, the subject is non-responsive to analgesic treatment or suffers from side-effects from analgesic treatment, the subject is diagnosed as having OA of the knee and/or hip, the subject is diagnosed with moderate-to-severe pain in the index joint in the knee and/or hip, defined as a Western Ontario and McMaster Universities Osteoarthritis Index (WOMAC) pain subscale score of ≥4, the subject has a Kellgren-Lawrence [K-L] grading of ≥2 on a scale of 0-4, prior to initiation of the treatment, the subject has a Kellgren-Lawrence [K-L] grading of 3 or 4 on a scale of 0-4, and/or the subject has received analgesic therapy for an average of 4 days/week during a 4 week period prior to initiation of treatment with an anti-NGF antibody.

Method for Monitoring Safety of Treatment with NGF Antagonists

As shown in the Examples section of the application, doses of about 9 mg and of about 6 mg may have certain benefits as compared to doses of 3 mg and 1 mg of the anti-NGF antibody in treating hip and/or knee pain. For example, the higher dose may result in pain alleviation and/or increase function in the knee of hip at a higher rate than the lower doses. However, in a small subset of patients receiving the higher dose (e.g., about 9 mg of about 6 mg of fasinumab), treatment-emergent adverse events (TEAEs), such as arthropathy may occur.

The method for treatment of hip and/or knee pain as disclosed herein combines the superior results associated with the higher dose of anti-NGF antibody with the reduced risk of treatment-emergent adverse events (TEAEs), such as arthropathy seen with the lower dose (e.g. less than 6 mg of anti-NGF antibody).

In certain aspects, the method may include administering a higher dose of the anti-NGF antibody; monitoring a joint (e.g., knee joint or a hip joint) of the subject to determine whether the subject has developed an arthropathy; wherein if the subject has developed arthropathy, administering a pharmaceutical composition comprising a dose of less than about 9 mg of the antibody or the antigen binding fragment thereof to the subject; or wherein if the subject has not developed arthropathy, administering a pharmaceutical composition comprising a dose of about 9 mg of the antibody or the antigen binding fragment thereof to the subject.

If the subject has developed arthropathy, the subsequent treatment comprises administering a pharmaceutical composition comprising 1.0 mg to about less than 6 mg of the anti-NGF antibody or an antigen binding fragment thereof, wherein the treatment reduces pain in the knee joint or the hip joint and reduces arthropathy.

The subjects who may benefit from the disclosed method for monitoring safety of treatment with anti-NGF antibody may be the same as those disclosed in the preceding sections. For example, the subject is non-responsive to analgesic treatment or suffers from side-effects from analgesic treatment, the subject is diagnosed as having OA of the knee and/or hip, the subject is diagnosed with moderate-to-severe pain in the index joint in the knee and/or hip, defined as a Western Ontario and McMaster Universities Osteoarthritis Index (WOMAC) pain subscale score of ≥4, the subject has a Kellgren-Lawrence [K-L] grading of ≥2 on a scale of 0-4, prior to initiation of the treatment, the subject has a Kellgren-Lawrence [K-L] grading of 3 or 4 on a scale of 0-4, and/or the subject has received analgesic therapy for an average of 4 days/week during a 4 week period prior to initiation of treatment with an anti-NGF antibody.

Arthropathy may be same as disclosed in the preceding section. Monitoring for presence of arthropathy may include conducting radiology of the hip and/or the knee joint. In certain aspects, development of arthropathy at other locations, such as, shoulders, finger, toes, may be assessed. Assessment of arthropathy may also include conducting CT scans, MRI, or ultrasound of joints such as in the hip, knee, shoulder, fingers, and/or toes.

In certain aspects, arthropathy may be monitored after administration of a dose of the anti-NGF but prior to administration of a secondary dose. For example, presence of arthropathy may be monitored at 2 weeks, 3 weeks, or 4 weeks after administration of the anti-NGF. If arthropathy is detected, the secondary dose may be reduced relative to the prior dose.

In certain aspects, once the lower dose is administered, the subject may be again monitored for resolution of the arthropathy. If arthropathy is reduced by about 4 weeks after administration of the lower dose, the next dose may be increased and so on.

In certain aspects, the method may include administering a 9 mg dose of the anti-NGF antibody; monitoring a joint (e.g., knee joint or a hip joint) of the subject to determine whether the subject has developed an arthropathy; wherein if the subject has developed arthropathy, administering a pharmaceutical composition comprising a dose of less than about 9 mg of the antibody or the antigen binding fragment thereof to the subject; or wherein if the subject has not developed arthropathy, administering a pharmaceutical composition comprising a dose of about 9 mg of the antibody or the antigen binding fragment thereof to the subject.

In certain aspects, the method may include administering a 6 mg dose of the anti-NGF antibody; monitoring a joint (knee joint or a hip joint) of the subject to determine whether the subject has developed an arthropathy; wherein if the subject has developed arthropathy, administering a pharmaceutical composition comprising a dose of less than about 6 mg of the antibody or the antigen binding fragment thereof to the subject; or wherein if the subject has not developed arthropathy, administering a pharmaceutical composition comprising a dose of about 6 mg of the antibody or the antigen binding fragment thereof to the subject.

In certain aspects, if the subject has developed arthropathy, the one or more secondary doses may be 1 mg till the arthropathy is reduced or is undetectable. Once the arthropathy is undetectable, the subsequent dose may be same as the initial dose. If the arthropathy is reduced, the subsequent dose may be 3 mg till the arthropathy is undetectable. Once the arthropathy is undetectable, the subsequent dose may be same as the initial dose.

Methods for Improving Pain-Associated Parameters: Therapeutic Efficacy Measurements The present invention includes methods for improving one or more pain-associated parameters in a subject in need thereof, wherein the methods comprise administering a pharmaceutical composition comprising an NGF antagonist, e.g., an anti-NGF antibody of the invention or an antigen binding fragment thereof, to the subject.

Examples of "pain-associated parameters" include: (a) Western Ontario and McMaster Universities Osteoarthritis Index (WOMAC) pain score; (b) physical function subscale scores; and (c) Patient Global Assessment (PGA) score the knee and/or hip pain Numerical Rating Scale (NRS) score; (d) the Roland Morris Disability Questionnaire (RMDQ) total score; (e) the Medical Outcomes Study (MOP) sleep subscale score; (f) the short form health survey (SF-36) subscale scores; (g) the EQ-5D-5L; and (h) the percentage of patients who use rescue medication for knee and/or hip pain.

An "improvement in a pain-associated parameter" means a significant change from baseline in one or more of the following: (a) a change from baseline at week 16 in the average daily knee and/or hip pain intensity Numerical Rating Scale (NRS) score; (b) a change from baseline at week 16 in the Roland Morris Disability Questionnaire (RMDQ) total score; (c) a change from baseline at week 16 in the Patient Global Assessment (PGA) of knee and/or hip pain score; or (d) a change from baseline at week 2, 4, 8 and 12 in the average daily knee and/or hip pain NRS score. In addition, an "improvement in a pain-associated parameter" means a significant change from baseline in one or more of the following: (e) a change from baseline at week 16 in the percentage of patients who are responders as defined by a 30% reduction and a 50% reduction for (i) average daily knee and/or hip pain NRS score; (ii) RMDQ total score; and (iii) PGA of knee and/or hip pain score; or (f) a change from baseline at week 16 in the Medical Outcomes Study (MOP) sleep subscale score; or (g) a change from baseline at week 16 in the short form health survey (SF-36) subscale scores; or (h) a change from baseline at week 16 in the EQ-5D-5L; or i) a change from baseline at week 16 in the percentage of patients who use rescue medication for knee and/or hip pain.

As used herein, the term "baseline," with regard to a pain-associated parameter, means the numerical value of the pain-associated parameter for a subject prior to or at the time of administration of a pharmaceutical composition of the present invention.

To determine whether a pain-associated parameter has "improved," the parameter is quantified at baseline and at one or more time points after administration of the pharmaceutical composition of the present invention. For example, a pain-associated parameter may be measured at various time points after administration of fasinumab, e.g., at day 1, day 2, day 3, day 4, day 5, day 6, day 7, day 8, day 9, day 12, day 18, day 22, day 36, day 50, day 57, day 64, day 78, day 85, day 92, day 106, day 113, day 120; or at the end of week 1, week 2, week 3, week 4, week 5, week 6, week 7, week 8, week 9, week 10, week 11, week 12, week 13, week 14, week 15, week 16, or longer, after the initial treatment with a pharmaceutical composition of the present invention.

The difference between the value of the parameter at a particular time point following initiation of treatment and the value of the parameter at baseline is used to establish whether there has been an "improvement" (e.g., a decrease) in the pain associated parameter.

Western Ontario and McMaster Universities Osteoarthritis Index (WOMAC) pain subscale score: WOMAC pain subscale score is a composite index of 5 questions related to joint pain while walking, using stairs, at rest in bed, sitting or lying, and standing and is described in Bellamy N. WOMAC Osteoarthritis Index: A User's Guide. London, Ontario, Canada: Victoria Hospital; 1995. Individual WOMAC questions are scored on a scale of 0-10. The scores from each of the 5 questions are averaged.

WOMAC physical function subscale score: WOMAC physical function subscale score measures 17 items for functional limitation (scale, 0-68; arithmetically converted to a scale of 0-10). Physical functioning questions cover everyday activities such as stair use, standing up from a sitting or lying position, standing, bending, walking, getting in and out of a car, shopping, putting on or taking off socks, lying in bed, getting in or out of a bath, sitting, and heavy and light household duties.

The knee and/or hip pain Intensity-Numeric Rating Scale: The knee and/or hip pain intensity numeric rating scale (NRS) involves asking patients to rate their pain intensity by selecting a number on a scale from 0-10 (11-point scale), 0-20 (21-point scale), or 0-100 (101-point scale) by filling in a questionnaire or stating verbally a numerical level. For example: "Please indicate on the line below the number between 0 and 100 that best describes your pain. A zero (0) would mean 'no pain' and a one hundred (100) would mean 'pain as bad as it could be'. Please write only one number." An empty box or line is provided for the corresponding number to be entered. A slight variation of the NRS is the box scale, where each number (e.g. 0-10) is written in a box and patients are asked: "If a zero (0) means 'no pain' and a ten (10) means 'pain as bad as it could be', on this scale of 0-10, what is your level of pain? Put an "X" through that number." According to certain embodiments of the present invention, administration of an NGF antagonist to a patient results in a decrease in the NRS score. For example, the present invention includes therapeutic methods which result in a decrease from baseline in the NRS score of at least about 10%, 20%, 30%, 40%, 50%, or more at week 2, 4, 8, 12 and 16, or later following administration of the NGF antagonist (e.g., following administration of about 1 mg, about 2 mg, about 6 mg, or 9 mg of an anti-NGF antibody or antigen-binding fragment thereof).

The Roland Morris Disability Questionnaire: The RMDQ is a self-administered, widely used health status measure for knee and/or hip pain (Roland M O, Morris R W, Spine 1983; 8: 141-144). It measures pain and function, using 24 items describing limitations to everyday life that can be caused by knee and/or hip pain. The score of the RMDQ is the total number of items checked—i.e. from a minimum of 0 to a maximum of 24. The Roland-Morris disability questionnaire is constructed by choosing statements from the sickness impact profile (SIP), which is a 136-item health status measure covering a range of aspects of daily living about physical and mental function. The scale consists of 24 yes/no items related specifically to physical functions to specifically assess the disability from knee and/or hip pain. The physical functions considered include walking, bending over, sitting, lying down, dressing, sleeping, self-care and daily activities. Patients are asked whether the statements apply to them that day (i.e. the last 24 h). In the scale, one point is given for each item. The RDQ score can be obtained by adding up the number of items checked. The final score ranges from 0 (no disability) to 24 (severe disability). According to certain embodiments of the present invention, administration of an NGF antagonist to a patient results in a decrease in RMDQ score. For example, the present invention includes therapeutic methods which result in a decrease from baseline in RMDQ score of at least about 2 to 5 points for a moderate improvement and greater than 5 points to be considered a large, or substantial improvement at week 2, 4, 8, 12 and 16, or later following administration of the NGF antagonist (e.g., following administration of about 6 mg, or 9 mg of an anti-NGF antibody or antigen-binding fragment thereof).

Patient Global Assessment of knee and/or hip pain: The PGA of knee and/or hip pain is a patient-rated assessment of their current disease state on a 5-point Likert scale (1=very well; 2=well; 3=fair; 4=poor; and 5=very poor). According to certain embodiments of the present invention, administration of an NGF antagonist to a patient results in a decrease in PGA of knee and/or hip pain score. For example, the present invention includes therapeutic methods which result in a decrease from baseline in PGA of knee and/or hip pain score of at least about 1 point, or 2 points, or 3 points or more at week 2, 4, 8, 12 and 16, or later following administration of the NGF antagonist (e.g., following administration of about 6 mg, or 9 mg of an anti-NGF antibody or antigen-binding fragment thereof).

Short Form (36) Health Survey: The SF-36 is a self-administered survey of general health. It measures 8 domains of health: physical functioning, role limitations due to physical health, bodily pain, general health perceptions, vitality, social functioning, role limitations due to emotional problems, and mental health. It yields scale scores for each of these 8 health domains, and 2 summary measures of physical and mental health: the physical component summary and the mental component summary Each scale is directly transformed into a 0-100 scale on the assumption that each question carries equal weight. The lower the score the more disability. The higher the score the less disability i.e., a score of zero is equivalent to maximum disability and a score of 100 is equivalent to no disability. According to certain embodiments of the present invention, administration of an NGF antagonist to a patient results in an increase in SF-36 score. For example, the present invention includes therapeutic methods which result in an increase from baseline in SF-36 score of at least about 10%, 20%, 30%, 40%, 50%, or more at week 2, 4, 8, 12 and 16, or later following administration of the NGF antagonist (e.g., following administration of about 6 mg, or 9 mg of an anti-NGF antibody or antigen-binding fragment thereof).

Medical Outcomes Study Sleep Survey: The MOS Sleep Survey is a self-administered 12-question survey of sleep habits (Hays R D, Stewart A L (1992). Sleep measures. In A. L. Stewart & J. E. Ware (eds.), Measuring functioning and well-being: The Medical Outcomes Study approach (pp 235-259), Durham, N.C.: Duke University Press). According to certain embodiments of the present invention, administration of an NGF antagonist to a patient results in an improvement in the MOS Sleep Survey from baseline. For example, the present invention includes therapeutic methods which result in a change from baseline in the MOS Sleep Survey at week 2, 4, 8, 12 and 16, or later following administration of the NGF antagonist (e.g., following administration of about 6 mg, or 9 mg of an anti-NGF antibody or antigen-binding fragment thereof).

EQ-5D-5L: The EQ-5D-5L is a standardized measure of health status developed by the EuroQol Group to provide a simple, generic measure of health for clinical and economic appraisal. The EQ-5D-5L, as a measure of health-related quality of life, defines health in terms of 5 dimensions: mobility, self-care, usual activities, pain/discomfort, anxiety/depression. Each dimension has 3 ordinal levels of severity: "no problem" (1), "some problems" (2), "severe problems" (3). Overall health state is defined as a 5-digit number. Health states defined by the 5-dimensional classification can be converted into corresponding index scores that quantify health status, where −0.594 represents "severe problems" and 1 represents "no problem." According to certain embodiments of the present invention, administration of an NGF antagonist to a patient results in an improvement in the EQ-5D-5L from baseline. For example, the present invention includes therapeutic methods which result in a change from baseline in the EQ-5D-5L at week 2, 4, 8, 12 and 16, or later following administration of the NGF antagonist (e.g., following administration of about 6 mg, or 9 mg of an anti-NGF antibody or antigen-binding fragment thereof).

Additional details for various methods for assessing pain, non-responsiveness or intolerance to analgesics and the like are disclosed in US20180147280, which is herein incorporated by reference in its entirety.

NGF Antagonists

As disclosed in detail above, the present invention includes methods, which comprise administering to a subject in need thereof a therapeutic composition comprising an NGF antagonist. As used herein, an "NGF antagonist" is any agent, which binds to or interacts with NGF and inhibits the normal biological function of NGF when NGF is expressed on a cell in vitro or in vivo. Non-limiting examples of categories of NGF antagonists include small molecule NGF antagonists, anti-NGF aptamers, peptide-based NGF antagonists (e.g., "peptibody" molecules), and antibodies or antigen-binding fragments of antibodies that specifically bind human NGF.

The terms "NGF," "hNGF," and the like, as used herein, are intended to refer to nerve growth factor, and in particular, to human nerve growth factor, the amino acid sequence of which is shown as SEQ ID NO: 18 and which is encoded by the nucleic acid sequence shown as SEQ ID NO: 17. Unless specifically designated as being from a non-human species, the term "NGF", as used herein, shall be understood to mean human NGF.

The term "antibody," as used herein, is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-NGF antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, may be adapted for use in the context of an antigen-binding fragment of an antibody of the present invention using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody," as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The term "human antibody", as used herein, is intended to include non-naturally occurring human antibodies. The term includes antibodies that are recombinantly produced in a non-human mammal, or in cells of a non-human mammal. The term is not intended to include antibodies isolated from or generated in a human subject.

The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" NGF, as used in the context of the present invention, includes antibodies that bind NGF or portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM, less than about 0.5 nM, less than 0.1 nM, less than 1.0 pM, or less than 0.5 pM, as measured in a surface plasmon resonance assay. An isolated antibody that specifically binds human NGF may, however, have cross-reactivity to other antigens, such as NGF molecules from other (non-human) species.

The anti-NGF antibodies useful for the methods of the present invention may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes methods involving the use of antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present invention.

The present invention also includes methods involving the use of anti-NGF antibodies comprising variants of any of the HCVR, LCVR, and/or CDR amino acid sequences disclosed herein having one or more conservative substitutions. For example, the present invention includes the use of anti-NGF antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "surface plasmon resonance," as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "KD," as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

Preparation of Human Antibodies

Methods for generating human antibodies in transgenic mice are known in the art. Any such known methods can be used in the context of the present invention to make human antibodies that specifically bind to human NGF.

Using VELOCIMMUNE™ technology (see, for example, U.S. Pat. No. 6,596,541, Regeneron Pharmaceuticals) or any other known method for generating monoclonal antibodies, high affinity chimeric antibodies to NGF are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. The antibodies are characterized and selected for desirable characteristics, including affinity, selectivity, epitope, etc, using standard procedures known to those skilled in the art. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies that can be used in the methods of the present invention possess high affinities, as described above, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Specific examples of human antibodies or antigen-binding fragments of antibodies that specifically bind NGF which can be used in the context of the methods of the present invention include any antibody or antigen-binding fragment which comprises the three heavy chain CDRs (HCDR1, HCDR2 and HCDR3) contained within a heavy chain variable region (HCVR) having an amino acid sequence consisting of SEQ ID NO: 2. The antibody or antigen-binding fragment may comprise the three light chain CDRs (LCVR1, LCVR2, LCVR3) contained within a light chain variable region (LCVR) having an amino acid sequence consisting of SEQ ID NO: 10. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In certain embodiments of the present invention, the antibody or antigen-binding fragment thereof comprises the six CDRs (HCDR1, HCDR2, HCDR3, LCDR1, LCDR2 and LCDR3) from the heavy and light chain variable region amino acid sequence pairs (HCVR/LCVR) of SEQ ID NOs: 2/10.

In certain embodiments of the present invention, the antibody or antigen-binding fragment thereof comprises six CDRs (HCDR1/HCDR2/HCDR3/LCDR1/LCDR2/LCDR3) having the amino acid sequences consisting of SEQ ID NOs: 4/6/8/12/14/16.

In certain embodiments of the present invention, the antibody or antigen-binding fragment thereof comprises HCVR/LCVR amino acid sequence pairs consisting of SEQ ID NOs: 2/10.

As used herein, the term "Fasinumab" is used interchangeably to refer to an anti-NGF antibody. The amino acid sequences of the heavy chain and light chain variable regions and the CDRs portions as well as the nucleotide sequences of Fasinumab are described in Tables 1A and 1B, respectively. The characterization of Fasinumab is described in PCT Publication No. WO 2009/023540 and WHO Drug Information Vol. 26, No. 2, (2012), which are all hereby incorporated by reference in their entirety. Tables 1A and 1B list amino acid SEQ ID NOs and the nucleic acid SEQ ID NOs for an anti-NGF antibody disclosed herein:

TABLE 1A

| Antibody Designation | AMINO ACID SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| Fasinumab | 2 | 4 | 6 | 8 | 10 | 12 | 14 | 16 |

TABLE 1B

| Antibody Designation | NUCLEIC ACID SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| Fasinumab | 1 | 3 | 5 | 7 | 9 | 11 | 13 | 15 |

Pharmaceutical Compositions

The present invention includes methods, which comprise administering an NGF antagonist to a patient, wherein the NGF antagonist is contained within a pharmaceutical composition. The pharmaceutical compositions of the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient according to the methods of the present invention may vary depending upon the age and the size of the patient, symptoms, conditions, route of administration, and the like. The dose is typically calculated according to body weight or body surface area. Depending on the severity of the condition, the frequency and the duration of the treatment can be adjusted. Effective dosages and schedules for administering pharmaceutical compositions comprising anti-NGF antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351). Specific exemplary doses of anti-IL4R antibodies, and administration regimens involving the same, that can be used in the context of the present invention are disclosed elsewhere herein.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-NGF antibody that can be used in the context of the present invention are disclosed. Examples of useful antibodies are disclosed in International Publication No. WO 2018/102294, U.S. Pat. No. 7,988,967, and U.S. Patent Application Publication No. 2012/0097565. Further, useful formulations comprising the antibodies are disclosed in U.S. Patent Application Publication No. US 2012/0014968. All of which are incorporated herein by reference.

Dosage

The amount of NGF antagonist (e.g., anti-NGF antibody) administered to a subject according to the methods of the present invention is, generally, a therapeutically effective amount. As used herein, the phrase "therapeutically effective amount" means an amount of NGF antagonist that results in one or more of: (a) an improvement in one or more pain-associated parameters (as defined elsewhere herein); and/or (b) a detectable improvement in one or more symptoms or indicia of pain. A "therapeutically effective amount" also includes an amount of NGF antagonist that inhibits, prevents, lessens, or delays the progression of pain in a subject.

In the case of an anti-NGF antibody, a therapeutically effective amount can be from about 0.05 mg to about 600 mg, e.g., about 0.05 mg, about 0.1 mg, about 1.0 mg, about 1.5 mg, about 2.0 mg, about 3.0 mg, about 6.0 mg, about 9.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-NGF antibody. In certain embodiments, about 1 mg-10 mg of an anti-NGF antibody is administered to a subject. In certain embodiments, about 1 mg, 3 mg, 6 mg, or 9 mg of an anti-NGF antibody is administered to a subject. In certain cases, the anti-NGF antibody includes the CDRs disclosed herein. In certain aspects, the anti-NGF antibody is fasinumab.

The amount of NGF antagonist contained within the individual doses may be expressed in terms of milligrams of antibody per kilogram of patient body weight (i.e., mg/kg). For example, the NGF antagonist may be administered to a patient at a dose of about 0.0001 to about 10 mg/kg of patient body weight. For example, the NGF antagonist may be administered to a patient at a dose of about 0.03 to about 3 mg/kg of patient body weight. For example, the NGF antagonist may be administered to a patient at a dose of about 0.03 to about 3 mg/kg of patient body weight.

Combination Therapies

The methods of the present invention, according to certain embodiments, comprise administering to the subject one or more additional therapeutic agents in combination with the NGF antagonist. As used herein, the expression "in combination with" means that the additional therapeutic agents are administered before, after, or concurrent with the pharmaceutical composition comprising the NGF antagonist. The term "in combination with" also includes sequential or concomitant administration of NGF antagonist and a second therapeutic agent.

For example, when administered "before" the pharmaceutical composition comprising the NGF antagonist, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes or about 10 minutes prior to the administration of the pharmaceutical composition comprising the NGF antagonist. When administered "after" the pharmaceutical composition comprising the NGF antagonist, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours or about 72 hours after the administration of the pharmaceutical composition comprising the NGF antagonist. Administration "concurrent" or with the pharmaceutical composition comprising the NGF antagonist means that the additional therapeutic agent is administered to the subject in a separate dosage form within less than 5 minutes (before, after, or at the same time) of administration of the pharmaceutical composition comprising the NGF antagonist, or administered to the subject as a single combined dosage formulation comprising both the additional therapeutic agent and the NGF antagonist.

The additional therapeutic agent may be, e.g., another NGF antagonist (e.g. see the NGF antibodies described in U.S. Pat. No. 7,449,616 (tanezumab); U.S. Pat. Nos. 7,569,364; 7,655,232; 8,088,384; WO2011049758 (fulranumab)), an IL-1 antagonist (including, e.g., an IL-1 antagonist as set forth in U.S. Pat. No. 6,927,044), an IL-6 antagonist, an IL-6R antagonist (including, e.g., an anti-IL-6R antibody as set forth in U.S. Pat. No. 7,582,298), an opioid, acetaminophen, a local anesthestic, an NMDA modulator, a cannabinoid receptor agonist, a P2X family modulator, a VR1 antagonist, a substance P antagonist, a $Na_v1.7$ antagonist, a cytokine or cytokine receptor antagonist, an antiepileptic drug, a steroid, other inflammatory inhibitors such as inhibitors of caspase-1, p38, IKK1/2, CTLA-4Ig and a corticosteroid.

Administration Regimens

The present invention includes methods comprising administering to a subject a pharmaceutical composition comprising an NGF antagonist at a dosing frequency of about four times a week, twice a week, once a week, once every two weeks, once every three weeks, once every four weeks, once every five weeks, once every six weeks, once every eight weeks, once every twelve weeks, or less frequently so long as a therapeutic response is achieved. In certain embodiments involving the administration of a pharmaceutical composition comprising an anti-NGF antibody, such as fasinumab, once every 4 weeks dosing at an amount of about 1, 3, 6, or 9 mg, can be employed. In certain embodiments involving the administration of a pharmaceutical composition comprising an anti-NGF antibody, such as fasinumab, once every 8 weeks dosing at an amount of about 1, 3, 6, or 9 mg, can be employed. In certain embodiments involving the administration of a pharmaceutical composition comprising an anti-NGF antibody, such as fasinumab, once every 12 weeks dosing at an amount of about 1, 3, 6, or 9 mg, can be employed.

According to certain embodiments of the present invention, multiple doses of an NGF antagonist may be administered to a subject over a defined time course. The methods according to this aspect of the invention comprise sequentially administering to a subject multiple doses of an NGF antagonist. As used herein, "sequentially administering" means that each dose of NGF antagonist is administered to the subject at a different point in time, e.g., on different days separated by a predetermined interval (e.g., hours, days, weeks or months). The present invention includes methods which comprise sequentially administering to the patient a single initial dose of an NGF antagonist, followed by one or more secondary doses of the NGF antagonist, and optionally followed by one or more tertiary doses of the NGF antagonist.

The terms "initial dose," "secondary doses," and "tertiary doses," refer to the temporal sequence of administration of the NGF antagonist. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of NGF antagonist, but generally may differ from one another in terms of frequency of administration. In certain embodiments, however, the amount of NGF antagonist contained in the initial, secondary and/or tertiary doses varies from one another (e.g., adjusted up or down as appropriate) during the course of treatment. In certain embodiments, one or more (e.g., 1, 2, 3, 4, or 5) doses are administered at the beginning of the treatment regimen as "loading doses" followed by subsequent doses that are administered on a less frequent basis (e.g., "maintenance doses"). For example, an NGF antagonist may be administered to a patient with low back pain at a loading dose equivalent to 2 times the maintenance dose. Accordingly, if the maintenance dose is 3 mg, the loading dose will be 6 mg. If the maintenance dose is 6 mg, the loading dose is 12 mg. If the maintenance dose is 9 mg, the loading dose is 18 mg. Accordingly, it is envisioned that a loading dose of about 6 mg, 12 mg, or 18 mg, followed by one, two, or more maintenance doses of about 3 mg, 6 mg, or 9 mg respectively, may be sufficient to achieve a change from baseline in at least one pain parameter as noted herein.

In one exemplary embodiment of the present invention, each secondary and/or tertiary dose is administered 1 to 16 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, or more) weeks after the immediately preceding dose. In one exemplary embodiment of the present invention, each secondary and/or tertiary dose is administered every 4, 8, or 12 weeks after the immediately preceding dose. The phrase "the immediately preceding dose," as used herein, means, in a sequence of multiple administrations, the dose of NGF antagonist, which is administered to a patient prior to the administration of the very next dose in the sequence with no intervening doses.

The methods according to this aspect of the invention may comprise administering to a patient any number of secondary and/or tertiary doses of an NGF antagonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose, or 4 to 8 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes methods comprising sequential administration of an NGF antagonist and a second therapeutic agent, to a patient to treat osteoarthritis pain. In some embodiments, the present methods comprise administering one or more doses of an NGF antagonist followed by one or more doses of a second therapeutic agent. For example, one or more doses of about 1 mg to about 20 mg of the NGF antagonist may be administered after which one or more doses of a second therapeutic agent (e.g., acetaminophen, or an opioid or any other therapeutic agent, as described elsewhere herein) may be administered to treat, alleviate, reduce or ameliorate one or more symptoms of osteoarthritis pain. In some embodiments, the NGF antagonist is administered at one or more doses resulting in an improvement in one or more pain-associated parameters followed by the administration of a second therapeutic agent to prevent recurrence of at least one symptom of osteoarthritis pain. Alternative embodiments of the invention pertain to concomitant administration of an NGF antagonist and a second therapeutic agent. For example, one or more doses of an NGF antagonist are administered and a second therapeutic agent is administered at a separate dosage at a similar or different frequency relative to the NGF antagonist. In some embodiments, the second therapeutic agent is administered before, after or concurrently with the NGF antagonist.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Patients and Methods

Patients. Eligible patients were 40-80 years of age; had a diagnosis of OA of the knee and/or hip (designated the most symptomatic, index joint at the time of the screening visit) based on the American College of Rheumatology criteria for OA with radiologic confirmation (Kellgren-Lawrence [K-L] grading of ≥2 on a scale of 0-4); and demonstrated moderate-to-severe pain in the index joint, defined as a Western Ontario and McMaster Universities Osteoarthritis Index (WOMAC) pain subscale score of ≥4, at both the screening while on usual analgesic medication and at the randomization visit, which occurred 7 days after withdrawal of analgesic therapy. Patients were required to have a history of inadequate pain relief with or intolerance to acetaminophen and ≥1 oral NSAID, and a history of inadequate pain relief with, intolerance to, or unwillingness to use opioids. Patients were also required to have a history of regular analgesic use for OA pain (average of 4 days/week during the 4 weeks prior to screening). Patients were excluded if they had a history of other joint diseases, trauma to the index joint within 30 days prior to screening, active fibromyalgia or another moderate-to-severe pain condition, or a body mass index >39.

Study design. This phase IIb/III double-blind, placebo-controlled study was conducted at 61 sites in the United States. Patients were randomized (1:1:1:1:1) to receive fasinumab 1 mg, 3 mg, 6 mg, or 9 mg or placebo administered subcutaneously every 4 weeks for a total of 4 doses over a 16-week treatment period (FIG. 1). To ensure balanced treatment assignment across joints and OA severity, randomization was stratified by index joint (knee or hip) and K-L scores (2-3 vs 4). After the treatment period, patients were followed for an additional 20 weeks, resulting in a 36-week study period. Efficacy and safety assessments were performed at each study visit through week 36. Additional safety data were captured via telephone survey at weeks 24 and 32.

Patients were required to stop use of analgesic medications at a pre-randomization visit, 7 days before randomization. Pain and global assessment scores were obtained before and after withdrawal of previous analgesic medication. Although these scores had to meet a pain threshold (≥4 points on a scale of 10), there was no requirement for pain flare.

Beginning at the pre-randomization period (during withdrawal of prior analgesic therapy) and continuing through week 20, patients were allowed to take study-provided rescue analgesic medication (1-2 tablets of acetaminophen 325 mg every 4 to 6 hours, as needed for intolerable pain, with a maximum of 8 tablets or 2600 mg per day), which was discontinued ≥48 hours prior to the start of each study visit through week 16. Patients could have received opioids only after completion of the week 16 visit, if deemed necessary by the investigator. Patients were not allowed to use any NSAID (oral or topical, except aspirin ≤100 mg/day for cardiac prophylaxis) until ≥16 weeks after the last dose of study drug (week 28).

An independent data monitoring committee periodically reviewed all unblinded data and made recommendations as necessary, to the sponsor which remained blinded, as to the conduct of the study. This study was conducted in accordance with the ethical principles that have their origin in the Declaration of Helsinki and that are consistent with the International Council for Harmonisation guidelines for Good Clinical Practice and applicable regulatory requirements. Informed consent was obtained from each patient prior to enrollment.

Efficacy endpoints. The primary efficacy endpoint was the change from baseline to week 16 in the WOMAC pain subscale score (a composite index of 5 questions related to joint pain while walking, using stairs, at rest in bed, sitting or lying, and standing) (Bellamy N. London, Ontario, Canada: Victoria Hospital; 1995). Individual WOMAC questions were scored on a scale of 0-10. The scores from each of the 5 questions were averaged. Average placebo-adjusted improvements with fasinumab in WOMAC pain subscale (Bellamy N. London, Ontario, Canada: Victoria Hospital; 1995) were evaluated across treatment groups.

Secondary efficacy endpoints were change from baseline to week 16 in the WOMAC physical function subscale score (scale, 0-68; arithmetically converted to a scale of 0-10; Bellamy N. London, Ontario, Canada: Victoria Hospital; 1995) and Patient Global Assessment (PGA) score (a single question on a scale of 1-5, with worst assessment being the highest score (Strand V, Kellman A Curr Rheumatol Rep 2004: 6:20-30).

Exploratory efficacy endpoints included daily and weekly (average of daily scores over the preceding week) walking index joint pain score on the Numeric Rating Scale (NRS; scale 0-10; 0=no pain; MCID: ~1 point) (Salaffi F, et al. Eur J Pain 2004; 8:283-91); the percentage of patients who responded at week 16 in the WOMAC pain and physical function subscale scores (defined as ≥30% and ≥50% reductions); the rate of response using the Outcome Measures for Rheumatology Committee and Osteoarthritis Research Society International Standing Committee for Clinical Trials Response Criteria Initiative (OMERACT-OARSI) responder index (an 11-item tool that measures knee or hip OA pain) (Pham T, et al. J Rheumatol 2003; 30:1648-54); and quality of life assessed using the short form-36 (SF-36) health survey (Ware J E Jr, et al. Med Care 1992; 30:473-83) and EuroQol-5 Dimension-5 Level (EQ-5D-5L) scale utility index score (van Reenen M, et al. Rotterdam, The Netherlands: European Quality of Life Research Foundation; April 2015). An additional exploratory analysis was performed to assess response to fasinumab according to the presence or absence of pain flare after discontinuation of prior analgesic therapy, defined by thresholds of change in pain scores from pre-randomization to randomization of −1, −1.5, and −2 points on the 10-point WOMAC pain subscale.

Safety endpoints. Safety was evaluated by assessing treatment-emergent adverse events (TEAEs), adverse events of special interest (adjudicated arthropathy and sympathetic nervous system dysfunction), and hematological and serum chemistry laboratory tests.

Given that an increased risk of joint adverse events has been reported in clinical trials with anti-NGF antibodies (Miller R E, et al. Clin Exp Rheumatol 2017; 35 Suppl 107:85-7; Kumar V, Mahal B A. J Pain Res 2012; 5:279-87; and Hochberg M C. Osteoarthritis Cartilage 2015:23 Suppl 1; S18-21), adjudicated arthropathy, an umbrella term for rapidly progressive OA (type 1: joint space narrowing exceeding pre-specified thresholds and type 2: changes in bone structure on plain film), subchondral insufficiency fracture, and primary osteonecrosis, was assessed by an independent, a blinded committee composed of 3 radiologists. Joint safety was monitored in all subjects via plain radiographs of the shoulders, hips and knees at screening, at the end of the treatment period (week 16), and at the end of the study (week 36). Imaging was also conducted at any time during the study for worsening joint pain that the investigator assessed as inconsistent with the patient's normal pain due to OA. Magnetic resonance imaging (MRI) was performed at baseline of the index and contralateral joint, and of any joint with K-L score at baseline of ≥3. Additional MRIs were performed if follow-up radiographs were deemed to exhibit important interval changes.

Subjects were also monitored for sympathetic nervous system dysfunction using prespecified criteria, which included an autonomic dysfunction questionnaire and thresholds for changes in blood pressure or heart rate upon positional provocation (Strand V, Kellman A. Curr Rheumatol Rep 2004: 6:20-30).

Statistical analysis. It was estimated that 375 patients would be required to be randomized in balanced allocation to the 5 treatment arms, based on assumptions of treatment effect to minimize type 1 error to 0.05, a statistical power of ≥85%, and a detectable difference for the primary endpoint of >1.1 (active vs. placebo). A combination of Hochberg procedure (Hochberg M C, et al. Arthritis Rheumatol 2016; 68 (2): 382-391) and gatekeeping method was used to address multiplicity across treatment groups, by applying Hochberg method to test first the 6-mg and 9-mg doses, at an alpha of 0.05. Only if both tests passed this threshold, would the testing of the 3-mg and 1-mg doses versus placebo be performed in sequence, each at a 0.05 level of significance. If 1 of the 2 highest doses failed the 0.05 level of significance, the smaller p-value would be compared with 0.025 level of significance. If both the 6-mg and 9-mg doses were not statistically significantly better than placebo (0.05 threshold), further testing according to the pre-specified hierarchy was not allowed.

Efficacy variables were analyzed using a mixed-effects model repeated measure (MMRM) approach. The model included randomization strata (K-L score 2 or 3 vs. 4) and index joint, baseline score, treatment and treatment-by-visit interaction. The least squares (LS) means for the change from baseline to week 16, as well as the LS mean differences between fasinumab doses and placebo, with their corresponding standard errors (SEs), P values, and 95% confidence intervals (CIs), were provided from the MMRM.

Results

Patient disposition. A total of 1,214 patients were screened, 421 were randomized to receive fasinumab (n=338) or placebo (n=83; FIG. 1). Of the 421 randomized patients, 419 patients received ≥1 dose of study medication (1 patient each, randomized to placebo and fasinumab 9 mg, discontinued before study drug administration). A total of 342 patients completed the entire 36-week study period (fasinumab: n=294; 87%; placebo: n=67; 81%).

Patient demographics and baseline characteristics. Patient demographics and baseline characteristics were generally balanced across the treatment groups (FIG. 42). Most patients (66%) had K-L scores of 3 or 4 for the hip or knee. Most of the index joints (88%) were knee joints.

Efficacy. All four doses of fasinumab demonstrated significantly greater reductions from baseline at week 16 in WOMAC pain subscale scores than placebo. The LS mean difference over placebo for treatment groups ranged from −0.78 to −1.40, exceeding the published MCID (for an individual patient: 0.67-0.75 points), with the greatest difference observed with the 9-mg dose (FIG. 43). Reductions in pain subscale scores were evident by week 2 across fasinumab doses and were maintained throughout the 16-week treatment period (FIG. 47(A)). During the follow-up period (after week 16), pain scores returned to baseline levels, though not fully, for each fasinumab dose. To assess the robustness of this intention-to-treat approach, a per-protocol analysis was performed, which provided similar results (data not shown). Subgroup analyses for WOMAC pain subscale scores by K-L Score (FIG. 50(A)), age (FIG. 50(B)), sex (FIG. 50(C)), race, index joint, weight, and body mass index (BMI) were generally consistent with results from the overall population.

Additionally, all 4 doses of fasinumab demonstrated statistically significant and clinically meaningful reductions from baseline at week 16 in WOMAC physical function subscale scores compared with placebo, with an incomplete return to baseline values, paralleling the changes noted for the WOMAC pain subscale (FIG. 47(B); FIG. 48). Across all doses, fasinumab was also associated with greater numerical reductions from baseline at week 16 in PGA scores than placebo, reaching statistical significance for the 1-mg and 9-mg doses (>30% improvement; P values: 0.0132 and 0.008, respectively). PGA scores returned to baseline levels in the follow-up period.

Fasinumab resulted in clinical benefit across most exploratory endpoints, although these analyses were not specifically powered for comparisons. Statistically significant and clinically meaningful reductions in NRS walking pain were noted by week 2 and maintained over the course of the 16-week treatment period across fasinumab doses (FIG. 51).

In the responder analysis substantial treatment effects, defined as ≥30% improvement from baseline, were noted in greater proportions of patients receiving any of the 4 fasinumab doses than in those receiving placebo in the WOMAC pain subscale scores (63.5%-73.8% vs 47% for placebo) and WOMAC physical function subscale scores (61.2%-71.4% vs 44.6% for placebo). Similar results were demonstrated for ≥50% improvement from baseline, achieving statistical significance for all 4 doses at week 16. In the responder analysis based on the OMERACT-OARSI responder index, greater proportions of patients receiving any of the 4 fasinumab doses exhibited clinically meaningful treatment responses compared with those receiving placebo (72.9%, 72.6%, 63.5%, and 78.6% for 1-mg, 3-mg, 6-mg, and 9-mg doses, respectively, vs 51.8% for placebo; P<0.01 for all except the 6-mg dose).

WOMAC pain subscale scores were also assessed in patients with or without a pain flare upon withdrawal of analgesic medication prior to randomization. Across fasinumab doses, patients with a pain flare had worse baseline mean pain scores compared with those without a pain flare. The proportion of patients randomized to fasinumab treatment who had experienced a previous pain flare (scores ≥1 on a scale of 0-10) was approximately 25% across doses. Placebo-adjusted improvements in mean pain scores at week 16 with fasinumab ranged from −1.12 to −1.81 in patients with a pain flare (FIG. 47(C)) and from −0.87 to −1.14 in patients without a flare (FIG. 47(D)). Patients with a pain flare compared with those without a pain flare randomized to receive placebo showed a larger degree of improvement (−3.68 vs −2.19). Similar trends were noted using higher pain thresholds, but were based on smaller numbers of observations. Greater treatment effects were observed in patients with higher baseline pain scores or who exhibited greater worsening on withdrawal of prior analgesic therapy.

Results for the SF-36 health survey instrument showed quality-of-life improvements for all 4 fasinumab doses compared with placebo for pain and functioning scales, including bodily pain and physical functioning (data not shown). However, consistent improvements were not observed with the other scales (i.e., general health, social functioning, role-emotional, mental health, vitality, and mental component scores). Quality-of-life improvements were also demonstrated using the EQ-5D-5L utility index score (FIG. 49).

Safety. The mean (SD) duration of treatment was similar in placebo (101 (26)) and the pooled fasinumab groups (105 (20)). The mean (SD) duration of observation was similar (219 (75) days, placebo group and 236. (54) days, fasinumab). The safety analysis set included 419 patients, 82 receiving placebo and 337 receiving fasinumab.

During the 16-week treatment period, the incidence of treatment-related, treatment-emergent adverse events (TE-AEs) was 17% in the fasinumab group and 10% in the placebo group (FIG. 44). Nervous system and musculoskeletal symptoms were more frequent for patients treated with fasinumab than with placebo (7% vs 4% and 3% vs 2%, respectively). The combined fasinumab group, compared with the placebo group, had slightly higher incidences of paresthesia (2% vs 0%) and similar incidences of hypoesthesia (1% each) and arthralgia (1% each). Across all treatment groups, the majority of adverse events were mild-to-moderate in severity. The incidence of serious TEAEs during the treatment period was low, but slightly higher in the placebo group than in the combined fasinumab group (2% vs 1%). There was no apparent dose relationship with fasinumab in the proportion of patients with serious TEAEs. A small proportion of patients discontinued therapy because of TEAEs during the treatment period in both the fasinumab and placebo groups (4% [n=14] and 1% [n=1]). No group exhibited an identifiable or predominant cause for discontinuation, which spanned musculoskeletal/connective tissue (2% and 1%), nervous system (paresthesia: 1% and 0%; hypoesthesia: 1% and 0%), and skin and subcutaneous tissue disorders (1% and 0%) in combined fasinumab and placebo groups, respectively.

During the 20-week follow-up period, the incidence of TEAEs was higher in the combined fasinumab group than in the placebo group (8% vs 4%; FIG. 44), as was the incidence of serious TEAEs (6% vs 5%). The incidence of serious TEAEs during the follow-up period was higher in those who had been randomized to the 9-mg dose (8%) than the 1-mg (6%), 3-mg (4%), or 6-mg (6%) doses.

Arthropathies were detected in 23 (5%) patients overall, involving 25 joints, occurring in 7% and 1% of patients in the combined fasinumab and placebo groups, respectively (FIG. 45). Arthropathies consisted of rapidly progressive OA, in 5% of patients in the fasinumab group (the majority of these were joint space narrowing without evidence of change in bone structure) and in none of the patients in the placebo group, and subchondral insufficiency fracture, occurring in 2% and 1% of patients in the respective groups. No primary osteonecrosis was observed. An increase in arthropathies was observed with fasinumab dose and time during the study.

Of the adjudicated arthropathies, in a post-hoc analysis, destructive arthropathy, categorized as new bone fragmentation, destruction, or fracture over the study period, near-total or total collapse of an articular surface, and subluxation/malalignment, all features inconsistent with expected radiographic findings in conventional OA, was assessed. Destructive arthropathy was observed in two patients (<1% of 338 fasinumab treated subjects): one (1) in the 6 mg and one (1) in the 9 mg treatment groups.

Overall, 16 (4%) patients underwent 18 total joint replacements, which occurred in 4% of patients in the fasinumab group and 2% of patients in the placebo group (FIG. 45). There was no apparent fasinumab dose relationship for total joint replacements.

There was no indication of sympathetic nervous system dysfunction. Routine monitoring of laboratory tests revealed no significant change, with the exception of alkaline phosphatase (ALP), which increased in a time- and dose-related fashion over the course of the trial, but remained within normal range. In follow-up, mean ALP values decreased by week 36, though had not returned to baseline. There were no deaths during the study.

Discussion

In this phase study involving patients with moderate-to-severe OA, fasinumab was superior to placebo for improving pain and physical function. Patients receiving fasinumab, compared with those receiving placebo, demonstrated statistically significant and clinically important reductions in WOMAC pain subscale scores. Placebo-adjusted group mean improvements in WOMAC pain subscale scores ranged from 0.78 to 1.40 points, exceeding the MCID (Bellamy N. London, Ontario, Canada: Victoria Hospital; 1995). Responder analyses for thresholds of ≥30% and ≥50% reductions in WOMAC pain subscale scores confirmed that a substantially greater proportion of patients receiving fasinumab achieved threshold improvements in pain than those receiving placebo. Improvements in WOMAC physical function subscale scores were also statistically significant and clinically important with fasinumab compared with placebo. Furthermore, notable relief of pain walking was achieved within 7 days of initiation of fasinumab therapy across all 4 doses, as evidenced by NRS scores (Salaffi F, et al. Eur J Pain 2004; 8:283-91).

Fasinumab reduced pain, as demonstrated by the WOMAC pain subscale score and NRS pain scores. WOMAC physical function also revealed improvements, as did the PGA, indicating that impact of the illness was reduced. Efficacy was observed at all doses evaluated with no obvious dose relationship across 1 mg, 3 mg, and 6 mg doses. The 9 mg dose demonstrated the greatest treatment effect. Functional fasinumab concentrations increased with increasing dose in an approximately dose-proportional manner from the 3 mg to the 9 mg dose. Although similar efficacy was achieved for the lowest dose, analysis of efficacy produced by the 1 mg dose revealed slower onset of action in association with lowest serum concentrations. Adverse events in this trial were consistent with what has been previously reported with fasinumab and the class of anti-NGF compounds. The most common AEs affected the Musculoskeletal and Nervous Systems, with frequent events including Arthalgias, Paresthesias, and Hypoesthesias. These events rarely resulted in patients discontinuing from study medication and were generally assessed as mild or moderate in severity. Joint related arthropathy events occurred more commonly in the fasinumab groups in a dose-dependent fashion. Patients randomized to the 9 mg dose group had more joint related arthropathies compared to the other active groups. Of the 25 adjudicated arthropathy events in 23 patients, 1 event occurred in a patient administered placebo. Joint replacement surgery rates were generally similar between placebo- and fasinumab-treated groups; in contrast to arthropathy events, there was no apparent association of dose to rate of joint replacements, although the number of cases was small (2 to 4 per treatment group).

Patients in this study received 16 weeks of treatment. When treatment was withdrawn, patients experienced more arthralgia AEs and experienced increases in their WOMAC pain and physical functions sub-scale scores, consistent with a return of OA signs and symptoms after effective treatment with fasinumab was discontinued. There was not a dose-dependent pattern in the posttreatment arthralgia AE reports and the WOMAC pain subscale score post-treatment had not returned to the baseline levels by week 36, suggesting that patients did not have a rebound effect or a worsening of their underlying OA. With regard to post-treatment effects, there were only small differences at week 36 between placebo and most treatment groups for the various efficacy measures examined with a possible difference only for the 9 mg group, having returned closer to baseline.

The tendency for the 9 mg dose to return to a score still below the original baseline on study entry, but, for some endpoints, higher than the placebo arm, with a reverse dose response amongst the various treatment groups, is consistent with the interpretation that the stronger analgesic effects of higher doses of fasinumab, once withdrawn, result in a greater perception of return of pain from a prolonged state of pain suppression. Since patients on the 9 mg dose experienced marked, sustained relief of pain over a period of 3 to 4 months, the return of pain in these patients would be more noticeable than in patients whose pain relief was less marked.

Supporting this construct is that the placebo arm seems to have accommodated to a new level of chronic pain, that does not change with withdrawal of the ineffective treatment (placebo). Instead, this group seems to have "reset", to a new level of chronic pain.

Improvements in pain and function with fasinumab should be placed in the context of published data for analgesics. A recent meta-analysis across 17 trials in OA showed that acetaminophen, the analgesic of first choice for OA pain, provided very modest pain relief, with a mean improvement of approximately 0.4 points from a baseline of 6 points on the 10-point WOMAC pain subscale (Machado G C, et al. BMJ 2015; 350:h1225). In another analysis (Stam W, et al. Open Rheumatol J 2012; 6:6-20), the effect size of acetaminophen versus placebo (−0.09) was substantially lower than that for any of the studied NSAIDs (ranging from −0.39 to −0.49 for naproxen, ibuprofen, and diclofenac). Effect sizes for celecoxib, the only selective cyclooxygenase (COX)-2 inhibitor available in the United States, were generally less that than those for nonspecific NSAIDs (ranging from −0.11 to −0.34 across dosages). A comprehensive meta-analysis comparing opioids with NSAIDs across 6 studies in OA showed little difference in pain relief between these analgesics (Smith S R, et al. Osteoarthritis Cartilage 2016; 24:962-72). A more recent review arrived at similar conclusions (Berthelot J M, et al. Joint Bone Spine 2015; 82:397-401). In our study, patients receiving fasinumab averaged an improvement of >3.4 on the 10-point WOMAC pain subscale scale (−3.49, −3.39, −3.07, and −3.81 points for the 1-mg, 3-mg, 6-mg, and 9-mg doses, respectively, representing a 50%-58% improvement from baseline); whereas, placebo resulted in a change from baseline of −2.43 (38%). This yielded effect sizes across fasinumab doses of up to 0.47, substantially greater than the effect sizes with acetaminophen, NSAIDs, and opioids.

Most analgesic trials in OA enrolled patients who demonstrated a pain flare on withdrawal of prior analgesic therapy, approximately 10 points on the WOMAC 0-100 pain scale (or 1 point on a 0-10 scale). In contrast, the design of the study allowed enrollment of patients with substantial pain, both at screening and at baseline, without requiring a pain flare after analgesic withdrawal. This allowed enrollment of patients whose pain may not have been adequately treated with an analgesic. Most patients in this study did not exhibit a pain flare after analgesic withdrawal. However, in the subgroup of patients who did exhibit a pain flare by a degree of worsening of ≥1, ≥1.5, or ≥2 points, treatment responses tended to be greater than in those who did not, consistent with the greater magnitude of effect observed in OA trials that have employed a pain flare design (Trijau S, et al. Osteoarthritis Cartilage 2010; 18:1012-8). It has been reported that treatment effects for pain and functional scores in non-pain flare designs may underestimate treatment effects by 37%-50% (Trijau S, et al. Osteoarthritis Cartilage 2010; 18:1012-8). Thus, if this underestimate is taken into consideration, fasinumab may prove to provide even greater pain relief than acetaminophen, NSAIDs, or opioids, in patients with OA pain.

With respect to other anti-NGF antibodies, a proof-of-concept study compared tanezumab, a humanized IgG2 anti-NGF monoclonal antibody administered intravenously at a dose of 10-200 μg/kg (i.e., 0.7-14 mg for a patient weighing 70 kg) on days 1 and 56 with placebo (Lane N E, et al. N Engl J Med 2010; 363:1521-31) employing a flare design. Enrollment was limited to patients whose pain worsened by ≥10 points on the 100-point WOMAC pain subscale compared with the screening value 1 week after withdrawal of prior analgesic medication, assessed at the time of randomization. Average WOMAC scores at randomization ranged from 62.1-69 points. Improvements in scores from baseline with tanezumab ranged from 29 points (50-μg/kg dose) to 44 points (200-μg/kg dose), a net effect versus placebo of 12.8-27.3. The results from a subsequent phase III study with tanezumab, at doses ranging from 2.5 to 10 mg given every 8 weeks also employing a flare design, showed somewhat lower treatment effects (Brown M T, et al. J Pain 2012; 13:790-8).

Fasinumab was generally well tolerated. Although the rate of TEAEs was higher for fasinumab than for placebo, there were few discontinuations of therapy due to TEAEs. Modest increases in alkaline phosphatase of likely bone origin were observed, which were unrelated to arthropathy and largely resolved with fasinumab discontinuation. Elevations in alkaline phosphatase levels may reflect a general stimulatory effect of fasinumab on bone synthesis or perhaps be explained by relief of pain resulting in increase in physical activity (not quantified in this study), which can stimulate bone formation and bone mass (Kerr D, et al. J Bone Miner Res. 1996; 11:218-225, Heinonen A, et al. Lancet. 1996; 348:1343-7). Nervous system and musculoskeletal disorders were more frequent for patients treated with fasinumab than with placebo, similar to the rates previously reported for tanezumab (Hochberg M C. Osteoarthritis Cartilage 2015:23 Suppl 1; S18-21), may be related to NGF inhibition, though few patients discontinued treatment due to alterations of peripheral sensation and there were no cases meeting criteria for sympathetic nerve dysfunction.

The study provided previously unavailable opportunities to assess joint changes across doses in the setting of a clinical trial of an NGF inhibitor. Fasinumab was associated with a dose-dependent greater rate of adjudicated arthropathies than placebo, most notable with the 6-mg and 9-mg doses. Small increases in the rates of adjudicated arthropathies, dominated by joint space narrowing (RPOA-1), were seen at the lower doses of fasinumab compared to rates seen in placebo. Higher rates of all adjudicated arthropathies, including RPOA-2 and DA were observed at the highest two doses studied. Because, to our knowledge, this is to date, the only study to incorporate routine, prospective, intense radiological joint assessment using both plain films and MRI, rates of these adverse events with fasinumab cannot be compared to previous analgesic trials. Despite intense joint monitoring of both symptomatic as well as asymptomatic patients, the rates of destructive arthropathy reported in our study with fasinumab were modest (2 of 338 subjects randomized to active treatment at highest two doses of 6 and 9 mg). These rates were lower than those reported in studies with tanezumab, in which joint events of this type were observed upon retrospective assessment, only after patient referral for joint replacement (Schnitzer T J, Marks J A. Osteoarthritis Cartilage 2015; 23 Suppl 1:S8-17).

In conclusion, in this phase IIb/III study involving >400 patients, the NGF-inhibitor fasinumab demonstrated an unprecedented degree of analgesia in patients with moderate-to-severe pain from OA, even in patients who had not experienced benefits with prior analgesic medications, a patient population previously excluded in most other analgesic studies in osteoarthritis, representing an important unmet medical need. Intensive laboratory and radiographic monitoring of patients during the trial demonstrated that fasinumab was well tolerated by most patients, with a dose-dependent increase in joint-related abnormalities notable at the two highest doses studied. The results provided by this trial guide selection of fasinumab doses likely to produce greatest benefit relative to risk in ongoing and future clinical studies of fasinumab in OA and other pain conditions.

The results are also important in validating the fact that patients enrolled to the study reliably had chronic pain, which returned after fasinumab was discontinued. The results also provide additional support for the relationship of fasinumab dose and degree of pain relief over the first 16 weeks of the study (most evident at the extremes of the dose range, 1 and 9 mg treatment groups), given the reappearance of pain in reverse-dose response order once treatment is withdrawn. In this study, the 1 mg every 4 weeks and 3 mg every 4 weeks doses appeared to provide the best benefit/risk. These doses demonstrated efficacy with a better safety profile compared to the higher doses.

Positive topline results from a phase 3, placebo-controlled study on the use of the NGF antibody described here is provided. The specific active ingredient used is an anti-NGF antibody or the antigen binding fragment thereof comprising a heavy chain variable region (HCVR)/light chain variable region (LCVR) amino acid sequence pair of SEQ id Nos: 2/10. However, the basic methods may be applied to the anti-NGF class of drugs.

The results are of a long-term trial in patients with chronic pain from osteoarthritis of the hip or knee. The primary efficacy analysis at 16 weeks for the antibody treated patients shows they experienced less pain and significantly improved functional ability from baseline as compared to the placebo treated patients which were the co-primary endpoints of the study.

The study identifies doses that maximize efficiency while significantly lessening known safety risks with the anti-NGF class of drugs. The results show the ability to use the NGF antibody as an additional choice in the treatment of pain as opposed to steroidal anti-inflammatories or opioid drugs.

The study involved 646 patients which were treated with the same antibody at different dosing intervals with both groups being treated with 1 mg of the NGF antibody and one group treated every four weeks with another group treated every 8 weeks and both groups compared to placebo. The results demonstrate a consistent efficiency in reduced pain while lessening known safety risks.

| Topline Efficacy Results from Phase 3 Study | | | |
|---|---|---|---|
| | Placebo (n = 214) | Fasinumab 1 mg every 8 weeks (n = 215) | Fasinumab 1 mg every 4 weeks (n = 217) |
| Change in pain at week 16 vs. baseline (LS mean)* | −1.56 | −2.25 (p = 0.0019) | −2.78 (p < 0.0001) |
| Change in physical function at week 16 vs. baseline (LS mean)** | 1.37 | 2.10 (p = 0.0011) | 2.57 (p < 0.0001) |

*Western Ontario and McMaster Osteoarthritis Index (WOMAC) pain subscale score (score range: 0-10);
**WOMAC physical function subscale score (score range: 0-10)

Overall incidence of adverse events (AEs), including serious AEs and joint replacement, was similar across the 1 mg fasinumab groups (every 4 weeks or 8 weeks) and placebo. The fasinumab program incorporates robust radiographic monitoring for potential adjudicated arthropathies, the first of which occurs at Week 24. This was implemented to identify any potential adjudicated arthropathies early, where their clinical sequela would likely be lower. As of the data cut-off for primary efficacy, approximately 80% of patients had completed their Week 24 visit. The placebo-corrected cumulative estimate of any type of adjudicated arthropathy was less than 1.5% at both Week 16 and Week 24. In addition, the vast majority of adjudicated arthropathies were isolated joint space narrowing, called RPOA-1 (rapid progressive OA type 1). No cases of osteonecrosis have been identified to date in this study.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions.

Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

---

What is claimed is:

1. A method of reducing pain, or for improving physical function of a knee joint or a hip joint in a patient suffering from osteoarthritis while avoiding the risk of development of an arthropathy associated with treatment with an anti-nerve growth factor (NGF) antibody, or an antigen-binding fragment thereof that binds specifically to NGF, the method comprising:

diagnosing the patient as non-responsive to analgesic treatment or as suffering from a side-effect from analgesic treatment or as having a prior history of opioid addiction; and administering to the patient a pharmaceutical composition comprising 1.0 mg of an anti-nerve growth factor (NGF) antibody or an antigen binding fragment thereof that binds specifically to NGF wherein the administering is at intervals of every eight weeks;

whereby the pharmaceutical composition reduces pain, or improves physical function in the patient and wherein the occurrence of one or more adverse events in the patient, including development of arthropathy, is reduced relative to patients treated with higher doses of the NGF antibody;

wherein the anti-NGF antibody or the antigen binding fragment thereof comprises a heavy chain variable region (HCVR)/light chain variable region (LCVR) amino acid sequence pair of SEQ ID NOs: 2/10 wherein the subject has a Kellgren-Lawrence [K-L] grading of ≥2 on a scale of 0-4, prior to initiation of the treatment.

2. The method of claim 1 wherein the subject has a Kellgren-Lawrence [K-L] grading of 3 or 4 on a scale of 0-4.

* * * * *

SEQUENCE LISTING

<160> NUMBER OF SEQ ID NOS: 18

<210> SEQ ID NO 1
<211> LENGTH: 357
<212> TYPE: DNA
<213> ORGANISM: Artificial Sequence
<220> FEATURE:
<223> OTHER INFORMATION: synthetic

<400> SEQUENCE: 1
caggtgcagc tggtgcagtc tggggctgag gtgaagaagc ctggggcctc agtgaaggtc      60

| | | | | |
|---|---|---|---|---|
| tcctgcaagg | tttccggatt | caccctcact | gaattatcca | ttcactgggt gcgacaggct | 120 |
| cctggaaaag | ggcttgagtg | gatgggaggt | tttgatcctg | aagatggtga aacaatctac | 180 |
| gcacagaagt | tccagggcag | agtcaccatg | accgaggaca | catctacaga cacagcctac | 240 |
| atggagctga | ccagcctgag | atcggaagac | acggccgtgt | attactgttc aacgattttt | 300 |
| ggagtggtta | ccaactttga | caactggggc | cagggaaccc | tggtcaccgt ctcctca | 357 |

<210> SEQ ID NO 2
<211> LENGTH: 119
<212> TYPE: PRT
<213> ORGANISM: Artificial Sequence
<220> FEATURE:
<223> OTHER INFORMATION: synthetic

<400> SEQUENCE: 2

Gln Val Gln Leu Val Gln Ser Gly Ala Glu Val Lys Lys Pro Gly Ala
1               5                   10                  15
Ser Val Lys Val Ser Cys Lys Val Ser Gly Phe Thr Leu Thr Glu Leu
            20                  25                  30
Ser Ile His Trp Val Arg Gln Ala Pro Gly Lys Gly Leu Glu Trp Met
        35                  40                  45
Gly Gly Phe Asp Pro Glu Asp Gly Glu Thr Ile Tyr Ala Gln Lys Phe
    50                  55                  60
Gln Gly Arg Val Thr Met Thr Glu Asp Thr Ser Thr Asp Thr Ala Tyr
65                  70                  75                  80
Met Glu Leu Thr Ser Leu Arg Ser Glu Asp Thr Ala Val Tyr Tyr Cys
                85                  90                  95
Ser Thr Ile Phe Gly Val Val Thr Asn Phe Asp Asn Trp Gly Gln Gly
            100                 105                 110
Thr Leu Val Thr Val Ser Ser
        115

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
ggattcaccc tcactgaatt atcc                                          24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Thr Leu Thr Glu Leu Ser
1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
tttgatcctg aagatggtga aaca                                                24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Phe Asp Pro Glu Asp Gly Glu Thr
1               5

<210> SEQ ID NO 7
<211> LENGTH: 36
<212> TYPE: DNA
<213> ORGANISM: Artificial Sequence
<220> FEATURE:
<223> OTHER INFORMATION: synthetic

<400> SEQUENCE: 7
tcaacgattt ttggagtggt taccaacttt gacaac                                    36

<210> SEQ ID NO 8
<211> LENGTH: 12
<212> TYPE: PRT
<213> ORGANISM: Artificial Sequence
<220> FEATURE:
<223> OTHER INFORMATION: synthetic

<400> SEQUENCE: 8

Ser Thr Ile Phe Gly Val Val Thr Asn Phe Asp Asn
1               5                   10

<210> SEQ ID NO 9
<211> LENGTH: 324
<212> TYPE: DNA
<213> ORGANISM: Artificial Sequence
<220> FEATURE:
<223> OTHER INFORMATION: synthetic

<400> SEQUENCE: 9
gacatccaga tgacccagtc tccatcctcc ctgtctgcat ctgcaggaga cagagtcacc           60
atcacttgcc gggcaagtca ggccattaga aatgatttag ctggtatca gcagaaacca          120
gggaaagccc ctaagcgcct gatctatgct gcattcaatt tgcaaagtgg ggtcccatca          180
agattcagcg gcagtggatc tgggacagaa ttcactctca caatcagtag cctgcagcct          240
gaagatcttg caagttatta ctgtcaacag tataatagat acccgtggac gttcggccaa          300
gggaccaagg tggaaatcaa acga                                                324

<210> SEQ ID NO 10
<211> LENGTH: 108
<212> TYPE: PRT
<213> ORGANISM: Artificial Sequence
<220> FEATURE:
<223> OTHER INFORMATION: synthetic

<400> SEQUENCE: 10

Asp Ile Gln Met Thr Gln Ser Pro Ser Ser Leu Ser Ala Ser Ala Gly
1               5                   10                  15

Asp Arg Val Thr Ile Thr Cys Arg Ala Ser Gln Ala Ile Arg Asn Asp
            20                  25                  30

Leu Gly Trp Tyr Gln Gln Lys Pro Gly Lys Ala Pro Lys Arg Leu Ile
            35                  40                  45

Tyr Ala Ala Phe Asn Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Leu Ala Ser Tyr Tyr Cys Gln Gln Tyr Asn Arg Tyr Pro Trp
                85                  90                  95

Thr Phe Gly Gln Gly Thr Lys Val Glu Ile Lys Arg
            100                 105

<210> SEQ ID NO 11
<211> LENGTH: 18
<212> TYPE: DNA
<213> ORGANISM: Artificial Sequence
<220> FEATURE:
<223> OTHER INFORMATION: synthetic

<400> SEQUENCE: 11
caggccatta gaaatgat                                                18

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

Gln Ala Ile Arg Asn Asp
1               5

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13 gctgcattc                                                           9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Ala Ala Phe
1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
caacagtata atagataccc gtggacg                                      27

<210> SEQ ID NO 16

<211> LENGTH: 9
<212> TYPE: PRT
<213> ORGANISM: Artificial Sequence
<220> FEATURE:
<223> OTHER INFORMATION: synthetic

<400> SEQUENCE: 16

Gln Gln Tyr Asn Arg Tyr Pro Trp Thr
1               5

<210> SEQ ID NO 17
<211> LENGTH: 847
<212> TYPE: DNA
<213> ORGANISM: Artificial Sequence
<220> FEATURE:
<223> OTHER INFORMATION: synthetic

<400> SEQUENCE: 17
agcgtccgga cccaataaca gttttaccaa gggagcagct ttctatcctg ccacactga      60
ggtgcatagc gtaatgtcca tgttgttcta cactctgatc acagcttttc tgatcggcat    120
acaggcggaa ccacactcag agagcaatgt ccctgcagga cacaccatcc cccaagccca    180
ctggactaaa cttcagcatt cccttgacac tgcccttcgc agagcccgca gcgcccggc     240
agcggcgata gctgcacgcg tggcggggca gacccgcaac attactgtgg accccaggct    300
gtttaaaaag cggcgactcc gttcaccccg tgtgctgttt agcacccagc tccccgtga    360
agctgcagac actcaggatc tggacttcga ggtcggtggt gctgcccct tcaacaggac    420
tcacaggagc aagcggtcat catcccatcc catcttccac aggggcgaat tctcggtgtg    480
tgacagtgtc agcgtgtggg ttggggataa gaccaccgcc acagacatca agggcaagga    540
ggtgatggtg ttgggagagg tgagcattaa caacagtgta ttcaaacagt acttttttga    600
gaccaagtgc cggacccaa atcccgttga cagcgggtgc cggggcattg actcaaagca    660
ctggaactca tattgtacca cgactcacac ctttgtcaag gcgctgacca tggatggcaa    720
gcaggctgcc tggcggttta ccggataga tacggcctgt atgtgtgtgc tcagcaggaa    780
ggctgtgaga agagcctgac ctgccgacac gctccctccc cctgccccttctacactctc    840
ctgggcc                                                             847

<210> SEQ ID NO 18
<211> LENGTH: 115
<212> TYPE: PRT
<213> ORGANISM: Artificial Sequence
<220> FEATURE:
<223> OTHER INFORMATION: synthetic

<400> SEQUENCE: 18

Ser Ser Ser His Pro Ile Phe His Arg Gly Glu Phe Ser Val Ser
1               5                   10                  15

Val Trp Val Gly Asp Lys Thr Thr Ala Thr Asp Ile Lys Gly Lys Glu
                20                  25                  30

Val Met Val Leu Gly Glu Val Asn Ile Asn Asn Ser Val Phe Lys Gln
            35                  40                  45

Tyr Phe Phe Glu Thr Lys Cys Arg Asp Pro Asn Pro Val Asp Ser Gly
        50                  55                  60

Cys Arg Gly Ile Asp Ser Lys His Trp Asn Ser Tyr Cys Thr Thr Thr
65                  70                  75                  80

His Thr Phe Ala Leu Thr Met Asp Gly Lys Gln Ala Ala Trp Arg Phe
                85                  90                  95

```
Ile Arg Ile Asp Thr Ala Cys Val Cys Val Leu Ser Arg Lys Ala Val
            100                 105                 110

Arg Arg Ala
        115
```